(12) United States Patent
Dormer et al.

(10) Patent No.: US 10,331,852 B2
(45) Date of Patent: Jun. 25, 2019

(54) MEDICAL IMAGING AND EFFICIENT SHARING OF MEDICAL IMAGING INFORMATION

(71) Applicant: ARTERYS INC., San Francisco, CA (US)

(72) Inventors: Kyle Dormer, Calgary (CA); Hussein Patni, Calgary (CA); Darryl Bidulock, Calgary (CA); John Axerio-Cilies, San Francisco, CA (US); Torin Arni Taerum, Calgary (CA)

(73) Assignee: Arterys Inc., San Francisco, CA (US)

( * ) Notice: Subject to any disclaimer, the term of this patent is extended or adjusted under 35 U.S.C. 154(b) by 190 days.

(21) Appl. No.: 15/363,683

(22) Filed: Nov. 29, 2016

(65) Prior Publication Data

US 2017/0076043 A1 Mar. 16, 2017

Related U.S. Application Data

(63) Continuation-in-part of application No. 15/112,130, filed as application No. PCT/US2015/011851 on Jan. 16, 2015, now Pat. No. 10,117,597.

(Continued)

(51) Int. Cl.
*G06F 19/00* (2018.01)
*G06F 21/62* (2013.01)

(52) U.S. Cl.
CPC ........ *G06F 19/321* (2013.01); *G06F 21/6254* (2013.01)

(58) Field of Classification Search
CPC .. G06F 19/321; G06F 21/6254; G06F 19/322; G06F 19/00; G16H 10/60; G06Q 50/24
See application file for complete search history.

(56) References Cited

U.S. PATENT DOCUMENTS 6,032,120 A 2/2000 Rock et al.
6,377,832 B1 4/2002 Bergman et al.
(Continued)

FOREIGN PATENT DOCUMENTS

WO 00/67185 A1 11/2000
WO 2017/091834 A1 6/2017
WO 2017/091835 A2 6/2017

OTHER PUBLICATIONS

American College of Radiology, "Liver Reporting & Data System," URL=https://www.acr.org/Clinical-Resources/Reporting-and-Data-Systems/LI-RADS, download date Jun. 28, 2018, 4 pages.
(Continued)

*Primary Examiner* — Yon J Couso
(74) *Attorney, Agent, or Firm* — Seed IP Law Group LLP

(57) ABSTRACT

An MRI image processing and analysis system may identify instances of structure in MRI flow data, e.g., coherency, derive contours and/or clinical markers based on the identified structures. The system may be remotely located from one or more MRI acquisition systems, and perform: error detection and/or correction on MRI data sets (e.g., phase error correction, phase aliasing, signal unwrapping, and/or on other artifacts); segmentation; visualization of flow (e.g., velocity, arterial versus venous flow, shunts) superimposed on anatomical structure, quantification; verification; and/or generation of patient specific 4-D flow protocols. A protected health information (PHI) service is provided which de-identifies medical study data and allows medical providers to control PHI data, and uploads the de-identified data to an analytics service provider (ASP) system. A web application is provided which merges the PHI data with the de-identified data while keeping control of the PHI data with the medical provider.

30 Claims, 21 Drawing Sheets

Related U.S. Application Data

(60) Provisional application No. 61/928,702, filed on Jan. 17, 2014, provisional application No. 62/415,203, filed on Oct. 31, 2016, provisional application No. 62/260,565, filed on Nov. 29, 2015.

(56) References Cited

U.S. PATENT DOCUMENTS

| | | | |
|---|---|---|---|
| 7,523,505 | B2 | 4/2009 | Menschik et al. |
| 7,974,924 | B2 | 7/2011 | Holla et al. |
| 8,073,712 | B2 | 12/2011 | Jacobus et al. |
| 8,090,596 | B2 | 1/2012 | Maresh et al. |
| 8,099,307 | B2 | 1/2012 | Maresh et al. |
| 8,108,228 | B2 | 1/2012 | Maresh et al. |
| 8,108,912 | B2 | 1/2012 | Ferris |
| 8,458,202 | B2 | 6/2013 | Noumeir |
| 8,615,412 | B2 | 12/2013 | Menschik et al. |
| 8,639,950 | B2 | 1/2014 | Ferris |
| 8,731,967 | B2 | 5/2014 | Jacobus et al. |
| 8,799,221 | B2 | 8/2014 | Canessa et al. |
| 8,948,478 | B2 | 2/2015 | Keefe et al. |
| 9,112,836 | B2 | 8/2015 | Ferris |
| 9,118,641 | B1 | 8/2015 | Paris, III |
| 9,430,828 | B2 | 8/2016 | Wu et al. |
| 2002/0010679 | A1* | 1/2002 | Felsher ............. G06F 19/328 705/51 |
| 2002/0146159 | A1 | 10/2002 | Nolte |
| 2005/0238233 | A1 | 10/2005 | Mulet Parada et al. |
| 2006/0106877 | A1 | 5/2006 | Lee |
| 2007/0061460 | A1 | 3/2007 | Khan et al. |
| 2008/0039713 | A1 | 2/2008 | Thomson et al. |
| 2009/0226064 | A1 | 9/2009 | El Fakhri et al. |
| 2010/0082369 | A1* | 4/2010 | Prenelus ............. G06Q 50/24 705/3 |
| 2010/0134491 | A1 | 6/2010 | Borland et al. |
| 2010/0280352 | A1 | 11/2010 | Ionasec et al. |
| 2012/0271156 | A1 | 10/2012 | Bi et al. |
| 2013/0066229 | A1 | 3/2013 | Wolff |
| 2013/0259351 | A1 | 10/2013 | Wiemker, II |
| 2014/0112564 | A1 | 4/2014 | Hsiao et al. |
| 2014/0244305 | A1 | 8/2014 | Schoenberg |
| 2014/0309521 | A1 | 10/2014 | Wang |
| 2014/0341426 | A1 | 11/2014 | Wu et al. |
| 2015/0149208 | A1 | 5/2015 | Lynch et al. |
| 2015/0213226 | A1 | 7/2015 | Wolniewicz |
| 2015/0223057 | A1 | 8/2015 | Dellarciprete et al. |
| 2016/0085915 | A1* | 3/2016 | Seow ............. G16H 10/60 705/3 |
| 2016/0335397 | A1* | 11/2016 | Blum ............. G06F 17/3033 |
| 2016/0350482 | A1* | 12/2016 | Wesemann ............. G06F 19/322 |

OTHER PUBLICATIONS

American College of Radiology, "Lung CT Screening Reporting & Data System," URL=https://www.acr.org/Clinical-Resources/Reporting-and-Data-Systems/Lung-Rads, download date Jun. 28, 2018, 4 pages.

Armato III et al., "The Lung Image Database Consortium (LIDC) and Image Database Resource Initiative (IDRI): A Completed Reference Database of Lung Nodules on CT Scans," *Medical Physics* 38(2):915-931, 2011.

Berens et al., "ZNET—Lung Nodule Detection," Lung Nodule Analysis 2016, URL=https://luna16.grand-challenge.org/serve/public_html/.../ZNET_NDET_160831.pdf/, download date Jun. 28, 2018, 4 pages.

Bidulock et al., "Systems and Methods for Longitudinally Tracking Fully De-Identified Medical Studies," U.S. Appl. No. 62/589,766, filed Nov. 22, 2017, 145 pages.

Chung et al., "Malignancy estimation of Lung-RADS criteria for subsolid nodules on CT: accuracy of low and high risk spectrum when using NLST nodules," *European Radiology* 27(11):4672-4679, 2017.

European Office Action, dated May 29, 2018, for European Application No. 15737417.4-1115, 5 pages.

Extended European Search Report, dated Jul. 14, 2017, for European Application No. 15737417.4-1657, 8 pages.

Firmino et al., "Computer-aided detection (CADe) and diagnosis (CADx) system for lung cancer with likelihood of malignancy," *BioMedical Engineering OnLine* 15:2, 2016. (17 pages).

Fluckiger et al., "Left Atrial Flow Velocity Distribution and Flow Coherence Using Four-Dimensional FLOW MRI: A Pilot Study Investigating the Impact of Age and Pre- and Postintervention Atrial Fibrillation on Atrial Hemodynamics," *Journal of Magnetic Resonance Imaging* 38(3):580-587, 2013.

Golden et al., "Autonomous Detection of Medical Study Types," U.S. Appl. No. 62/589,833, filed Nov. 22, 2017, 177 pages.

Gulshan et al., "Development and Validation of a Deep Learning Algorithm for Detection of Diabetic Retinopathy in Retinal Fundus Photographs," *Journal of the American Medical Association* 316(22):2402-2410, 2016.

He et al., "Deep Residual Learning for Image Recognition," *IEEE Conference on Computer Vision and Pattern Recognition*, Las Vegas, Nevada, USA, Jun. 27-30, 2016, pp. 770-778.

He et al., "Identity Mappings in Deep Residual Networks," $14^{th}$ *European Conference on Computer Vision*, Amsterdam, The Netherlands, Oct. 8-16, 2016, 15 pages.

Huhdanpaa et al., "Image Coregistration: Quantitative Processing Framework for the Assessment of Brain Lesions," *Journal of Digital Imaging* 27(3):369-379, 2014.

International Preliminary Report on Patentability, dated May 29, 2018, for International Application No. PCT/US2016/064029, 6 pages.

International Preliminary Report on Patentability, dated May 29, 2018, for International Application No. PCT/US2016/064031, 15 pages.

International Preliminary Report on Patentability, dated Jul. 19, 2016, for International Application No. PCT/US2015/011851, 13 pages.

International Search Report and Written Opinion, dated Jul. 17, 2015, for International Application No. PCT/US2015/011851, 17 pages.

Kass et al., "Snakes: Active Contour Models," *International Journal of Computer Vision* 1(4):321-331, 1988.

Kingma et al., "Adam: A Method for Stochastic Optimization," $3^{rd}$ *International Conference for Learning Representations*, San Diego, California, USA, May 7-9, 2015, 15 pages.

Kuhn, "The Hungarian Method for the Assignment Problem," *Naval Research Logistics Quarterly* 2(1-2):83-97, 1955. (16 pages).

Lecun et al., "Gradient-Based Learning Applied to Document Recognition," *Proceedings of the IEEE* 86(11):2278-2324, 1998.

Muja et al., "Fast Approximate Nearest Neighbors with Automatic Algorithm Configuration," *International Conference on Computer Vision Theory and Applications*, Lisboa, Portugal, Feb. 5-8, 2009, pp. 331-340.

National Lung Screening Trial Research Team, "Reduced Lung-Cancer Mortality with Low-Dose Computed Tomographic Streaming," *The New England Journal of Medicine* 365(5):395-409, 2011.

Öberg, "Segmentation of cardiovascular tree in 4D from PC-MRI images," master's thesis, Lund University, Lund, Sweden, Apr. 8, 2013, 49 pages.

Paszke et al., "ENet: A Deep Neural Network Architecture for Real-Time Semantic Segmentation," *The Computing Research Repository* 1606.02147, 2016. (10 pages).

Ronneberger et al., "U-Net: Convolutional Networks for Biomedical Image Segmentation," $18^{th}$ *International Conference on Medical Image Computing and Computer-Assisted Intervention*, Munich, Germany, Oct. 5-9, 2015, pp. 234-241.

Rosenfeld et al., "An Improved Method of Angle Detection on Digital Curves," *IEEE Transactions on Computers* C-24(9):940-941, 1975.

Russakovsky et al., "ImageNet Large Scale Visual Recognition Challenge," *International Journal of Computer Vision* 115(3):211-252, 2015.

Simard et al., "Best Practices for Convolutional Neural Networks Applied to Visual Document Analysis," $7^{th}$ *International Confer-*

(56) References Cited

OTHER PUBLICATIONS

*ence on Document Analysis and Recognition*, Edinburgh, United Kingdom, Aug. 3-6, 2003, pp. 958-963.

Simpson et al., "Estimation of Coherence Between Blood Flow and Spontaneous EEG Activity in Neonates," *IEEE Transactions on Biomedical Engineering* 52(5): 852-858, 2005.

Töger et al., "Vortex Ring Formation in the Left Ventricle of the Heart: Analysis by 4D Flow MRI and Lagrangian Coherent Structures," *Annals of Biomedical Engineering* 40(12):2652-2662, 2012.

Van Riel et al., "Observer Viability for Classification of Pulmonary Nodules on Low-Dose CT Images and Its Effect on Nodule Management," *Radiology* 277(3):863-871, 2015.

Wong et al., "Segmentation of Myocardium Using Velocity Field Constrained Front Propagation," *6th IEEE Workshop on Applications of Computer Vision*, Orlando, Florida, USA, Dec. 3-4, 2002, pp. 84-89.

Zhao et al., "Performance of computer-aided detection of pulmonary nodules in low-dose CT: comparison with double reading by nodule volume," *European Radiology* 22(10):2076-2084, 2012.

De Francesco et al., "Medical Imaging, Efficient Sharing and Secure Handling of Medical Imaging Information," U.S. Appl. No. 62/501,613, filed May 4, 2017, 146 pages.

International Search Report and Written Opinion, dated Feb. 28, 2017, for International Application No. PCT/US2016/064029, 8 pages.

International Search Report and Written Opinion, dated Jun. 7, 2017, for International Application No. PCT/US2016/064031, 20 pages.

\* cited by examiner

MEDICAL IMAGING AND EFFICIENT SHARING OF MEDICAL IMAGING INFORMATION

BACKGROUND

Technical Field

The present disclosure generally relates to magnetic resonance imaging (MRI), for instance four-dimensional (4-D) flow MRI, and the sharing of medical imaging and other information over communications networks or channels.

Description of the Related Art

MRI is most commonly employed in medical imaging, although can be used in other fields. MRI machines include a main magnet which is typically an annular array of coils having a central or longitudinal bore. The main magnet is capable of producing a strong stable magnetic field (e.g., 0.5 Tesla to 3.0 Tesla). The bore is sized to receive at least a portion of an object to be imaged, for instance a human body. When used in medical imaging applications, the MRI machine may include a patient table which allows a prone patient to be easily slid or rolled into and out of the bore.

MRI machines also include gradient magnets. The gradient magnets produce a variable magnetic field that is relatively smaller than that produced by the main magnet (e.g., 180 Gauss to 270 Gauss), allowing selected portions of an object (e.g., patient) to be imaged. MRI machines also include radio frequency (RF) coils which are operated to apply radiofrequency energy to selected portions of the object (e.g., patient) to be imaged. Different RF coils may be used for imaging different structures (e.g., anatomic structures). For example, one set of RF coils may be appropriate for imaging a neck of a patient, while another set of RF coils may be appropriate for imaging a chest or heart of the patient. MRI machines commonly include additional magnets, for example resistive magnets and/or permanent magnets.

The MRI machine typically includes, or is communicatively coupled to a computer system used to control the magnets and/or coils and/or to perform image processing to produce images of the portions of the object being imaged. Conventionally, MRI machines produce magnitude data sets which represent physical structures, for instance anatomical structures. The data sets often conform to the Digital Imaging and Communications in Medicine (DICOM) standard. DICOM files typically include pixel data and metadata in a prescribed format.

BRIEF SUMMARY

A method of operating a medical analytics platform, the medical analytics platform including an analytics service provider (ASP) system and a protected health information (PHI) system, the method may be summarized as including: storing, by at least one processor of the ASP system, de-identified medical study data on at least one nontransitory processor-readable storage medium of the ASP system; storing, by at least one processor of the PHI system, PHI data associated with the de-identified medical study data on at least one nontransitory processor-readable storage medium of the PHI system; sending, by the at least one processor of the PHI system, PHI data for a requested medical study to a client processor-based device over at least one communications network; and sending, by the at least one processor of the ASP system, de-identified medical study data for the requested medical study to the client processor-based device over the at least one communications network.

The PHI system may be communicatively coupled to a private network, the method may further include: verifying, by the at least one processor of the ASP system or the at least one processor of the PHI system, that the client processor-based device has access to the private network. The method may further include: receiving, by the at least one processor of the ASP system, a request for a PHI access token from the client processor-based device over the at least one communications network; sending, by the at least one processor of the ASP system, an encrypted PHI access token to the client processor-based device over the at least one communications network; receiving, by the at least one processor of the PHI system, a request for PHI data for the medical study from the client processor-based device, the request including the encrypted PHI access token; sending, by the at least one processor of the PHI system, the encrypted PHI access token to the ASP system over the at least one communications network; validating, by the at least one processor of the ASP system, the received encrypted PHI access token; and notifying, by the at least one processor of the ASP system, the PHI system that the PHI access token is valid, wherein sending the requested PHI data to the client processor-based device may be responsive to the at least one processor of the PHI system receiving the validation notification from the ASP system. The method may further include: receiving, by the at least one processor of the PHI system, medical study data which includes PHI data; removing, by the at least one processor of the PHI system, the PHI data from the medical study data to generate de-identified medical study data; storing, by the at least one processor of the PHI system, the PHI data in the at least one nontransitory processor-readable storage medium of the PHI system; and sending, by the at least one processor of the PHI system, the de-identified medical study data to the ASP system over the at least one communications network. Receiving medical study data which includes PHI data may include receiving medical imaging data from a scanner. Sending the de-identified medical study data to the ASP system may include sending the de-identified medical study data to the ASP system using a representational state transfer (REST) application programming interface. Removing the PHI data from the medical study data may include: removing, by the at least one processor of the PHI system, fields which are allowed to be deleted; and replacing, by the at least one processor of the PHI system, data in fields which are not allowed to be deleted with obfuscated replacement data. The method may further include: associating, by the at least one processor of the PHI system, a unique identifier with the medical study data for a medical study; storing, by the at least one processor of the PHI system, the unique identifier in the at least one nontransitory processor-readable storage medium of the PHI system; and sending, by the at least one processor of the PHI system, the unique identifier with the de-identified medical data for the medical study to the ASP system over the at least one communications network. The method may further include: receiving, by at least one processor of the client processor-based device, the PHI data from the PHI system over the at least one communications network; receiving, by the at least one processor of the client processor-based device, the de-identified medical study data from the ASP system over the at least one communications network; merging, by the at least one processor of the client processor-based device, the PHI data and the de-identified medical study data to generate re-identified medical study data; and presenting, by the at least one processor of the client processor-based device, the re-identified medical study data to a user of the client processor-based device. The method may further include: generating, by the at least one processor of the ASP system, analytics data relating to the de-identified medical study data; and sending, by the at least one processor of the ASP system, the generated analytics data to the PHI system over the at least one communications network. The method may further include: receiving, by the at least one processor of the ASP system, a request to generate analytics data from the client processor-based device over the at least one communications network, wherein generating the analytics data may be responsive to receiving the request to generate analytics data from the client processor-based device. Generating analytics data may include generating at least one of a report or a secondary capture object, and sending the generated analytics data to the PHI system may include sending the at least one of the report or the secondary capture object to the PHI system over the at least one communications network for storage on the at least one nontransitory processor-readable storage medium communicatively coupled with the PHI system. The method may further include: providing, by the at least one processor of the PHI system, a list of available studies to the client processor-based device over the at least one communications network; and receiving, by the at least one processor of the PHI system, a selection of at least one of the available studies in the list from the client processor-based device over the at least one communications network. The method may further include: periodically sending, by the at least one processor of the PHI system, a check for updates to the ASP system over the at least one communications network; determining, by the at least one processor of the ASP system, whether any updates to the PHI system are needed; and responsive to determining that at least one update of the PHI system is needed, sending, by the at least one processor of the ASP, update data to the PHI system over the at least one communications network.

A method of operating an analytics service provider (ASP) system of a medical analytics platform, the medical analytics platform including the ASP system and a protected health information (PHI) system, the PHI system storing PHI data associated with de-identified medical study data on at least one nontransitory processor-readable storage medium of the PHI system, the method may be summarized as including: storing, by at least one processor of the ASP system, the de-identified medical study data on at least one nontransitory processor-readable storage medium of the ASP system; and sending, by the at least one processor of the ASP system, de-identified medical study data for a requested medical study to a client processor-based device over at least one communications network to be merged by the client processor-based device with PHI data received by the client processor-based device from the PHI system over the at least one communications network.

The method may further include: receiving, by the at least one processor of the ASP system, a request for a PHI access token from the client processor-based device over the at least one communications network; sending, by the at least one processor of the ASP system, an encrypted PHI access token to the client processor-based device over the at least one communications network; receiving, by the at least one processor of the ASP system, the encrypted PHI access token from the PHI system over the at least one communications network; validating, by the at least one processor of the ASP system, the received encrypted PHI access token; and notifying, by the at least one processor of the ASP system, the PHI system that the PHI access token is valid. The method may further include: receiving, by the at least one processor of the ASP system, the de-identified medical study data from the PHI system over the at least one communications network. The method may further include: generating, by the at least one processor of the ASP system, analytics data relating to the de-identified medical study data; and sending, by the at least one processor of the ASP system, the generated analytics data to the PHI system over the at least one communications network. The method may further include: receiving, by the at least one processor of the ASP system, a request to generate analytics data from the client processor-based device over the at least one communications network, wherein generating the analytics data may be responsive to receiving the request to generate analytics data from the client processor-based device. Generating analytics data may include generating at least one of a report or a secondary capture object, and sending the generated analytics data to the PHI system may include sending the at least one of the report or the secondary capture object to the PHI system over the at least one communications network for storage on the at least one nontransitory processor-readable storage medium communicatively coupled with the PHI system. The method may further include: periodically receiving, by the at least one processor of the ASP system, a check for updates from the PHI system over the at least one communications network; determining, by the at least one processor of the ASP system, whether any updates to the PHI system are needed; and responsive to determining that at least one update of the PHI system is needed, sending, by the at least one processor of the ASP, update data to the PHI system over the at least one communications network. The method may further include: receiving, by at least one processor of the client processor-based device, the PHI data from the PHI system over the at least one communications network; receiving, by the at least one processor of the client processor-based device, the de-identified medical study data from the ASP system over the at least one communications network; merging, by the at least one processor of the client processor-based device, the PHI data and the de-identified medical study data to generate re-identified medical study data; and presenting, by the at least one processor of the client processor-based device, the re-identified medical study data to a user of the client processor-based device.

An analytics service provider (ASP) system of a medical analytics platform, the medical analytics platform including the ASP system and a protected health information (PHI) system, the PHI system stores PHI data associated with de-identified medical study data on at least one nontransitory processor-readable storage medium of the PHI system, the ASP system may be summarized as including: at least one nontransitory processor-readable storage medium that stores at least one of processor-executable instructions or data; and at least one processor communicably coupled to the at least one nontransitory processor-readable storage medium, in operation the at least one processor: stores the de-identified medical study data on the at least one nontransitory processor-readable storage medium; and sends de-identified medical study data for a requested medical study to a client processor-based device over at least one communications network to be merged by the client processor-based device with PHI data received by the client processor-based device from the PHI system over the at least one communications network.

The at least one processor may: receive a request for a PHI access token from the client processor-based device over at least one communications network; send an encrypted PHI access token to the client processor-based device over the at least one communications network; receive the encrypted PHI access token from the PHI system over the at least one communications network; validate the received encrypted PHI access token; and notify the PHI system that the PHI access token is valid over the at least one communications network. The at least one processor may: receive the de-identified medical study data from the PHI system over the at least one communications network. The at least one processor may: generate analytics data relating to the de-identified medical study data; and send the generated analytics data to the PHI system over the at least one communications network. The at least one processor may: receive a request to generate analytics data from the client processor-based device over the at least one communications network, wherein the at least one processor may generate the analytics data responsive to receipt of the request to generate analytics data from the client processor-based device. The analytics data may include at least one of a report or a secondary capture object, and the at least one processor may: send the at least one of the report or the secondary capture object to the PHI system over the at least one communications network for storage on at least one nontransitory processor-readable storage medium communicatively coupled with the PHI system. The at least one processor may: periodically receive a check for updates from the PHI system over the at least one communications network; determine whether any updates to the PHI system are needed; and responsive to a determination that at least one update of the PHI system is needed, send update data to the PHI system over the at least one communications network.

A method of operating a protected health information (PHI) system of a medical analytics platform, the medical analytics platform including the PHI system and an analytics service provider (ASP) system, the ASP system storing de-identified medical study data on at least one nontransitory processor-readable storage medium of the ASP system, the method may be summarized as including: storing, by at least one processor of the PHI system, PHI data associated with the de-identified medical study data on at least one nontransitory processor-readable storage medium of the PHI system; and sending, by the at least one processor of the PHI system, PHI data for a requested medical study to a client processor-based device over at least one communications network to be merged by the client processor-based device with de-identified medical study data received by the client processor-based device from the ASP system over the at least one communications network.

The method may further include: receiving, by the at least one processor of the PHI system, a request for PHI data for the medical study from a client processor-based device, the request including an encrypted PHI access token; sending, by the at least one processor of the PHI system, the encrypted PHI access token to the ASP system over the at least one communications network for validation; and receiving, by the at least one processor of the PHI system, a notification from the ASP system that the PHI access token is valid. The method may further include: receiving, by the at least one processor of the PHI system, medical study data which includes PHI data; removing, by the at least one processor of the PHI system, the PHI data from the medical study data to generate de-identified medical study data; storing, by the at least one processor of the PHI system, the PHI data in the at least one nontransitory processor-readable storage medium of the PHI system; and sending, by the at least one processor of the PHI system, the de-identified medical study data to the ASP system over the at least one communications network. Receiving medical study data which includes PHI data may include receiving medical imaging data from a scanner. Sending the de-identified medical study data to the ASP system may include sending the de-identified medical study data to the ASP system using a representational state transfer (REST) application programming interface. Removing the PHI data from the medical study data may include: removing, by the at least one processor of the PHI system, fields which are allowed to be deleted; and replacing, by the at least one processor of the PHI system, data in fields which are not allowed to be deleted with obfuscated replacement data. The method may further include: associating, by the at least one processor of the PHI system, a unique identifier with the medical study data for a medical study; storing, by the at least one processor of the PHI system, the unique identifier in the at least one nontransitory processor-readable storage medium of the PHI system; and sending, by the at least one processor of the PHI system, the unique identifier with the de-identified medical data for the medical study to the ASP system over the at least one communications network. The method may further include: receiving, by the at least one processor of the PHI system, analytics data relating to the de-identified medical study data from the ASP system over the at least one communications network; and storing, by the at least one processor of the PHI system, the received analytics data on at least one nontransitory processor-readable storage medium communicatively coupled with the PHI system. The method may further include: providing, by the at least one processor of the PHI system, a list of available studies to the client processor-based device over the at least one communications network; and receiving, by the at least one processor of the PHI system, a selection of at least one of the available studies in the list from the client processor-based device over the at least one communications network. The method may further include: periodically sending, by the at least one processor of the PHI system, a check for updates to the ASP system over the at least one communications network; and receiving, by the at least one processor of the PHI system, update data from the ASP system over the at least one communications network. The method may further include: receiving, by at least one processor of the client processor-based device, the PHI data from the PHI system over the at least one communications network; receiving, by the at least one processor of the client processor-based device, the de-identified medical study data from the ASP system over the at least one communications network; merging, by the at least one processor of the client processor-based device, the PHI data and the de-identified medical study data to generate re-identified medical study data; and presenting, by the at least one processor of the client processor-based device, the re-identified medical study data to a user of the client processor-based device.

A protected health information (PHI) system of a medical analytics platform, the medical analytics platform including the PHI system and an analytics service provider (ASP) system, the ASP system storing de-identified medical study data on at least one nontransitory processor-readable storage medium of the ASP system, the PHI system may be summarized as including: at least one nontransitory processor-readable storage medium that stores at least one of processor-executable instructions or data; and at least one processor communicably coupled to the at least one nontransitory processor-readable storage medium, in operation the at least one processor: stores PHI data associated with the de-identified medical study data on at least one nontransitory processor-readable storage medium of the PHI system; and sends PHI data for a requested medical study to a client processor-based device over at least one communications network to be merged by the client processor-based device with de-identified medical study data received by the client processor-based device from the ASP system over the at least one communications network.

The at least one processor may: receive a request for PHI data for the medical study from a client processor-based device, the request including an encrypted PHI access token; send the encrypted PHI access token to the ASP system over the at least one communications network for validation; and receive a notification from the ASP system that the PHI access token is valid. The at least one processor may: receive medical study data which includes PHI data; remove the PHI data from the medical study data to generate de-identified medical study data; store the PHI data in the at least one nontransitory processor-readable storage medium of the PHI system; and send the de-identified medical study data to the ASP system over the at least one communications network. The medical study data may include medical imaging data from a scanner. The at least one processor may send de-identified medical study data to the ASP system using a representational state transfer (REST) application programming interface. The at least one processor may: remove fields of the medical study data which are allowed to be deleted; and replace data in fields of the medical study data which are not allowed to be deleted with obfuscated replacement data. The at least one processor may: associate a unique identifier with the medical study data for a medical study; store the unique identifier in the at least one nontransitory processor-readable storage medium of the PHI system; and send the unique identifier with the de-identified medical data for the medical study to the ASP system over the at least one communications network. The at least one processor may: receive analytics data relating to the de-identified medical study data from the ASP system over the at least one communications network; and store the received analytics data on at least one nontransitory processor-readable storage medium communicatively coupled with the PHI system. The at least one processor may: provide a list of available studies to the client processor-based device over the at least one communications network; and receive a selection of at least one of the available studies in the list from the client processor-based device over the at least one communications network. The at least one processor may: periodically send a check for updates to the ASP system over the at least one communications network; and receive update data from the ASP system over the at least one communications network.

A method of operation for use with magnetic resonance imaging (MRI) based medical imaging systems may be summarized as including receiving raw DICOM files by an anonymization service running on a clinical facility network; generating a hash of any plain text patient health information in the raw DICOM file; and replacing any plain text patient health information in the raw DICOM file with the respective hash of the plain text patient health information.

The method may further include identifying all patient health information fields in the raw DICOM file, and wherein generating a hash of any plain text patient health information in the raw DICOM file includes generating a salted hash.

The method may further include accessing a key kept within the clinical facility network that turns plain text patient health information into a hash by the anonymization service.

The method may further include allowing access to the anonymization service running on a clinical facility network from outside the clinical facility network only by a VPN of the clinical facility.

A method of operation for use with magnetic resonance imaging (MRI) based medical imaging systems may be summarized as including servicing a plurality of requests by a first proxy server, the requests coming from with a clinical facility network and from outside the clinical facility network; in response to at least some of the requests, generating plain text information from hashed patient health information by the proxy server; replacing the hashed patient health information with the plain text information by the proxy server; and transmitting the resulting information to a client device.

A method of operation for use with magnetic resonance imaging (MRI) based medical imaging systems may be summarized as including connecting by a client to a server of the MRI image processing and analysis system, the server outside a clinical facility network; checking a flag that indicates whether the client is missing information required to render the patient health information in plain text; in response to an indication that the client is missing information required to render the patient health information in plain text PHI, connecting by the client to an anonymization service; requesting the patient health information in plain text by the client from the anonymization service. Requesting the patient health information in plain text by the client from the anonymization service may include providing a hash or an identifier.

The method may further include caching the received plain text patient health information locally by the client.

The method may further include purging the cached plain text patient health by the client in response to a user logging out.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
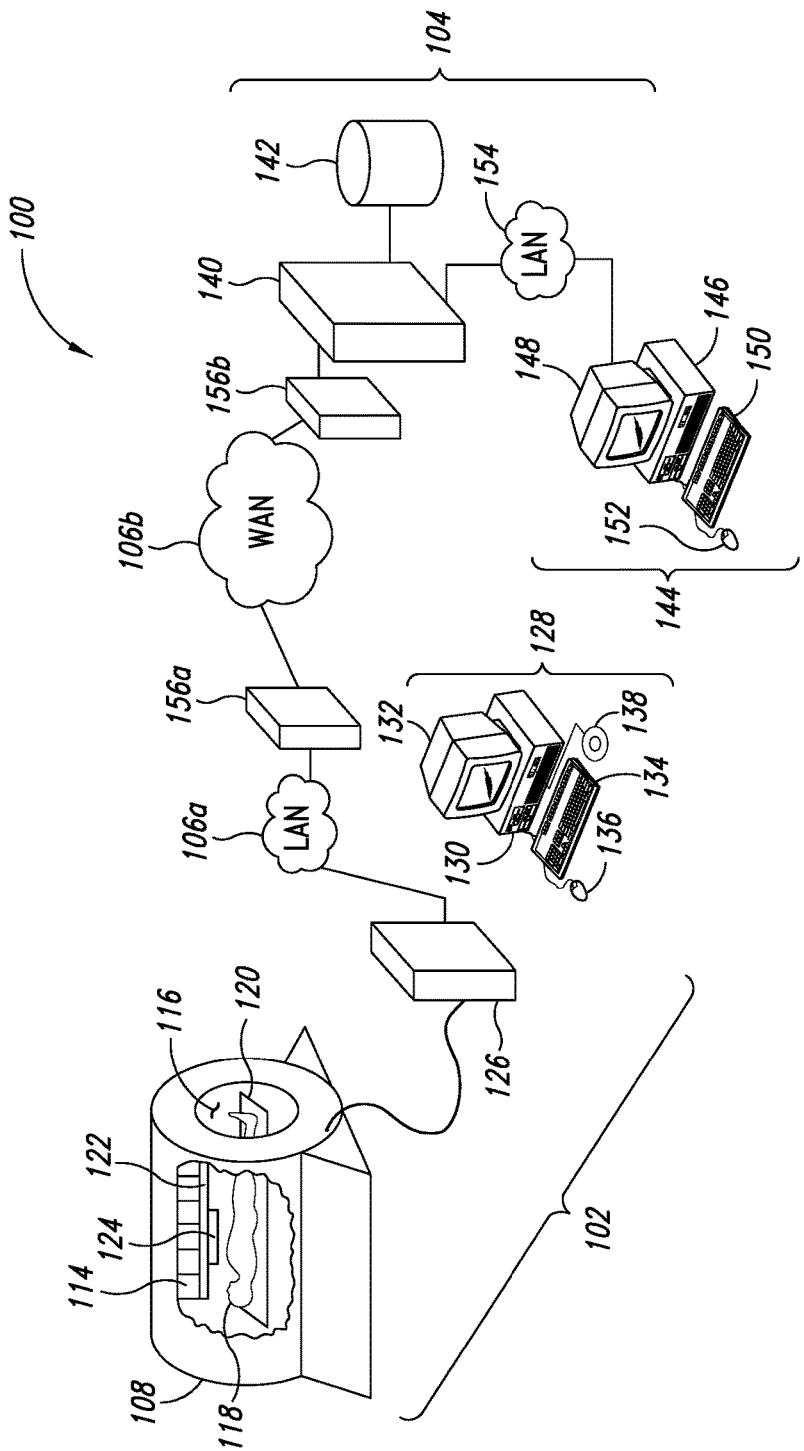
FIG. 1 is a schematic view of a networked environment including at least one MRI acquisition system and at least one image processing system, the MRI acquisition system located in a clinical setting and the image processing system located remotely from the MRI acquisition system and communicatively coupled therewith over one or more networks, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with MRI machines, computer systems, server computers, and/or communications networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are synonymous with "including," and are inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Many of the implementations described herein take advantage of a 4-D flow MRI data set, which essentially captures MRI magnitude and phase information for a three-dimensional (3-D) volume over a period of time. This approach may allow capture or acquisition of MRI data sets without requiring breath holding or synchronization or gating to a patient's cardiac or pulmonary cycles. Instead, MRI data sets are captured or acquired, and imaging processing and analysis employed to derive the desired information, for example by re-binning acquired information based on the cardiac and pulmonary cycles. This essentially pushes what is normally time-intensive acquisition operations to the imaging processing and analysis stage. As way of a simplified analogy, in some respects such may be thought of as capturing a movie of the anatomical structure (e.g., chest, heart) without concern over a patient's pulmonary or cardiac cycles, the processing the captured movie to account for relative movement introduced by the pulmonary and cardiac cycles. The captured information includes both magnitude information, which is indicative of anatomical structure, and phase information which is indicative of velocity. The phase information allows distinction between static and non-static tissue, for example allowing non-static tissue (e.g., blood, air) to be distinguished from static tissue (e.g., fat, bone). The phase information also allows certain non-static tissue (e.g., air) to be distinguished from other non-static tissue (e.g., blood). This may advantageously allow automated or even autonomous segmentation between tissues, and/or distinguishing atrial blood flow from venous blood flow. This may advantageously allow automated or even autonomous generation of flow visualization information, which may be superimposed on anatomical information. This may also advantageously allow automated or even autonomous flow quantification, identifying abnormalities and/or verifying results.

The workflow may generally be divided into three portions, sequentially: 1) image acquisition, 2) image reconstruction, and 3) image processing or post-processing and analysis. Alternatively, the workflow may be divided into 1) operational, 2) preprocessing, and 3) visualization and quantification.

Image acquisition may include determining, defining, generating or otherwise setting one or more pulse sequences, which are used to run the MRI machine (e.g., control magnets) and acquire raw MRI. Use of a 4-D flow pulse sequence allows capture of not only anatomical structure, which is represented by magnitude, but of velocity, which is represented by phase. At least one of the methods or techniques described herein, generation of patient specific 4-D pulse sequences, occurs during or as part of image acquisition portion. Image reconstruction may, for example, employ fast Fourier transformations, and result in MRI data sets, often in a form compatible with the DICOM standard. Image reconstruction has traditionally been computationally intensive often relying on supercomputers. The requirement for such is a significant burden to many clinical facilities. Many of the methods and techniques described herein occur during or as part of the imaging processor or post-processing and analysis. Such can include error detection and/or error correction, segmentation, visualization including fusion of flow related information and images of anatomical structures, quantification, identification of abnormalities including shunts, verification including identification of spurious data. Alternatively, error detection and/or error correction may occur during the preprocessing portion.

FIG. 1 shows a networked environment 100 according to one illustrated embodiment, in which one or more MRI acquisition systems (one shown) 102 are communicatively coupled to at least one image processing and analysis system 104 via one or more networks 106a, 106b (two shown, collectively 106).

The MRI acquisition system 102 is typically located at a clinical facility, for instance a hospital or dedicated medical imaging center. Various techniques and structures, as explained herein, may advantageously allow the image processing and analysis system 104 to be remotely located from the MRI acquisition system 102. The image processing and analysis system 104 may, for example, be located in another building, city, state, province or even country.

The MRI acquisition system 102 may, for example, include an MRI machine 108, a computer system 110 and an MRI operator's system 112. The MRI machine 108 may include a main magnet 114, which is typically an annular array of coils having a central or longitudinal bore 116. The main magnet 108 is capable of producing a strong stable magnetic field (e.g., 0.5 Tesla to 2.0 Tesla). The bore 116 is sized to receive at least a portion of an object to be imaged, for instance a human body 118. When used in medical imaging applications, the MRI machine 108 typically includes a patient table 120 which allows a prone patient 118 to be easily slid or rolled into and out of the bore 116.

The MRI machine also includes a set of gradient magnets 122 (only one called out). The gradient magnets 122 produce a variable magnetic field that is relatively smaller than that produced by the main magnet 114 (e.g., 180 Gauss to 270 Gauss), allowing selected portions of an object (e.g., patient) to be imaged.

MRI machine 108 also include radio frequency (RF) coils 124 (only one called out) which are operated to apply radiofrequency energy to selected portions of the object (e.g., patient 118) to be imaged. Different RF coils 124 may be used for imaging different structures (e.g., anatomic structures). For example, one set of RF coils 124 may be appropriate for imaging a neck of a patient, while another set of RF coils 124 may be appropriate for imaging a chest or heart of the patient. MRI machines 108 commonly include additional magnets, for example resistive magnets and/or permanent magnets.

The MRI machine 108 typically includes, or is communicatively coupled to, a processor-based MRI control system 126 used to control the magnets and/or coils 114, 122, 124. The processor-based control system 126 may include one or more processors, non-transitory computer- or processor-readable memory, drive circuitry and/or interface components to interface with the MRI machine 108. The processor-based control system 126 may, in some implementations, also perform some preprocessing on data resulting from the MRI operation.

An MRI operator's system 128 may include a computer system 130, monitor or display 132, keypad and/or keyboard 134, and/or a cursor control device such as a mouse 136, joystick, trackpad, trackball or the like. The MRI operator's system 128 may include or read computer- or processor executable instructions from one or more non-transitory computer- or processor-readable medium, for instance spinning media 138 such as a magnetic or optical disk. The operator's system 128 may allow a technician to operate the MRI machine 108 to capture MRI data from a patient 118. Various techniques, structures and features described herein may allow MRI machine 108 operation by a technician without requiring the presence of a clinician or physician. Such may advantageously significantly lower costs of MRI procedures. Also as described herein, various techniques, structures and features may allow MRI procedures to be performed much more quickly than using conventional techniques. Such may advantageously allow higher throughput for each MRI installation, amortizing cost of the capital intensive equipment over a much larger number of procedures. For example, high computational power computers may be located remotely from the clinical setting, and may be used to serve multiple clinical facilities. The various techniques, structures and features described herein may also additionally or alternatively advantageously reduce the time that each patient is exposed to the MRI procedure, reducing or alleviating the anxiety that often accompanies undergoing an MRI procedure. For instance, eliminating the need for breath holding and/or synchronizing with a patient's pulmonary and/or cardiac cycles via image processing and analysis techniques described herein may significantly reduce the time for acquisition, for example to eight to ten minutes.

The image processing and analysis system 104 may include one or more servers 139 to handle incoming requests and responses, and one or more rendering or image processing and analysis computers 140. The server(s) 139 may, for example take the form of one or more server computers, workstation computers, supercomputers, or personal computers, executing server software or instructions. The one or more rendering or image processing and analysis computers 140 may take the form of one or more computers, workstation computers, supercomputers, or personal computers, executing image processing and/or analysis software or instructions. The one or more rendering or image processing and analysis computers 140 will typically employ one, and preferably multiple, graphical processing units (GPUs) or GPU cores.

The image processing and analysis system 104 may include one or more non-transitory computer-readable medium 142 (e.g., magnetic or optical hard drives, RAID, RAM, Flash) that stores processor-executable instructions and/or data or other information. The image processing and analysis system 104 may include one or more image processing and analysis operator's systems 144. The image processing and analysis operator's system 144 may include a computer system 146, monitor or display 148, keypad and/or keyboard 150, and/or a cursor control device such as a mouse 152, joystick, trackpad, trackball or the like. The image processing and analysis operator's system 144 may be communicatively coupled to the rendering or image processing and analysis computer(s) 140 via one or more networks, for instance a LAN 154. While many image processing techniques and analysis may be fully automated, the image processing and analysis operator's system may allow a technician to perform certain image processing and/or analysis operations on MRI data captured from a patient.

While illustrated as a single nontransitory computer- or processor-readable storage medium 142, in many implementations the nontransitory computer- or processor-readable storage medium 142 may constitute a plurality of nontransitory storage media. The plurality of nontransitory storage media may be commonly located at a common location, or distributed at a variety of remote locations. Thus, a database of raw MRI data, preprocessed MRI data and/or processed MRI data may be implemented in one, or across more than one, nontransitory computer- or processor-readable storage media. Such database(s) may be stored separately from one another on separate computer- or processor-readable storage medium 142 or may be stored on the same computer- or processor-readable storage medium 142 as one another. The computer- or processor-readable storage medium 142 may be co-located with the image processing and analysis system 104, for example, in the same room, building or facility. Alternatively, the computer- or processor-readable storage medium 142 may be located remotely from the image processing and analysis system 104, for example, in a different facility, city, state or country. Electronic or digital information, files or records or other collections of information may be stored at specific locations in non-transitory computer- or processor-readable media 142, thus are logically addressable portions of such media, which may or may not be contiguous.

As noted above, the image processing and analysis system 104 may be remotely located from the MRI acquisition system 102. The MRI acquisition system 102 and the image processing and analysis system 104 are capable of communications, for example via one or more communications channels, for example local area networks (LANs) 106a and Wide Area Networks (WANs) 106b. The networks 106 may, for instance include packet switched communications networks, such as the Internet, Worldwide Web portion of the Internet, extranets, and/or intranets. The networks 106 may take the form of various other types of telecommunications networks, such as cellular phone and data networks, and plain old telephone system (POTS) networks. The type of communications infrastructure should not be considered limiting.

As illustrated in FIG. 1, the MRI acquisition system 102 is communicatively coupled to the first LAN 106a. The first LAN 106a may be a network operated by or for the clinical facility, providing local area communications for the clinical facility. The first LAN 106a is communicatively coupled to the WAN (e.g., Internet) 106b. A first firewall 156a may provide security for the first LAN.

Also as illustrated in FIG. 1, the image processing and analysis system 104 is communicatively coupled to the second LAN 154. The second LAN 154 may be a network operated by or for an image processing facility or entity, providing local area communications for the image processing facility or entity. The second LAN 154 is communicatively coupled to the WAN 106b (e.g., Internet). A second firewall 156b may provide security for the second LAN 154.

The image processing facility or entity may be independent from the clinical facility, for example an independent business providing services to one, two or many clinical facilities.

While not illustrated, the communications network may include one or more additional networking devices. The networking devices may take any of a large variety of forms, including servers, routers, network switches, bridges, and/or modems (e.g., DSL modem, cable modem), etc.

While FIG. 1 illustrates a representative networked environment 100, typical networked environments may include many additional MRI acquisition systems, image processing and analysis system 104, computer systems, and/or entities.

The concepts taught herein may be employed in a similar fashion with more populated networked environments than that illustrated. For example, a single entity may provide image processing and analysis services to multiple diagnostic entities. One or more of the diagnostic entities may operate two or more MRI acquisition systems 102. For example, a large hospital or dedicated medical imaging center may operate two, three or even more MRI acquisition systems at a single facility. Typically, the entity that provides the image processing and analysis services will operate multiple entity may provide image processing and analysis systems 104 which may include two, three or even hundreds of rendering or image processing and analysis computers 140.

Figure 2:
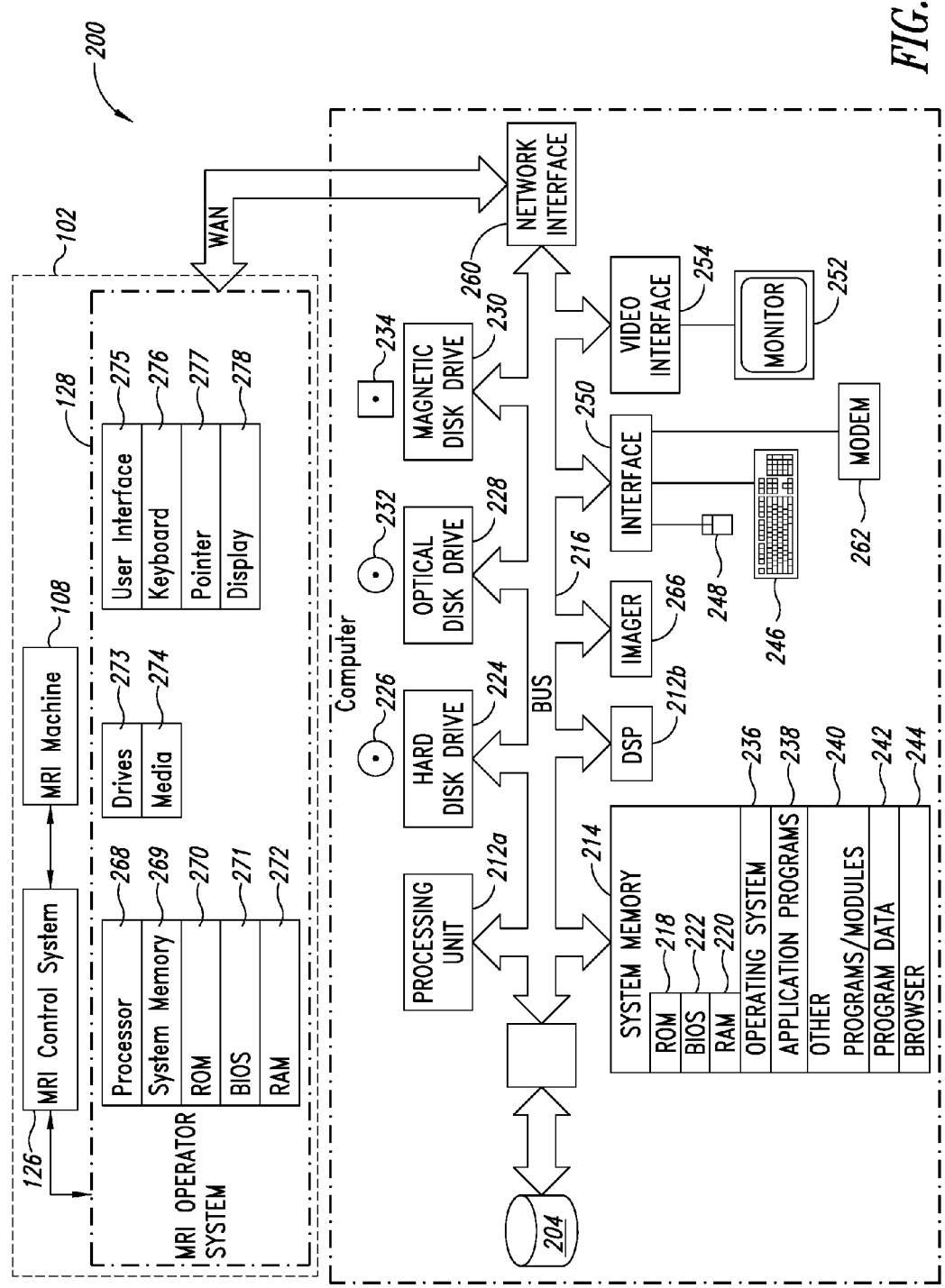
FIG. 2 is a functional block diagram of an MRI acquisition system and an MRI image processing and analysis system that provides MRI image processing and analysis services, according to one illustrated embodiment.

FIG. 2 shows a networked environment 200 comprising one or more image processing and analysis systems 104 (only one illustrated) and one or more associated nontransitory computer- or processor-readable storage medium 204 (only one illustrated). The associated nontransitory computer- or processor-readable storage medium 204 is communicatively coupled to the image processing and analysis system(s) 104 via one or more communications channels, for example, one or more parallel cables, serial cables, or wireless channels capable of high speed communications, for instance, via FireWire®, Universal Serial Bus® (USB) 2 or 3, and/or Thunderbolt®, Gigabyte Ethernet®.

The networked environment 200 also comprises one or more end MRI acquisition systems 102 (only one illustrated). The MRI acquisition system(s) 102 are communicatively coupled to the image processing and analysis system(s) 104 by one or more communications channels, for example, one or more wide area networks (WANs) 210, for instance the Internet or Worldwide Web portion thereof.

In operation, the MRI acquisition systems 102 typically function as a client to the image processing and analysis system 104. In operation, the image processing and analysis systems 104 typically functions as a server to receive requests or information (e.g., MRI data sets) from the MRI acquisition systems 102. Described herein is an overall process which employs an asynchronous command and imaging pipeline that allows the image processing and analysis to be performed remotely (e.g., over a WAN) from the MRI acquisition system 102. This approach provides for a number of distinctive advantages, for instance allowing the MRI acquisition system(s) 102 to be operated by a technician without requiring the presence of a clinician (e.g., physician). Various techniques or approaches are also described to enhance security, while allowing access to medical imaging data as well as private patient specific health information.

While illustrated as located remotely from the MRI acquisition system(s) 102, in some implementations the image processing and analysis systems 104 may be co-located with the MRI acquisition system 102. In other implementations, one or more of the operations or functions described herein may be performed by the MRI acquisition system 102 or via a processor-based device co-located with the MRI acquisition system 102.

The image processing and analysis systems 104 receive MRI data sets, perform image processing on the MRI data sets, and provide the processed MRI data sets, for example to a clinician for review. The image processing and analysis systems 104 may, for example, perform error detection and/or correction on MRI data sets, for example phase error correction, phase aliasing detection, signal unwrapping, and/or detection and/or correction of various artifacts. Phase error is related to phase, as is phase aliasing. Signal unwrapping is related to magnitude. Various other artifacts may be related to phase and/or magnitude.

The image processing and analysis systems 104 may, for example, perform segmentation, distinguishing between various tissue type. The image processing and analysis systems 104 may, for example, perform quantification, for instance comparing blood flow into and out of a closed anatomical structure or through two or more anatomical structures. The image processing and analysis systems 104 may advantageously use quantification to verify results, for example confirming identification of a certain tissue and/or providing an indication of an amount of certainty in the results. Additionally, the image processing and analysis systems 104 may advantageously use quantification to identify the existence of a shunt.

In some implementations, the image processing and analysis systems 104 may generate images which reflect blood flow, for example including distinguishing between arterial and venous blood flow. For instance, the image processing and analysis systems 104 may employ a first color map (e.g., blue) to indicate arterial blood flow and a second color map (e.g., red) to indicate venous blood flow. The image processing and analysis systems 104 may indicate aberrations (e.g., shunt) using some other, distinctive color or visual emphasis. Numerous different techniques are described for distinguishing between different tissues as wells as between arterial and venous blood flow. Flow visualization may be superimposed, for instance as one or more layers, on or over visual representations of anatomical structure or magnitude data.

In some implementations, the image processing and analysis systems 104 may generate a patient specific 4-D flow protocol for use in operating an MRI acquisition system 102 with a specific patient. Such may include setting an appropriate velocity encoding (VENC) for operation of the MRI machine.

The image processing and analysis systems 104 may perform one or more of these operations or functions autonomously, without human input. Alternatively, the image processing and analysis systems 104 may perform one or more of these operations or functions based on human input, for example human input which identifies a point, location or plane, or which otherwise identifies a characteristic of anatomical tissue. Some planes and/or views may be predefined, allowing the operator, user or clinician to simply select a plane (e.g., a valve plane) or a denominated view (e.g., 2 chamber view, 3 chamber view, 4 chamber view) to quickly and easily obtain the desired view.

The networked environment 200 may employ other computer systems and network equipment, for example, additional servers, proxy servers, firewalls, routers and/or bridges. The image processing and analysis systems 104 will at times be referred to in the singular herein, but this is not intended to limit the embodiments to a single device since in typical embodiments there may be more than one image processing and analysis systems 104 involved. Unless described otherwise, the construction and operation of the various blocks shown in FIG. 2 are of conventional design. As a result, such blocks need not be described in further detail herein, as they will be understood by those skilled in the relevant art.

The image processing and analysis systems 104 may include one or more processing units 212a, 212b (collectively 212), a system memory 214 and a system bus 216 that couples various system components, including the system memory 214 to the processing units 212. The processing units 212 may be any logic processing unit, such as one or more central processing units (CPUs) 212a, digital signal processors (DSPs) 212b, application-specific integrated circuits (ASICs), field programmable gate arrays (FPGAs), etc. The system bus 216 can employ any known bus structures or architectures, including a memory bus with memory controller, a peripheral bus, and/or a local bus. The system memory 214 includes read-only memory ("ROM") 218 and random access memory ("RAM") 220. A basic input/output system ("BIOS") 222, which can form part of the ROM 218, contains basic routines that help transfer information between elements within the image processing and analysis system(s) 104, such as during start-up.

The image processing and analysis system(s) 104 may include a hard disk drive 224 for reading from and writing to a hard disk 226, an optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable media 226, 232, 234, provide nonvolatile storage of computer-readable instructions, data structures, program modules and other data for the image processing and analysis system(s) 104. Although the depicted image processing and analysis systems 104 is illustrated employing a hard disk 224, optical disk 228 and magnetic disk 230, those skilled in the relevant art will appreciate that other types of computer-readable media that can store data accessible by a computer may be employed, such as WORM drives, RAID drives, magnetic cassettes, flash memory cards, digital video disks ("DVD"), Bernoulli cartridges, RAMs, ROMs, smart cards, etc.

Program modules can be stored in the system memory 214, such as an operating system 236, one or more application programs 238, other programs or modules 240 and program data 242. Application programs 238 may include instructions that cause the processor(s) 212 to perform image processing and analysis on MRI image data sets. For example, the application programs 238 may include instructions that cause the processor(s) 212 to perform phase error correction on phase or velocity related data. For example, the application programs 238 may include instructions that cause the processor(s) 212 to correct for phase aliasing. Also for example, the application programs 238 may include instructions that cause the processor(s) 212 to perform signal unwrapping. Additionally or alternatively, the application programs 238 may include instructions that cause the processor(s) 212 to identify and/or correct for artifacts.

The application programs 238 may include instructions that cause the processor(s) 212 to, for example, perform segmentation, distinguishing between various tissue type. The application programs 238 may include instructions that cause the processor(s) 212 to perform quantification, for instance comparing blood flow into and out of a closed anatomical structure or through two or more anatomical structures. The application programs 238 may include instructions that cause the processor(s) 212 to use quantification to verify results, for example confirming identification of a certain tissue and/or providing an indication of an amount of certainty in the results. The application programs

238 may include instructions that cause the processor(s) 212 to use quantification to identify the existence of a shunt.

The application programs 238 may include instructions that cause the processor(s) 212 to generate images which reflect blood flow, for example distinguishing between arterial and venous blood flow. For instance, a first color map (e.g., blue) may be used to indicate arterial blood flow and a second color map (e.g., red) to indicate venous blood flow. Aberrations (e.g., shunt) may be indicated using some other, distinctive color or visual emphasis. Color transfer functions may be applied to generate the color maps. The application programs 238 may include instructions that cause the processor(s) 212 to superimpose visualization of flow (e.g., MrII phase data indicative of blood flow velocity and/or volume) on visualization or rendered images of anatomy (e.g., MRI magnitude data). The instructions may cause the flow visualization to be rendered as one or more layers on the images of the anatomy to provide a fusion of anatomy (i.e., magnitude) and flow (i.e., phase) information, for example as a color heat map and/or as vectors (e.g., arrow icons) with direction and magnitude (e.g., represented by length, line weight). The instructions may additionally or alternatively cause the generation of spatial mappings or visualization of signal dispersion, turbulence and/or pressure, which may be overlaid or superimposed on a spatial mapping or visualization of anatomical structure. Fusing visualization of phase or velocity related information with visualization of anatomical information or visual representations of anatomical structures may facilitate the identification of anatomical landmarks. The instructions may make use of sets or arrays of graphics processing units or GPUs to quickly render the visualizations.

Transfer functions may also be applied to determine which visual effects (e.g., color) to apply to which tissue. For example, arterial blood flow may be colored in shades of blue and venous blood flow in shades of red, while fat tissue colored as yellow. Anatomical structure, represented as magnitude in the MRI image data set, may, for example, be visualized using grey scale. Depth of view may be operator or user adjustable, for example via a slider control on a graphical user interface. Thus, visualization may be in the form a fusion view that advantageously fuses a visual representation of velocity information with a visual representation of anatomical information or representation.

The application programs 238 may include instructions that cause the processor(s) 212 to generate a patient specific 4-D flow protocol for use in operating an MRI acquisition system 102 with a specific patient. Such may be based on patient specific input, for example provided by a technician, and may be based on the particular MRI machine being used to capture the MRI data set.

The application programs 238 may include instructions that cause the processor(s) 212 to receive image data sets from the MRI acquisition system, process and/or analyze the image data sets, and provide processed and/or analyzed images and other information to users remotely located from the image processing, in a time sensitive and secure manner. Such is described in detail herein with reference to the various Figures.

The system memory 214 may also include communications programs, for example, a server 244 that causes the image processing and analysis system(s) 104 to serve electronic information or files via the Internet, intranets, extranets, telecommunications networks, or other networks as described below. The server 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of suitable servers may be commercially available such as those from Mozilla, Google, Microsoft and Apple Computer.

While shown in FIG. 2 as being stored in the system memory 214, the operating system 236, application programs 238, other programs/modules 240, program data 242 and server 244 can be stored on the hard disk 226 of the hard disk drive 224, the optical disk 232 of the optical disk drive 228 and/or the magnetic disk 234 of the magnetic disk drive 230.

An operator can enter commands and information into the image processing and analysis system(s) 104 through input devices such as a touch screen or keyboard 246 and/or a pointing device such as a mouse 248, and/or via a graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The image processing and analysis system(s) 104 can include other output devices, such as speakers, printers, etc.

The image processing and analysis systems 104 can operate in a networked environment 200 using logical connections to one or more remote computers and/or devices. For example, the image processing and analysis 104 can operate in a networked environment 200 using logical connections to one or more MRI acquisition systems 102. Communications may be via a wired and/or wireless network architecture, for instance, wired and wireless enterprise-wide computer networks, intranets, extranets, and/or the Internet. Other embodiments may include other types of communications networks including telecommunications networks, cellular networks, paging networks, and other mobile networks. There may be any variety of computers, switching devices, routers, bridges, firewalls and other devices in the communications paths between the image processing and analysis systems 104, the MRI acquisition systems 102.

The MRI acquisition systems 102 will typically take the form of an MRI machine 108 and one or more associated processor-based devices, for instance an MRI control system 126 and/or MRI operator's system 128. The MRI acquisition systems 102 capture MRI information or data sets from patients. Thus, in some instances the MRI acquisition systems 102 may be denominated as front end MRI acquisition systems or MRI capture systems, to distinguish such from the MRI image processing and analysis system(s) 104, which in some instances may be denominated as MRI backend systems. The MRI acquisition systems 102 will at times each be referred to in the singular herein, but this is not intended to limit the embodiments to a single MRI acquisition system 102. In typical embodiments, there may be more than one MRI acquisition system 102 and there will likely be a large number of MRI acquisition systems 102 in the networked environment 200.

The MRI acquisition systems 102 may be communicatively coupled to one or more server computers (not shown). For instance, MRI acquisition systems 102 may be communicatively coupled via one or more diagnostic facility server computers (not shown), routers (not shown), bridges (not shown), LANs 106a (FIG. 1), etc., which may include or implement a firewall 156a (FIG. 1). The server computers (not shown) may execute a set of server instructions to function as a server for a number of MRI acquisition systems 102 (i.e., clients) communicatively coupled via a LAN 106a at a clinical facility or site, and thus act as intermediaries between the MRI acquisition systems 102 and the MRI image processing and analysis system(s) 104. The MRI acquisition systems 102 may execute a set of client instructions to function as a client of the server computer(s), which are communicatively coupled via a WAN.

The MRI control system 126 typically includes one or more processor (e.g., microprocessors, central processing units, digital signal processors, graphical processing units) and non-transitory processor-readable memory (e.g., ROM, RAM, Flash, magnetic and/or optical disks). The MRI operator's system 128 may take the form of a computer, for instance personal computers (e.g., desktop or laptop computers), net book computers, tablet computers, smart phones, personal digital assistants, workstation computers and/or mainframe computers, and the like, executing appropriate instructions.

The MRI operator's system 128 may include one or more processing units 268, system memories 269 and a system bus (not shown) that couples various system components including the system memory 269 to the processing unit 268.

The processing unit 268 may be any logic processing unit, such as one or more central processing units (CPUs), digital signal processors (DSPs), application-specific integrated circuits (ASICs), field programmable gate arrays (FPGAs), graphical processing units (GPUs), etc. Non-limiting examples of commercially available computer systems include, but are not limited to, an 80×86 or Pentium series microprocessor from Intel Corporation, U.S.A., a PowerPC microprocessor from IBM, a Sparc microprocessor from Sun Microsystems, Inc., a PA-MSC series microprocessor from Hewlett-Packard Company, a 68xxx series microprocessor from Motorola Corporation, an ATOM processor, or an A4 or A5 processor. Unless described otherwise, the construction and operation of the various blocks of the MRI acquisition systems 102 shown in FIG. 2 are of conventional design. As a result, such blocks need not be described in further detail herein, as they will be understood by those skilled in the relevant art.

The system bus can employ any known bus structures or architectures, including a memory bus with memory controller, a peripheral bus, and a local bus. The system memory 269 includes read-only memory ("ROM") 270 and random access memory ("RAM") 272. A basic input/output system ("BIOS") 271, which can form part of the ROM 270, contains basic routines that help transfer information between elements within the MRI acquisition systems 102, such as during start-up.

The MRI operator's system 128 may also include one or more media drives 273, e.g., a hard disk drive, magnetic disk drive, WORM drive, and/or optical disk drive, for reading from and writing to computer-readable storage media 274, e.g., hard disk, optical disks, and/or magnetic disks. The nontransitory computer-readable storage media 274 may, for example, take the form of removable media. For example, hard disks may take the form of a Winchester drive, and optical disks can take the form of CD-ROMs, while magnetic disks can take the form of magnetic floppy disks or diskettes. The media drive(s) 273 communicate with the processing unit 268 via one or more system buses. The media drives 273 may include interfaces or controllers (not shown) coupled between such drives and the system bus, as is known by those skilled in the relevant art. The media drives 273, and their associated nontransitory computer-readable storage media 274, provide nonvolatile storage of computer readable instructions, data structures, program modules and other data for MRI acquisition system(s) 102. Although described as employing computer-readable storage media 274 such as hard disks, optical disks and magnetic disks, those skilled in the relevant art will appreciate that MRI operator's system(s) 128 may employ other types of nontransitory computer-readable storage media that can store data accessible by a computer, such as magnetic cassettes, flash memory cards, digital video disks ("DVD"), Bernoulli cartridges, RAMs, ROMs, smart cards, etc. Data or information, for example, electronic or digital files or data or metadata related to such can be stored in the nontransitory computer-readable storage media 274.

Program modules, such as an operating system, one or more application programs, other programs or modules and program data, can be stored in the system memory 269. Program modules may include instructions for accessing a Website, extranet site or other site or services (e.g., Web services) and associated Webpages, other pages, screens or services hosted or provided by the MRI processing and analysis system(s) 104.

In particular, the system memory 269 may include communications programs that permit the MRI acquisition system(s) 102 to exchange electronic or digital information or files or data or metadata with the MRI image processing and/or analysis services provided by the MRI processing and analysis system(s) 104. The communications programs may, for example, be a Web client or browser that permits the MRI acquisition system(s) 102 to access and exchange information, files, data and/or metadata with sources such as Web sites of the Internet, corporate intranets, extranets, or other networks. Such may require that an end user client have sufficient right, permission, privilege or authority for accessing a given Website, for example, one hosted by the MRI processing and analysis system(s) 104. As discussed herein, patient identifying data may reside on systems operated by or for the clinical facility, and may not be accessible by or through the systems operated by or for the image processing facility or the image processing facility personnel. The browser may, for example, be markup language based, such as Hypertext Markup Language (HTML), Extensible Markup Language (XML) or Wireless Markup Language (WML), and may operate with markup languages that use syntactically delimited characters added to the data of a document to represent the structure of the document.

While described as being stored in the system memory 269, the operating system, application programs, other programs/modules, program data and/or browser can be stored on the computer-readable storage media 274 of the media drive(s) 273. An operator can enter commands and information into the MRI operator's system(s) 128 via a user interface 275 through input devices such as a touch screen or keyboard 276 and/or a pointing device 277 such as a mouse. Other input devices can include a microphone, joystick, game pad, tablet, scanner, etc. These and other input devices are connected to the processing unit 269 through an interface such as a serial port interface that couples to the system bus, although other interfaces such as a parallel port, a game port or a wireless interface or a universal serial bus ("USB") can be used. A display or monitor 278 may be coupled to the system bus via a video interface, such as a video adapter. The MRI operator system(s) 128 can include other output devices, such as speakers, printers, etc.

The MRI image processing and analysis system may build a static interface, which allows various tissue types to be subtracted or added to an MRI 4-D flow data set. For example, static tissues such as fat or bone may be distinguished from non-static tissues such as air or flowing blood. The MRI image processing and analysis system may further autonomously distinguish between various non-static tissues, for instance distinguishing between air (e.g., lungs) and flowing blood. Further, the MRI image processing and analysis system may distinguish between arterial and venous blood flows.

For instance, the MRI image processing and analysis system may employ fast Fourier transformation to identify blood tissue, which is expected to have a pulsatile pattern or waveform. Air or lung will tend to have a random appear pattern over a defined volume, as velocity of neighboring voxels are compared. For instance, voxels with strong or fast velocities are typically indicative or air. The MRI data sets may be rather large, for example 256×256×256×20 time points. The MRI image processing and analysis system may rely on gradients (e.g., gradient descent method) to detect different tissue types, and may advantageously employ a numerical approach rather than an analytic solution approach to quickly handle the relatively large MRI data sets. By controlling the number of significant digits (e.g., 2) of the numerical approach, the MRI image processing and analysis system may achieve very fast (e.g., 1 second as opposed to 30 minutes) results, while still obtaining results that are sufficiently accurate for the particular application.

In some implementations, different tissue types may be subtracted from the patient MRI data set, one at a time. For example, subtracting air or lung, subtracting blood, separating atrial from venous flow, subtracting bone, leaving fat. Notably, fat is static, so each voxel representing fat should have zero velocity associated therewith. The MRI image processing and analysis system may advantageously employ such a ground truth to correct MRI data set for all tissue types.

If a non-zero velocity is found for fat type tissue, this can be used to adjust the entire set of data (e.g., for all tissue). For example, the MRI image processing and analysis system may generate or create a polynomial model based on an identified area or volume (e.g., fat or soft tissue). Such may be a simple polynomial (e.g., $ax^2+bx+c$) or a much more complex polynomial (e.g., non-rational uniform b-spline). The MRI image processing and analysis system may find the coefficients to the polynomial fits the image, for example using linear regression techniques or linear algebra techniques. This results in a model which the MRI image processing and analysis system may apply to (e.g., subtract from) the whole field, not just the fat or soft tissue.

In one implementations, a replica body is imaged to create a reference set of data or "phantom" model which can be subtracted from actually patient data. The replica body may be formed of materials that mimic the MRI response of an actually body, although will not have blood flow. A phase gradient in reference set of data or "phantom" model may represent noise (e.g., random noise), and can be used to correct a phase shift. This approach advantageously avoids the need to generate a polynomial fit to the 3-D data. The generated reference set or phantom model may be valid over a number of months of MRI machine operation, although a new set of reference data or phantom model should be generated if the MRI machine is serviced or moved.

The MRI image processing and analysis system may define various filters or mask for removing different tissue types or for removing either venous or atrial blood flow. Filters or masks may remove anomalous blood flow, such as blood flow outside some reasonable range (e.g., too high or fast, too slow or low) or where blood appears to be flowing in an anatomical structure (e.g., bone) where there should be no blood flow. A filter or mask may also be defined to display only voxels having magnitudes with an absolute value greater than some threshold value. A filter or mask may also be defined to display only voxels with an absolute value of the cross product of magnitude and a velocity vector which absolute value is greater than some defined threshold. Further a filter or mask may be defined that shows only voxels having vectors in a same direction as the vectors of neighboring voxels, to for instance identify or view high velocity jets. Notably, velocity vectors of neighboring voxels are in different directions may be an indication of noise.

Pre-Processing
Mass Conservation Correction Error Reduction

The goal of this pre-processing algorithm is to correct the flow data (segmentation, flow quantification, and background phase error correction). There are 3 flow datasets that need to be corrected: i) x velocity, ii) y velocity, and iii) z velocity. Due to imaging artifacts (e.g., turbulence) and noise, the flow data will be biased. To correct for this, mass conservation (i.e., physical principles) is used to correct the flow data. Mass conservation tells us that the mass of a closed system must remain constant over time, as system mass cannot change quantity if it is not added or removed. Therefore, if a boundary is defined within the heart (i.e., luminal border of the heart chambers and vessels), the flow entering a stationary volume must match the flow exiting the volume if the fluid is incompressible. This theory can be applied to any volume. In the case of blood flow, we make assumptions that the blood density is constant, and therefore the continuity equation simplifies to mean that the divergence of velocity field is zero everywhere. Physically, this is equivalent to saying that the local volume dilation rate is zero (i.e., $du/dx+dv/dy+dw/dz=0$). It is impossible to force this condition everywhere, but the local volume dilation can be minimized over all time points. There are several different types of algorithms that will minimize $du/dx+dv/dy+dw/dz$, but the most common is an algorithm that will generate a least squares divergence free approximation of the flow field. There are several ways to construct a least squares approximation to the flow field with the constraint of minimizing the divergence, and several different algorithms to achieve this.

Typically there is an iterative approach involved that tries to minimize the residual divergence with every pass. In addition, knowing the exact boundary of the vessel/chamber is important to ensure zero flux through the boundary. Without said boundary, flow could be allowed to escape into the heart muscle and fat. In addition, there could be artifact in the image (i.e., caused by turbulence). If a user identifies a region where there is artifact ("bad data"), this region is not used to influence the velocity value correction in the "good data" region.

Another approach to solve this is using optimization: attempting to minimize divergence while ensuring the original vector field is changed as little as possible (to still capture local effects and prevent smoothing).

Conservation of momentum can be applied in a later act to estimate pressure gradients across a vessel in addition to wall shear stress. This mass conservation step is critical to ensure accurate pressure estimations.

Automatic Phase Aliasing Correction Using Time Domain

Phase aliasing occurs when the VENC that was set for the 4-D flow scan was too low causing the velocity values to "wrap"; from large positive values to large negative values or vice versa. In principle, this wrapping can happen more than once.

By analyzing the overall time variation of velocity data it is possible to determine the main points of the cardiac cycle (described elsewhere). Under the assumption that there is no velocity aliasing in the image at peak diastole and also under the assumption that velocity at a single point in space does not, in reality, vary by more than +/−VENC from one time point to the next, one is able to correct for phase aliasing by examining the time variation of each point in space as follows:

i) Identify the peak diastole time point and assume that there is no phase aliasing at that point.

ii) Examine the time behavior of each acquired velocity component individually.

iii) For each point in space (voxel) in each velocity image track the change in velocity from one time point to the next. If the velocity is observed to vary by more than +/−VENC assume that aliasing has occurred.

iv) When aliasing is detected the wrap count for that point is either incremented if observed velocity reduced by more than VENC or decremented if the observed velocity increased by more than VENC.

v) At each point in time the velocity is altered according to the current accumulated wrap count for that point by adding the product of wrap count with two times VENC.

vi) Check that wrap count has returned to a value of zero once the current time point has return to the initial peak diastole starting point. If wrap count has not returned to zero, then the processing of that point in space (voxel) should be considered to be an error.

The method can be improved and made more performant by using other methods to determine the pixels of interest. For example, one may use other methods to determine the pixels that are most likely to represent blood flow and only process these pixels.

This method also has the characteristic and advantage of being self-diagnosing. The wrap count for all valid blood voxels (as opposed to air, for example) should return to zero when the processing for that voxel over time has finished. Errors can be kept track of on a voxel by voxel basis though this has the weakness that this method of error detection is not guaranteed to catch every error voxel. However, in addition, by looking for a low overall error rate as a fraction of the number of pixels where corrections were applied, one can ascertain whether or not the necessary initial assumptions, required by the method, are largely correct.

Automatic Phase Aliasing Correction

Phase aliasing occurs when the VENC that was set for the 4-D flow scan was too low. It is very easy to find voxels that have been aliased because of the following:

i) The VENC of each scan is known since this information is in the header file of all the DICOM images.

ii) Identify sharp changes in flow velocity around the +/−VENC velocity (i.e., if VENC is set at 100 cm/s, look for sharp changes in velocity around +/−99 cm/s.) Sharp changes in velocity means a voxel may have a velocity value of 100 cm/s, and the adjacent voxel has a value of −99 cm/s.

iii) Then find the border of the aliased region by connecting all the voxels that have a sharp gradient around +/−VENC.

iv) This results in an enclosed boundary. Determine if all the voxels in the region of the enclosed boundary are aliased.

By starting at the boundary and moving toward the centroid of the 3-D region, the system can interrogate every voxel to ensure that there is no significant jump (across a VENC).

v) If no steep jump is encountered then the VENC velocity can be added to all voxels within the aliased region.

vi) If a steep jump is encountered, then the problem becomes a little more challenging (but still solvable). In this case, a voxel could be wrapped several times (i.e., if the VENC is set at 100 cm/s but the velocity at the voxel actually is 499 cm/s, this will be wrapped 2 times and the velocity will be shown as 99 cm/s). The way to correct the data is to look at the velocity of neighboring voxels. If there is a jump of more than 1.5 times the VENC, then 2*VENC needs to be added or subtracted in that enclosed region. The selection of adding or subtracting is chosen to minimize the discontinuity across the neighboring voxels.

vii) To improve the algorithm further, information about where static tissue is can be critical in defining where absolute zero must be. Since static tissue has 0 velocity, those voxels that are identified as being static tissue must not be wrapped. There then must be a continuous increase in speed away from the wall due to physical properties (i.e., fluid boundary layer). The only assumption in all of this is that neighboring voxels do not have more than a 1.5*VENC jump across one another.

Spline Real-Time Eddy Current Correction

When an MRI acquisition is performed the data can contain artifacts due to eddy currents in the magnetic field. In a 4-D flow acquisition in which particle velocity is acquired the artifacts will cause the velocity values to be incorrect. It is critical with 4-D flow to have accurate velocity data in order to quantify blood flow through vessels.

At least one technique for correcting the eddy current artifacts involves:

volumetric segmentation of static (zero velocity) tissues; and using the velocity data at these static locations to fit a curve to the volume that can be subtracted from the raw data.

Given a volume mask that represents the static tissue, 3-D blocks of arbitrary size are evaluated.

If a block within the volume contains enough masked voxels it is considered static tissue. The average velocity for each of the static tissue blocks is then used as control values for a collection of spline functions in each of the three primary axis directions. After evaluating all the spline functions in all three directions, the result is a regular grid of values that can be up-sampled to the original resolution and then subtracted from the original data. After subtraction, the static tissues should have an effective velocity of zero, and the non-static tissues will have eddy current artifacts removed. This will allow for accurate flow quantification.

Given a segmented volume, a new volume of significantly lower resolution was generated. The values in this new volume are the result of averaging values from the larger volume, however since some of the elements would be masked away by the segmentation, an element in the low-resolution volume might have significantly less high-resolution data and potentially no high-resolution data. Elements with no data or insufficient data are thrown out. The result at this point is a regular grid with holes in it. In order to evaluate the tensor product for the spline volume the initial pass evaluates spline basis functions for each row of elements wherein the order of the spline may vary due to the number of available control values. After the first pass, there will be no holes so the remainder of the tensor product can be evaluated. Based on the analysis of our test data, results from this new and innovative approach is a smooth 3-D time-varying function representing the error in the volume and is very fast to calculate.

For the third step, our approach to apply the correction algorithm was to use tri-linear sampling from the correction volume, which proved successful. For each element in the source volume we perform a tri-linear blend of eight elements in the correction volume and subtract that value from the source data. After applying our new correction function flow measurements were found to be within 3% error. In addition, as part of the process requires user interaction, the requirement for real-time performance was also met as evaluating and applying our new correction takes on the order of milliseconds instead of hours.

Solids for Background Phase Error Correction

The blood velocity information in the 4-D flow MRI scan has an error which needs to be corrected for in order to get accurate blood flow calculations. The error signal in the static tissue can be used to provide a correction function for the non-static tissue (described elsewhere). A three-dimensional volume of tissue called a solid can be created to identify a section of either static or non-static tissue. A solid can be created using two methods:

Orthogonal contours: The user can manually draw three intersecting closed contours. The intersection of these contours represents a solid, three-dimensional volume of either static or non-static tissue. The contours do not need to be perfectly orthogonal and the user can create the contours at any location.

3-D floods: The user can alternatively choose to automatically create a solid by specifying the starting point of a three-dimensional flood. The flood can be used on any image including phase images. The image is flooded based on a threshold below and above the value at the point where the user clicked. The user can control both the threshold and the radius of the flood that is generated.

Multiple solids can be created using either method to mask out areas of both static and non-static tissue and can be used overlapping each other to unmask areas within an existing solid.

In some situations there will be artifact in the images. Artifact needs to be removed or highlighted in order to prevent a user from giving an incorrect diagnosis. Our software has pre-processing steps (i.e., eddy current correction) that compute a metric based on all of the voxels in the dataset. To avoid these pre-processing steps a tool is used to identify voxels that have artifact, and these voxels are removed from any pre-processing step (but not removed for visualization purposes). The tool can be a manual segmentation tool (i.e., user circles areas that have artifact), or a semi-automatic/automatic segmentation tool that identifies artifact. Regardless of the tool specifics our software needs a feature to remove "bad voxels" from being quantified.

Automatic Background Phase Error Correction

Accurate measurement of velocity in 4-D flow MRI scans requires the application of corrections for the false signal introduced by eddy currents. Determining eddy current correction (ECC) is done by examining the velocity signal in static (non-moving) tissue. This requires the masking of all moving tissue, blood and air. This claim describes a method for doing this automatically, without user intervention. Automatic correction is useful as it not only makes the software simpler and quicker to use, it allows the correction to be precomputed and applied when the user first opens the study. It is also very important as it allows other preprocessing algorithms, doing things like automatic segmentation and measurement, to benefit from ECC.

Automatic ECC is done by computing initial starting values for three filters that the user is then free to adjust after the study is open. Air is masked by masking out regions with anatomy image values below a set threshold. This threshold is determined automatically by an analysis of the histogram for anatomy image values over the entire scanned volume. The histogram for these values over the chest cavity displays a pattern that allows for the automatic detection of the image values corresponding to air.

In addition, two filters have been developed that reliably detect regions of blood flow and regions of heart wall movement. The region of the heart can be satisfactorily masked out by appropriately setting these two filters. Due to the normalization used in the production of these filters along with their naturally consistent nature, satisfactory results can be obtained simply by setting these filters to predetermined values (for example, 50%). The automatic setting of these filters could be further improved (or tweaked) by analysis of the values produced by these filters, similar to what was described in the previous paragraph for the detection of regions of air. The settings could also be tweaked by examining the resulting ECC and looking for regions that show large variation over the cardiac cycle.

The correct values for these filters, determined when the study is preprocessed, are then simply stored in the database along with the other study information, allowing the client software to set these as the default values when the study is first opened.

Visualization

Temporal Landmark Quantification and Visualization

It useful to be able to identify landmarks (i.e., points, lines, planes, areas, volumes) in the body and specifically in the heart. Several landmarks are dynamic in nature (e.g., mitral valve plane), and thus it is important to track their movement in time:

Points: Track 3-D path (which is a line) over time.

Lines: Track 3-D path of 2 endpoints over time.

Planes: Track a point on a plane and the plane's normal vector over time.

Areas: Track dilating contour, contour centroid, and contour normal vector over time.

Volumes: Discretize surface of volume and track each discretized point over time.

There are two acts to temporal landmark quantification and visualization:

1) Detection: The first step is to identify the landmarks over time. This can be done manually or automatically.

Manual detection: The user can indicate the position and orientation of each landmark. One method of doing this could be to navigate the image using pan and rotate so that the center of the image is at the desired location of the landmark. The location of the landmark can be different at different points in time and it will be interpolated for timepoints where the user has not explicitly set it. It is indicated to the user if a landmark is interpolated.

2) Display: Depending on the type of landmark a different type of method to display the data is used. For instance if a contour does not move or change its normal vector over time (i.e., just dilate), it makes sense for the user's view plane to not change and always be aligned with the contour. If this contour does move, we can imagine following the plane such that the view is always aligned with the plane for each time point. The view plane can be either from a Lagrangian perspective or from an Eulerian perspective. For volumes, an Eulerian perspective is more appropriate where the surface of a volume dilates and this can be visualized with a camera that is fixed in space (the user can change the camera location as needed).

Cardiac views: The left ventricle apex, right ventricle apex, mitral valve, tricuspid valve, aortic valve, and pulmonic valve can be used to create two-chamber, three-chamber, four-chamber, and short-axis views of both the right and left ventricles once the landmarks have been detected. The orientations of these views are specified in the Mayo Clinic Guide to Cardiac MR. An orientation and zoom level for each view can be calculated from the positions of the landmarks. If the landmark's position changes in time the view will change in time accordingly.

Example landmarks for each view:

Left two chamber: aortic valve, mitral valve, tricuspid valve, left ventricle apex Left three chamber: aortic valve, mitral valve, left ventricle apex Left four chamber: tricuspid valve, mitral valve, left ventricle apex Left short axis: mitral valve, left ventricle apex Right two chamber: pulmonic valve, tricuspid valve, mitral valve, right ventricle apex Right three chamber: pulmonic valve, tricuspid valve, right ventricle apex Right four chamber: tricuspid valve, mitral valve, right ventricle apex Right short axis: tricuspid valve, right ventricle apex Interactive Landmark Based Views Once certain landmarks have been placed (e.g., aortic valve, mitral valve, left ventricle apex, anterior papillary muscle, posterior papillary muscle, pulmonary valve, tricuspid valve, right ventricle apex, LPA, RPA, SVC, IVC, descending aorta), automatic views can be created to display the anatomy of interest. Clinicians are used to viewing a certain landmark with 3 perpendicular views or in the case of the heart using a 4 chamber view or a left or right ventricle 2 or 3 chamber view. By updating the location of just 1 landmark for one of the time points, all views update accordingly such that either the views are always perpendicular or the 2, 3, and 4 chamber views remain intact. Once the landmarks have been placed, and the views generated automatically, these views can be saved in the report section of the software and exported in any format (i.e., an image) include a cine movie (i.e., multiple images over time).

4-D Mesh Creation from Closed Contours

Once contours have been placed along the short axis (possibly curved) for each time point, the mesh is then generated independently for each time point. This is done by rotating each contour in the short axis stack so as to minimize twisting, and then generating open cubic spline which connects the first point in each contour, a second spline that connects the second point, so on for each point in the contour (each slice's contour has the same number of points. The result of this process is a cylindrical grid of points which we use as the vertices of the mesh.

The process of minimizing twisting is done by computing an open cubic Hermite spline from the centroid of one contour to the centroid of the contour above, and then running this spline from each point on the lower contour until it intersects the plane the contour above it lies in. The system computes this intersection point and then determines which of these intersection points lies closest to an actual contour point in the upper contour. The contour is then rotated such that these two points will lie on the same long axis spline.

The current implementation works reasonably well with both curved and straight axes when the contours are reasonably circular and the difference between neighboring contours spatially is minimal. However, in the case of the right ventricle where the contours are not circular, excessive twisting is sometimes introduced by the current implementation. To minimize this, we should get rid of the long axis spline approach and switch to one where the number of triangles between any two slices may differ. Doing this minimizes twisting more locally which will result in an overall smoother mesh.

Snap to Flow Tool

Accurately observing or measuring the blood flow in a 4-D flow scan requires the user to align an MPR so that it is perpendicular to the direction of flow. This describes a method for creating a tool allowing the user to set the correct orientation of the MPR automatically.

In order to align an MPR the user first activates the tool and then clicks on a central region of the blood flow in question. The click points then serves as the center of rotation when the MPR is aligned, moving the click point to the center of the resulting MPR. Alignment is done by averaging the blood flow in a small region around the click point. To do this accurately, the measurement is done using the timepoint corresponding to peak blood flow, regardless of the timepoint that the user is currently viewing while using the tool. This generally implies doing the measurement at peak systole.

While the user is allowed to adjust the timepoint for peak systole, this point is first determined automatically by the executing software during preprocessing of the data set, and this automatic value is used as the default when the study is first opened by the user. A filter has been developed (described elsewhere) for automatically determining regions of blood flow within the scanned volume. Peak systole is then determined by examining the time dependence of the overall flow within the filtered or mask region determined to correspond to blood.

Once the direction of flow has been accurately determined it is straightforward to adjust the orientation of the MPR so that it is on a plane perpendicular to the flow.

Quantification

Automatic Blood Flow Quantification

The blood flow in a chamber and/or vessel can be automatically quantified by first isolating the blood pool (see segmentation methods described in this document) and placing a plane on a landmark (that can be defined using the methods above) that is roughly perpendicular to the flow in the chamber/vessel (i.e., normal of plane is aligned with the flow). Once these 2 acts have been achieved, the intersection between the plane and blood pool creates a contour. All the voxels within the contour are flagged. Next is to sum the dot product of the plane's normal vector with the velocity vector of that voxel (in addition to normalizing by the area of the voxel) for every voxel to give the total flow. The flow at that contour can be automatically displayed on screen or in report that could be eventually exported.

Allowing a user to select a position on an image has many important applications. In performing measurements a user might want to measure the distance from one point to another. In an application that uses MPRs from a volume of data, the points on an image represent locations in 3-D space. These 3-D points are easy to compute from the metadata associated with the image. In an application that uses volume rendering, allowing a user to select a point in 3-D space is more difficult since each pixel could be at a different depth.

In typical front to back volume raycasting with an increasing alpha compositing function that terminates once alpha reaches 1.0, determining the depth of the pixel can be done by keeping track of where the ray terminates. When raycasting back to front, there is no early ray termination. The result color is simply updated based on the compositing function. Typically the compositing function will make air transparent and as such the color will stop changing as the ray exits the material closest to the eye. By keeping track of when the color stopped changing, this depth for each pixel can be used to transform the 2-D user selected coordinate back into a 3-D location in space. This 3-D location selection can be used to select a blood vessel and then automatically quantify flow.

Automatic Shunt Detection

Instead of trying to find an exact location for a shunt, the first operation would be to identify if a shunt exists. One simple method of identifying if a shunt is present is to measure the left heart flow (Qs) and the right heart flow (Qp). Qp and Qs can be measured either manually (e.g., by placing a contour) or automatically if landmarks and blood pool segmentation have been completed. If these numbers do not match within a certain threshold, the scan can be flagged as potentially having a shunt.

These measurements could be done automatically using the following technique:

i) Automatic measurement of cardiac output (Qs) is described elsewhere as is the production of masks for both aortic and pulmonic flow along with automatic estimates of the location of the aortic and pulmonic valves.

ii) Once the valve regions have been identified, it is a straightforward task to take them and the already determined pulmonic flow regions, move slightly downstream from the valve and produce flow measurement contours in a similar way to what has been described for cardiac output. Once suitable contours have been identified for measuring pulmonic flow the existing flow measurement algorithms can be used to determine the output from the right ventricle.

iii) Use the automatic flow measurement to indicate the likelihood that a shunt exists.

Automatic Detection of Peak and End Systole and Diastole

Much automatic processing depends on the ability to first identify the timepoints corresponding to the main temporal landmarks in the cardiac cycle: peak and end systole and diastole.

As described elsewhere, we are able to use a Fourier analysis technique on the velocity images in order to identify regions of blood flow within the heart along with the main arteries and veins around the heart. Once these main regions of blood flow have been identified, we find the total blood flow over the identified voxels at each point in time (typically 20 timepoints). The system is then able to analyze the resulting function of time to determine the landmarks in the cardiac cycle. The timepoint with the most flow is first assigned the peak systole landmark. From there the function is analyzed in both directions in time to determine the points where the flow tends to level off. The point before peak systole where the total flow levels off (the point right before it starts to rise quickly) corresponds to end diastole. Following peak systole, the total flow drops quickly until it levels off, which corresponds to end systole. Peak diastole is not typically a well defined point so we place this temporal landmark at the point midway between end systole and end diastole.

Automatic Cardiac Output and Volumetric Measurements

Automatic measurement of cardiac output is done using the following method:

i) The relationship between the main DFT components of the velocity images, along with the already determined peak systole landmark (described elsewhere) are used to identify the main regions of arterial flow from the left and right ventricles.

ii) A variety of flow continuity filters is used, one after the other, to separate the arterial flow region into two pieces, aortic and pulmonic flow. The point in the initial arterial flow mask with the largest velocity provides a reliable point known to be in either the aorta or the pulmonary artery. Separation of the two regions of flow can be determined, for example, by examination of the size of the region within the resulting filter that can be flooded starting at the point of maximum flow. Once the first piece is identified, the second piece can be identified, for example, by flooding from the maximum flow point in the remaining regions.

iii) Once two regions have been identified one corresponding to aortic flow and one to pulmonic flow, the two regions can be allowed to grow back a limited amount (with individual pixels only being assigned to one mask or the other) and with the original arterial flow mask providing absolute limits to the amount of growth. Allowing at least a little dilation of the masks can also be very important as the preceding process operations may have put small holes in the resulting regions that would tend to hinder the next steps in the method.

iv) The two flow regions can be identified as aortic and pulmonic flow based on their spatial relationship to each other and their very different expected shape and orientation in space. Once this is done the original arterial flow mask is essentially divided into two regions, one labeled aortic flow and the other labeled pulmonic flow.

v) As the aorta is essentially one continuous pipe, the path of the aorta can be traced from a starting point within the artery until the two ends are reached. At each point the main peak systole flow direction can be determined by averaging over a small region around the point. Orthogonals to the flow direction can then be projected from the starting point at regular angular intervals to determine the boundary with the masked aortic region, thus determining an approximately circular contour around the starting point.

vi) Once a contour has been determined as a polygon on the plane orthogonal to the main flow direction for some starting point. The starting point is re-centered in the polygon. At this point a small step (for example, one millimeter) can be taken from the center point in the positive or negative flow direction, depending on which way from the starting point we are tracing, and the process then repeated. This is continued until we step out of the mask at each end.

vii) Once contours have been produced at regular intervals along the aorta, essentially producing a mesh, they are refined at each individual timepoint using either the anatomy images (possible if dealing with a blood flow enhanced dataset) or by using through velocity for the systole timepoints and interpolation between. One possible approach is to use a snake algorithm to accurately identify the desired boundary for each contour at each point in time.

viii) Once refined contours have been determined, the major and minor diameters of each contour are measured, the major diameter being the largest diameter and the minor diameter being the largest diameter orthogonal to the major diameter.

viii) The next task is to identify good contours in the main region of the ascending aorta between the aortic valve and the bifurcations that occur at the top of the aorta, as this is the region that needs to be used when measuring cardiac output. This can be done in a number of acts. First, ascending aorta regions are easily separated from descending regions by flow direction. The remaining contours can then be scored using a combination of the continuity and variability of the contour area and diameters (major and minor) both spatially (along the aorta) and temporally at one point in the aorta. Scores can be averaged along the aorta to look for regions of good scoring as opposed to simply identifying individual, highly scored, contours. Using this method, one can eliminate regions in the neighborhood of the bifurcations at the top of the aorta and also regions that might exist near the aortic valve and on into the left ventricle, as these regions, by their nature, will score badly.

ix) Once good regions of the ascending aorta have been identified, the highest scoring individual contours can be selected for the actual cardiac output measurement. If possible, measurement is done at multiple points along the ascending aorta, which improves the result through averaging along with providing automatic determination of the quality of the measurement by examining the variability (thereby, also providing estimates of the measurement uncertainty). In addition, examining the result of multiple measurements of the flow along the ascending aorta allows for a judgement on the quality of the velocity eddy-current-correction that is currently being applied.

x) Once the ideal contours have been selected along the ascending aorta, cardiac output is determined by the usual flow measurement techniques.

4-D Volumetric Measurement

In order to calculate the volume of a particular region, we have developed three options within the Arterys cloud interface.

Option 1: Fixed Axis

Two points in 3-D space define the primary axis of a volume of interest. A straight line connects these 2 points (i.e., fixed axis). The axis is then divided into discrete points (say 2~40 for example) that define the locations where a slice will be placed. Slices are aligned orthogonal to the axis such that they do not intersect. Slices do not have to be evenly spaced. An MPR is rendered at all slice locations to allow a user to see what the medical image looks like at that slice location. Then either manually or automatically a closed contour is created on every slice to define the boundary of the volume at that slice location. There could be multiple closed contours at every slice location. There could also be no contours at all on one or more slices. In the case of 4-D or higher dimensional studies (i.e., studies that show volume change, or said different, multiple frames per slice), there can be separate contours per frame. Once all contours have been placed for all frames and slices, a 3-D surface is created connecting the contours of all slices for a particular frame. The way the 3-D surface is created from a set of closed contours is explained above in "4-D Mesh Creation from Closed Contours". If there is a 4-D or higher dimensional volume, a change in volume can be calculated by computing the volume of each frame and subtracting it with another frame. This is especially important when trying to quantify ventricular function which then gives stroke volumes and ejection fractions.

Option 2: Moving Straight Axis

This method is similar to Option 1, except that in the case of a 4-D volume, the landmarks or points that define the two endpoints of the axis can move over each frame (e.g., timepoint). This causes the volume to potentially move locations in 3-D space without changing volume.

Option 3: Fixed Curved Axis.

This method is similar to Option 1, except that the line connecting the 2 endpoints does not have to be straight. This line can be curved or have multiple straight and curved sections. This is handled in the system with a spline that connects points/locations between 2 endpoints. These points/locations can be anywhere and not necessarily always between the 2 endpoints.

Option 4: Moving Curved Axis

This method is similar to Option 2, except that in the case of a 4-D volume, the landmarks or points that define the two endpoints of the curved axis can move over each frame (e.g., timepoint). This causes the volume to potentially move locations in 3-D space without changing volume.

In all of the options above, there could be multiple axes. For example there could be a "Y" shaped axis that splits in 2 from 1. There is also the option of having both straight and curved axes that split and come together to create the volume. The point of this would be to account for more complex shapes that still have a primary axis (i.e., centerline).

In all of the options above, there is also the option of displaying how the 3-D volume intersects an MPR. The intersection must be a collection of one or more closed contours. These closed contours can be rendered on the MPR., In addition, these closed contours can be edited by moving the contour in the new (non orthogonal) view. The intersection contours can be computed both on the client as well as the server, or be adaptive depending on local resources. For cardiac imaging, common non-orthogonal views are 2, 3, and 4 chamber views. The contours can be edited in these views by only allowing the editing to be in a certain direction (i.e., along the slice plane).

Out of Plane Measurements and Tracking Mode

Measurements in a cardiac system from volumetric MRI data has several complexities. For example, the shape, position, orientation, and velocity of the valve plane can change significantly over a cardiac cycle. We solve this by using 2-D contours that move through 3-D space. Either manually or automatically, contours are placed at the border of the valve opening on the plane that is most perpendicular to flow direction. The position and orientation of the valve plane are tracked for each phase of the cardiac cycle. The evaluation of flow is performed through standard finite methods integration, however, in the event that the valve plane is moving the linear and angular velocity of the valve plane can be included in the flow computation for that phase. During visualization, when cycling through phases the position and orientation of the MPR can track with the valve plane. If a measurement is visualized when the current MPR is out of plane, the contour is rendered semi-transparent.

Segmentation

Continuity Equation Driven Segmentation of Blood Pool

Once again, mass conservation (i.e., continuity) with the incompressibility assumption can be used to show that divergence must be zero everywhere in the blood pool. By computing the divergence everywhere, the system can define the extents of the blood pool by a threshold divergence value. The divergence outside the blood pool will be larger (i.e., air in the lungs) or the velocity will be low (i.e., velocity signal in static tissue), which both help in identifying the lumen boundary. The divergence map does not need to be the sole input into a segmentation algorithm, instead it could added to other inputs and weighted appropriately.

Automatic Landmark Detection

The typical ways to create an automatic landmark detection algorithm is look for certain shapes in images and measure distances and angles between these shapes. If the measurements lie within a certain band they are classified. Several other physiologic inputs can be added to the algorithm. For instance locating a volume of fluid that increases and decreases substantially with every heartbeat (this is likely to be a ventricle). Once a ventricle is found, the inlet and outlet of the valve can be found by following streamlines. Once a valve is found, it is easier to find the remaining valves because they are typically always a certain distance and angle away from each other.

The algorithm that is selected to find the landmarks can be of the machine learning type. Since Arterys will be constantly collecting data that has been validated with correct landmark placing by a clinician this data needs to be used as a training set (e.g., statistical aggregation of data). Every dataset that needs to be analyzed can be co-registered with an 'atlas' that is built with the training set data. Once a sufficient number of datasets are collected, additional input parameters such as type of disease (i.e., healthy, tetralogy of Fallot, etc.) can be used to bin the datasets prior to be analyzed. Every bin could have slightly different landmarks and measurements depending on the type of disease and what pathology is expected. If it is known that a dataset is a patient that has a single ventricle, the automatic landmark detection algorithm needs to adjust for this as it will never find 4 valves.

In particular the aortic and pulmonic valve landmarks can be determined using the following process:

i) Identify regions corresponding to arterial flow from the left and right ventricle. Filters have been developed (described elsewhere) that are able to do this with high reliability.

ii) Separate the region of arterial flow into two regions, one corresponding to the aorta and one to the pulmonary artery. This process is described in detail under cardiac output.

iii) Once one region corresponding to either flow from the left or right ventricle has been determined, the other region is determined by subtracting from the starting region corresponding to both flows. The regions can then be easily identified as left ventricle flow or right ventricle flow based on their physical dimensions and orientations in space (also described under cardiac output).

iv) Once the two regions of flow have been identified, initial approximations for the location of the aortic and pulmonic valve can be determined by carefully tracing the bulk flow back to its apparent origin.

v) Once reliable initial estimates are produced for the location of the two valves, other techniques can be used to refine the valve location. For example, one could examine the blood flow acceleration and intensity in the region surrounding the initial estimate in order to refine the location of the valves.

Interactive 4-D Volume Segmentation

Segmentation of ventricles from a cardiac scan is critical to determining ventricular function. Automatic ventricular function technique may involve:

an input of two or more points representing control points of a spline;

the endpoints of the spline denote the apex of the ventricle and the exit valve (pulmonic or aortic);

using these points generate MPRs with plane normals set to the tangent of the curve at regular intervals along the spline curve;

on each MPR apply an active contour model to find the boundary (epicardium or endocardium) of the ventricle; and generate a 3-D mesh using the points of each of these contours.

Active contour models are subject to instability from the forces that act on them. To reduce this instability, instead of simply generating the contours such that they are spaced at the desired output spacing (distance between contours), the system generates many contours spaced very tightly together. Also, if the input data has temporal data, contours at the same location are generated using data from adjacent time points. Contour shape and quality is then measured against typical contours from a ventricle. If a contour is deemed to be of sufficient quality it is included in generating a final result. The final results are generated by averaging the included contours that are close to the position and time along the input curve. With a mesh constructed at both end systole and end diastole the difference in volume represents cardiac output and ventricular function.

In one example implementation, the Arterys system and software would provide single click 4-D volume segmentation. This would allow the user to click areas of interest (e.g., blood pool, myocardium, bone, etc.) while freely navigating (i.e., rotating, panning, zooming, slice scrolling, time scrolling) the 3-D volume. Since a full 3-D volume segmentation algorithm is challenging to construct and be accurate, a second option is to display 3 orthogonal views to the user while the user draws the boundary of the area the user would like to segment. For the heart, the view that is displayed can be a 2, 3, and 4 chamber view of the heart in addition to a short axis view. The user only needs to create 2 orthogonal contours in long axis, and then the software can automatically or autonomously create a 3-D surface based on interpolating the two contours. The 3-D surface can be shown in short axis to the user for quick modification. In addition to showing the anatomic images, the blood velocity images (with or without vectors) can be overlaid onto the anatomic images to further clarify where the blood pool boundary is during the interactive 3-D volume segmentation process.

Adaptive Flood Fill

The system makes use of multiple types of floods which may be distinguished as 2-D vs. 3-D, by connectivity used during the flood (6, 18, or 26 way connectivity), and radius constrained vs. a flood constrained by a maximum number of steps. In all cases, the flood works by moving outward from a specified seed point and including a pixel in the result of the flood if it is 1) connected to the rest of the flood (using whatever connectivity was specified), 2) has an intensity within a specified threshold of the pixel at the seed point, and 3) the pixel is within the specified radius of maximum number of steps of the seed point. The result of the flood is a two- or three-dimensional connected mask. The flood algorithm is used in solids in the form of a 3-D flood to mark static/non-static tissue, in volumes where a 2-D flood can be used to generate a contour in the short axis stack, and in flow quantification, where a 2-D flood may be used to flood a vessel to determine the flow contained within the flood.

To generate a contour from a radius-constrained 2-D flood, we make use of the fact that the flood will necessarily be connected and that it is a binary image. Because of these facts, we may apply a standard border tracing algorithm to come up with a contour which will ignore any holes that may be present within the interior of the flood.

From the generated contour, the next operation is to reduce the generated contour from potentially hundreds of points to a small set of control points to be used by a closed cubic spline to accurately approximate the actual contour. A naïve down sample where the system simply spaces a fixed number of control points spaced equally around the contour does not work as well as other approaches, as this approach frequently results in the loss of important features in the contour such as concave portion of the flood which was going around a papillary muscle. To get around this, a "smart" down sample approach is employed which proceeds in a number of acts. To begin with, each point in the contour is assigned a corner strength score ranging from −1 to 1, as well as assigning each point an area of "influence". Once this is done, the contour is reduced to only those points where their corner strength is maximal within their area of influence. Additional criteria are also enforced in this stage, such as ensuring we have a minimal point spacing and ensuring our detected corners are sufficiently strong. The result of the preceding operation is a list of "corners" detected in the flood. By using these as control points in a spline, this approach ensures that the spline will not lose any interesting features in the contour. However, any long stretches of relatively low curvature in the original contour will not be detected as corners, which can result in significant portions of the resulting contour not having any control points, leading to a poor approximation by a spline in such segments. To get around this, an error metric is computed for each pair of control points by calculating the area of a closed contour formed by the segment of the original contour passing through the points, and the segment of a spline passing through those points. If the error is above some fixed tolerance, another control point is added at the midpoint of the segment of the original contour. This operation is repeated until each segment has a computed error below the required tolerance.

This flood-to-contour tool is can be used in at least two places in the application: for flooding slices of a ventricle while performing a volumetric segmentation, and in flow quantification. In the case of the flood for volumes, the returned contour is dilated by 8% in order to capture more of the ventricle as a raw flood fill often underestimates simply because of the difference in pixel intensities close to the heart wall. For a flow flood, the result is dilated by 12% because the flood tool works on anatomy, which means the undilated flood will often miss flow near the vessel wall.
Overall Process
Automated Reports In a way similar to how echocardiographic reports are generated, an automated report based on 4-D flow MR data can be created by allowing the user to click on the type of patient they have. Arterys will have unique report templates that are specific to a certain pathology or type of user (i.e., patient or clinician). All of the values, curves, images, and cine movies in this report can be automatically populated in the report template. Since landmarks are placed as part of the pre-processing step, all the important information can be automatically saved in the database and exported to this report.
Automated Integration Tests A tool called node-webkit that is designed for making client side Web applications using node.js to perform automated integration tests. Although not designed for this purpose, it allows us to run both client and server software stack within the same environment allowing up complete control over the client and server applications at the same time. Using infrastructure mixed with a test tool called mocha, we write tests that emulate the customer interaction with the client while asserting both the client and server processing of that interaction along with the resulting state of the application. This method of integration testing is novel and superior to other tools that are mostly vision based, for this type of User Interface testing.
Hybrid Client Server Rendering Description Some workflows require one or multiple images to be rendered at the same time that have linked properties. In some cases the current workflow step may require simultaneous viewing of 20 images. If each of these images was retrieved with a distinct HTTPS request, performance would suffer greatly as there is significant overhead in creating and sending a request. Instead, we render all the images onto one large image, and only make a single HTTPS request for that 'sprite sheet'. The client then displays the images by using pixel offsets. For example, if a view had four images each 256×256, the sprite sheet might be 256×1024 with each of the images stacked one on top of another. The client would then display 4 images at 256×256 by using offsets of 0, 256, 512, and 768.

In addition, any lines, markers, or planes in the images are drawn on the client as an overlay, and the information that informs the client how to render the overlay comes from the server via a JSON message. This provides higher quality rendering of the overlay data than if the overlay were to be rendered on the server and then encoded as a JPEG and transmitted.
Automated Global Endurance and Stress Testing In order to perform load testing and endurance testing, we launch a multitude of client processes on a multitude of computers (which can be geographically distributed) to start specialized web browsers in which we have complete control over their execution environment. They are directed to the application and load the client as a normal browser would, then we directly interact with the client state controlling the software and making it behave as certain workload. The client and server metrics are recorded during load testing and run for longer periods of time for endurance testing.
Pusher Pushing Data from a Medical Device to Remote Servers We have developed software to monitor for active studies, and push the results to our remote service in the cloud. A folder is monitored for files being generated by a scanner, and upon completion, all relevant data is bundled together and pushed via a secure connection using a unique secret and key per scanner for authorization to our remote cloud servers. Disk space (e.g., nontransitory storage media) usage is minimized by immediately deleting any intermediate files.

Upon a successful transfer, the data integrity of the transferred content is verified against the local content by reproducing the package process and comparing the output of a cryptographic hash function. Repeating the process like this ensures that any new data that may have been generated by a scan was not missed in the case of delays during the scanning process which may trigger premature transfer of the data to Arterys servers.

In the case of a failed transfer, due to server or network errors a configurable number of attempts will be made with an increasing interval of rest between each attempt, before the pusher assumes the transfer was a failure. However, after a failed transfer (including all subsequent attempts), the pusher will continue to monitor for incoming files, and will re-attempt another transfer at a later time.

Once data has been verified as successfully transferred, the data is removed by our software to conserve disk space on scanners.

A heartbeat message is sent from each pusher software running on every scanner providing the local log data and detailed status information of the scanner, providing continuous monitoring and increased response time to ensure scanner functionality during critical scan times.

During initial installation, a scanner will automatically register with Arterys by requesting a unique secret and key to sign all future requests with for authorization purposes. The scanner will be registered in our systems database, but not attached to any organizations. A technician is then able to attach all recently registered scanners to the correct organization through a web portal.

A pusher is able to auto update (if configured) by periodically requesting new versions from Arterys. If a new version is provided, it will install a new copy of itself, and restart. This allows for security and functionality updates to be deployed to scanners with no intervention from technicians. The heartbeat messages provide the information required to ensure success of this operation on the Arterys servers. The heartbeats enable us to determine any pushers that have not been updated recently, and reach out to hospitals directly to proactively ensure all software is up to date and secure.

Figure 3A:
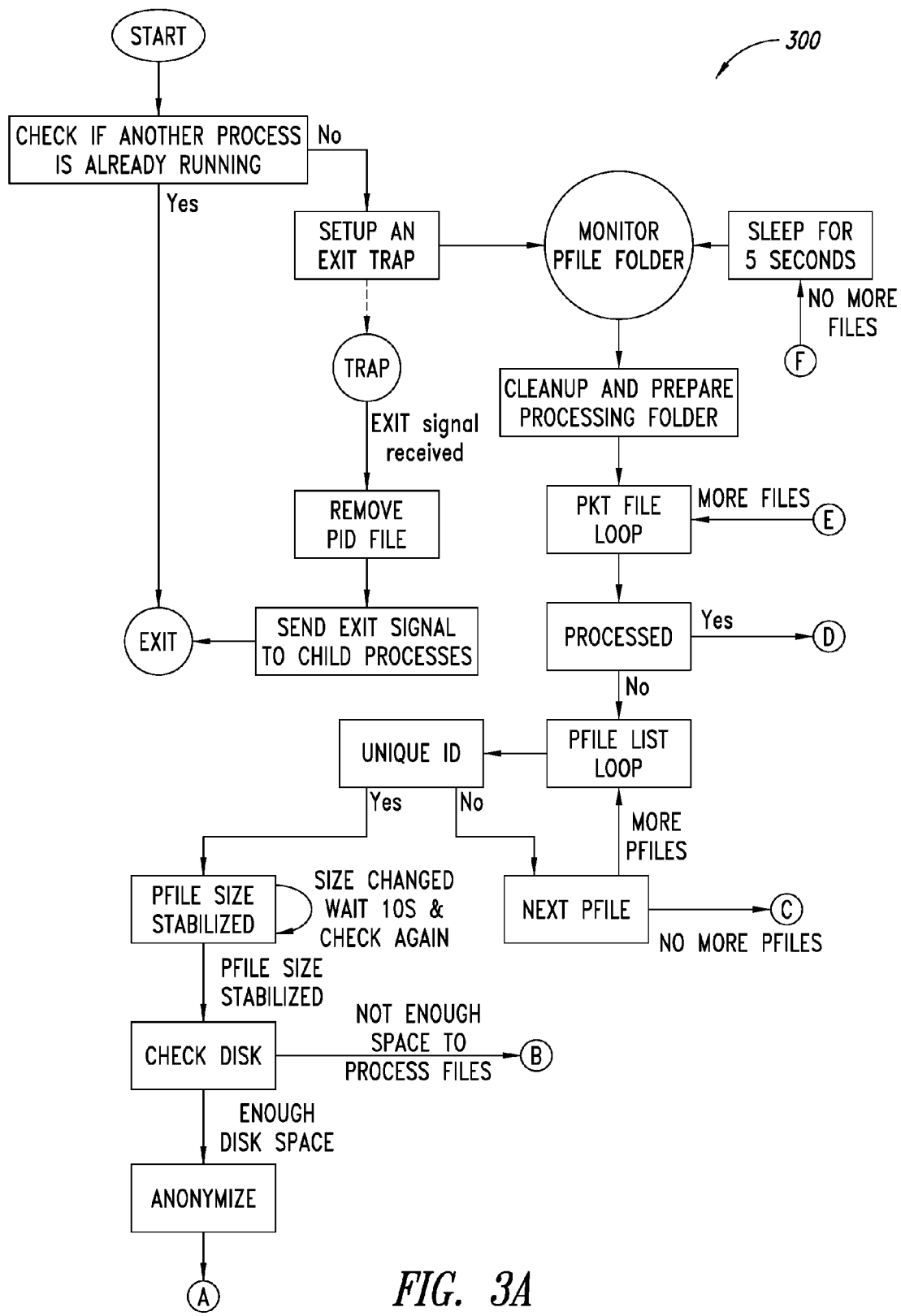
FIGS. 3A-3B are a flow diagram of an example push process executable by at least one processor, according to one illustrated embodiment.
Figure 3B:
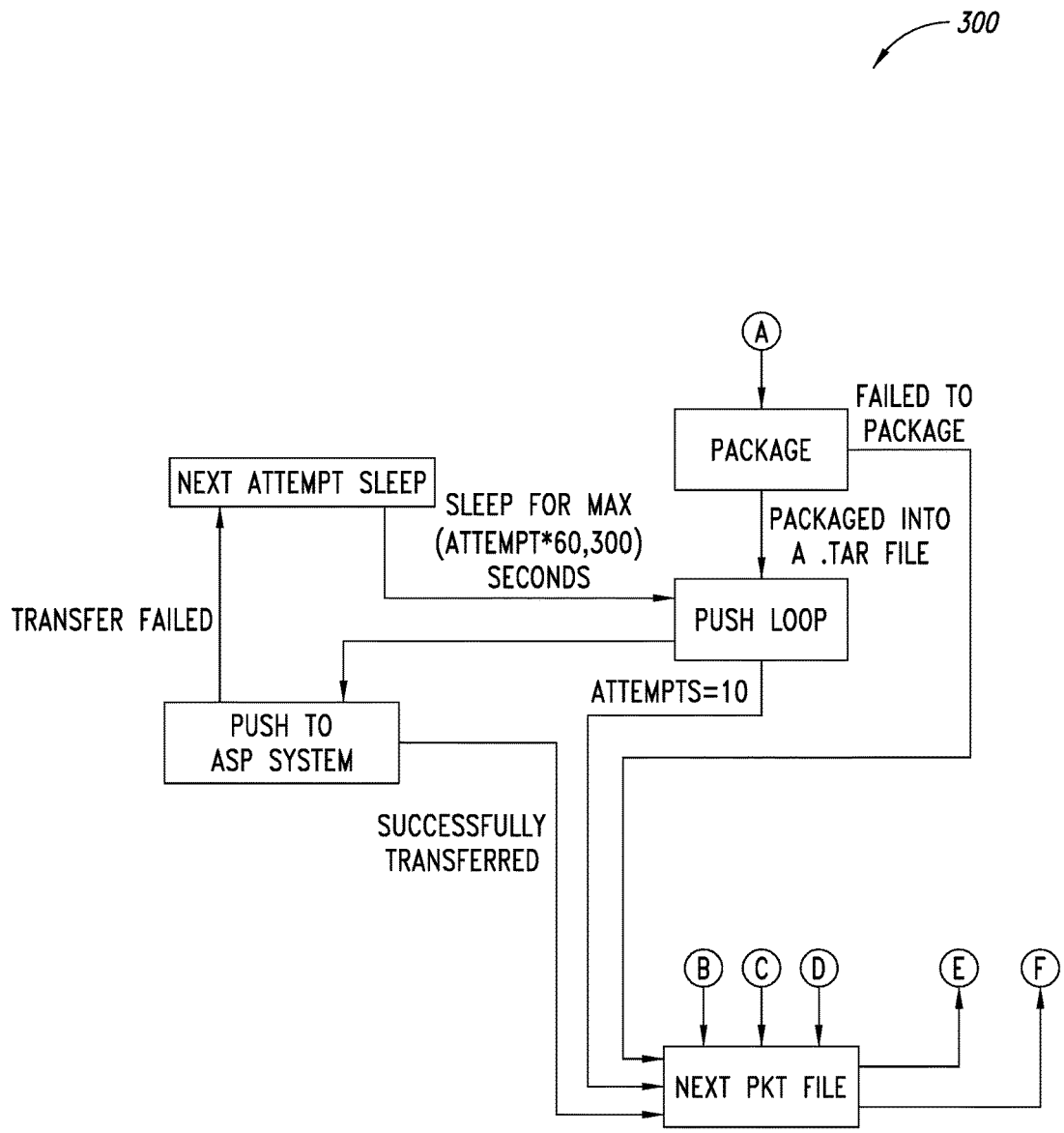

FIGS. 3A-3B show an example process 300.

Puller—Archiving Artifacts

The puller software is used to archive generated artifacts at a hospital (for example PACS). It is installed within a hospital's network and registers itself automatically with Arterys using a similar method to the pushers. A request is made with some identifying information, and a secret and key pair is returned to sign future requests for authentication and authorization purposes. The puller is then attached to an organization by a technician through a web portal.

It is also possible to download a version for an organization directly, with a unique key and secret included automatically in the installation process, so there is no need to auto register and attach the puller once installed.

The configuration for artifact endpoints is done on Arterys servers. Multiple locations can be configured with hostnames, ports, AE titles, and any other required information the puller would need to transfer data to it. These endpoints can be named, and are selectable from the Arterys web UI by a clinician when choosing where they would like their artifacts (reports/screenshots/videos) to be archived.

The puller monitors for artifacts by requesting a list from the Arterys API at regular and frequent intervals. The list of artifacts includes a unique id, and all of the configuration information for the endpoint the artifact will be stored in. The unique ID is used as input into another API request to retrieve the artifact from Arterys servers. The artifact is unzipped if required, and transferred using the configuration and method defined by the configuration included in the list request (e.g., storescp). Once all data is transferred, another API request using the provided ID is made to Arterys to mark the artifact as archived, and it will no longer appear in the list generated by the first request in the process loop. Once the artifact has been marked as archived, the Arterys servers will notify a user that archival is complete.

The puller sends heartbeat requests to Arterys providing detailed logs to help validate and ensure everything is functioning as expected. The puller will also occasionally—at a configurable time (e.g., once an hour or day)—make an API request to Arterys for new versions of the puller software. If a new version is available, it will be downloaded, installed and the puller will restart itself.

Example request to retrieve a list of artifacts:

```
GET https://app.arterys.com/api/1/artifact?
status=pending&timeout=20

[
    { "id" : "55006362619baaad4323f799","name":
    "report_one.zip", "digest":
"f90sdaf9d0safd0safd09safd", "size": 3523234,
    "dicom_host": "192.168.1.3"",
    "dicom_port": 1999, "dicom_aetitle",
    "aetitle for dicom endpoint" },
    { "id" : "454bf977be1cfbe146f36549", "name":
    "report_two.zip", "digest":
"9320028003002930sass9safd", "size": 1221134,
    "dicom_host": "192.168.1.3"",
    "dicom_port": 1999, "dicom_aetitle",
    "aetitle for dicom endpoint" }
]
```

Figure 4A:
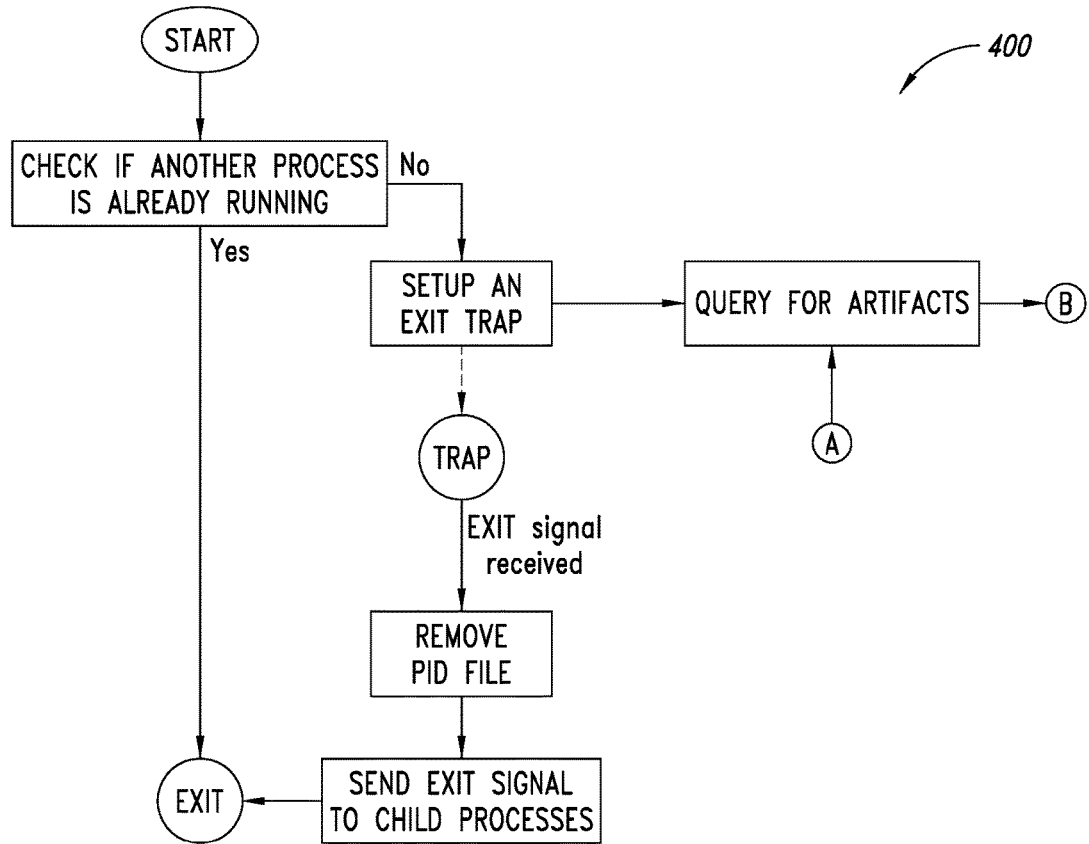
FIGS. 4A-4B are a flow diagram of an example process of monitoring for artifacts and arching executable by at least one processor, according to one illustrated embodiment.
Figure 4B:
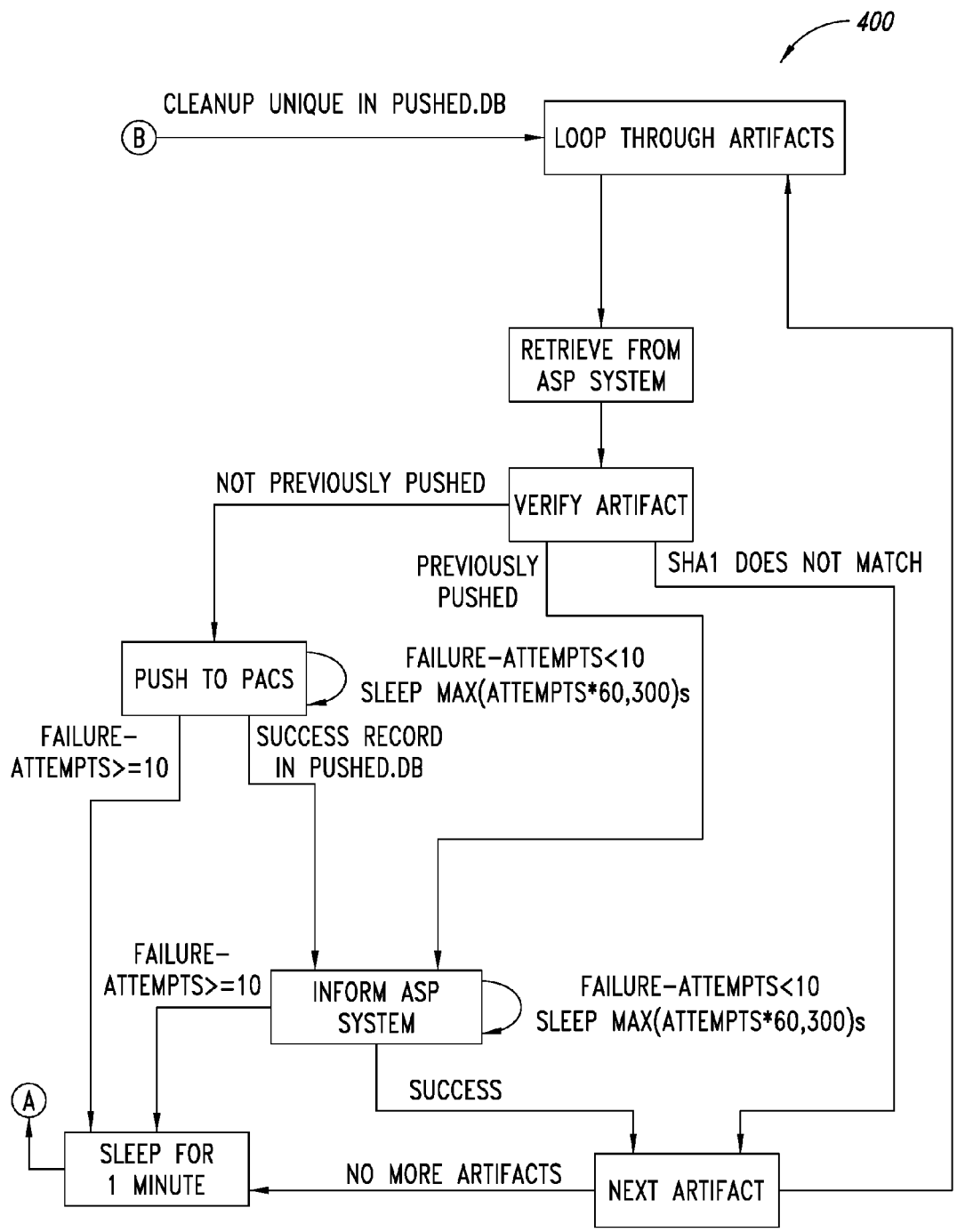

FIGS. 4A-4B show an example process 400 of monitoring for artifacts and archiving.

We have developed a method to securely deliver sensitive patient information to a client application from a service without disclosing the sensitive information to the service provider.

The data prior to being sent to the service provider is stripped of all patient identifiable health information, which is registered with the service and the original sensitive data is replaced with unique token identifier provided by the service.

The client when interacting with the service provider will identify these tokens and use an independent transport layer to replace the tokens with the sensitive patient health information.

Below is an example of a possible implementation of such a system:

Actors:

The user which interacts with the client software (user)

The client application (client)

The service which holds the sensitive patient information (service)

The application service provider

1. The user indicates to the software a set of files it would like to send to an application service provider.

2. For each file all sensitive information is gathered in JSON format and registered with the service over an http request.

EXAMPLE

```
POST https://sensitive.arterys.com/register-data HTTP/1.0
{
    "PatientName" : "Franklin\Benjamin"
    "Birthdate" : "1706-01-17"
}
returns
Location: "/4217ad2b78fff7eb9129a58b474efb3e"
```

3. The sensitive data is replaced with placeholders such as #{PatientName} and then the data is uploaded along with the Location url returned from the service.

4. When the client loads the data from the application service provider, strings that contain these sensitive tokens cause the client application to request the data from the service provider (either individually or in bulk).

EXAMPLE

```
GET
https://sensitive.arterys.com/
4217ad2b78fff7eb9129a58b474efb3e
PatientName
returns
"Franklin\Benjamin"
```

5. The client substitutes the tokens with the sensitive information.

Note: For authorization, we could use a sso such as saml2.

Workspaces

Workspaces are a solution the issues of storing and sharing a subset of application state throughout medical software.

Workspaces contain the application state of a study including any analysis, and when loaded they restore application the previous state. Application state includes the subset of component state related to a particular concern such as study review including measurements and ECC correction values etc.

Workspaces can be loaded and updated constantly while the user interacts with the software. Users start with a private default workspace when loading a study for the first time, and when reloading the most recently used applicable workspace is loaded.

Users can publish a study to a group or more users, which can also serve as a trigger for report generation and external system notifications.

When opening a published workspace for the first time a private copy of the workspace is created with is also loaded on subsequent reloads. Published studies are immutable and can never be modified.

Machine Learning with Medical Imaging

With a cloud interface, it is now possible to aggregate statistics from multiple sources to come up with predictions using machine learning. These multiple sources can be the results generated by multiple people within an organization, or even multiple organizations scattered across the world. The statistics that can be aggregated can be medical imaging pixel data, medical imaging metadata (e.g., DICOM headers), and for example the electronic medical records of patients (EMRs). The learning can be applied at a user level, at an organization level, or even at a macro level (e.g., globally).

In the case of trying to automatically quantify (e.g., annotate, measure, segment) medical images, there can be two different categories of deep learning, machine learning or artificial intelligence: For the medical imaging application, supervised learning is more appropriate because there is not sufficient data to learn from. In order to learn as effectively as possible, the cloud user interface has been tailored to allow users to add labels to the data in a structured fashion. For example, in the case of cardiovascular imaging, a user can make several measurements and label the measurements as they wish. Instead of allowing a completely user defined field, there is the option for a user to select a label from a predefined list that Arterys provides. By doing this, we can add labels to the data in a structured and automated fashion. Labeled data acts as the training data set to feed into a machine learning algorithm (i.e., like a random forest or deep learning CNN or RNN) so that the algorithm can predict an outcome based on new unlabeled data. For example, one optional step in the user review process is for them to "publish" their workspace or state in a way that confirms that they are happy with the labels that they have added to the data. The "publish" mechanism can be an icon in the user interface that they click to "save", or it can be the results that get sent to archive (for example to a hospital PACS server). There just needs to be a way to differentiate a user creating dummy measurements and annotations with true clinical measurements and annotations.

The benefit of a cloud interface is that every time a user makes any modification within the system interface to the suggestion provided, this modification then is saved and fed back into the machine learning labeled data. This creates a reinforcement learning loop that adds very valuable training data. The suggestions provided by the machine learning algorithm can be provided once when a user logs in or in real-time every time a user makes a modification during their session. For example, when a user identified a voxel in a medical image that is anatomy, all similar voxels can be identified in real-time in their session.

In the case of trying to predict the outcome of a particular treatment (and giving a resulting probability measure) or to predict which treatment choice is better suited for a particular patient, data from the EMR is critical. Having access to labeled medical device data (e.g., medical imaging, genomic data, wearables) is not sufficient in determining best treatment decisions. This data needs to be aggregated across all retrospective cases to offer a prediction to a new patient that has similar medical device data.

Machine learning can also be used for search in medical images. A user can type in a search field and find all images that for example has a particular type of disorder. A user can then verify that all the studies presented to them have this disorder and this data can then be fed back into the training dataset.

Picture and Video Service

We want the user to be able to capture pictures and video of the current state of their workflow. These images and videos need to include both image data generated on our server and overlays rendered on the client browser. To accomplish this we have a node-webkit based video service that allows us to run both our client and server software stack within the same environment. We then restore the current state of the user's workspace on the node-webkit environment and leverage the same compute nodes that were allocated for that user's session. If a single picture is requested by the user the service simply takes a screenshot of the restored workspace and the resulting image file is returned. In the case of a video request the service takes a screenshot for each frame of the current workflow and compiles the screenshot images into a video file using a video encoder which is then returned. The returned images or video can be stored on the server or sent back to the client to be viewed.

Below is an example of a detailed software design for the picture and video service:

---

Screenshots and Video Capture
~~~~~~~~~~~~~~~~~~~~~~~~~~
Requirements
~~~~~~~~~~~~

* screenshot should be a rendering of what the user currently sees in the viewport area
* video can be an mpr cycled through time
* video can be generated from a collection of key frames with in-betweens interpolating parameters that can be interpolated
* video can be user interaction recording \* output should contain everything that is on the viewport (image, webgl overlays, css overlays, ...)
\* screenshots and video frames should be full-quality Design Since we render everything on the client we need a client to generate the image.
Unfortunately, uploading a video would be prohibitive in the majority of network situations.
Hence, a screenshot/video service will run in the cluster that uses client rendering technology.
It will expose an interface over http to provide functionality defined in the requirements.
The service spins up node webkit processes on demand to render videos and screenshots as requests come in.
Upon receiving a request to render an image or collection of images, the service will launch a node webkit process and redirect it to signed URL for the user's worklist.
The node-webkit process will then load the study and inject the user's workspace
Next each frame will be rendered at full quality.
As a frame is rendered, node-webkit will perform an X11 screen capture and crop to the canvas viewport.
The image will be saved to disk.
Once all frames have been captured the service will return the screenshot, or in the case of a video,
a video will be encoded and returned.

Data Flow

\* user initiates request for screenshot or video.
\* webserver receives request
\* node-webkit process is started
\* node-webkit process opens a session, authenticated to load the required study
\* requested study is loaded
\* workspace in the request is injected into the study
\* upon completion of workspace load (including long running tasks like streamlines) it begins to render key frames
\* every frame is rendered full quality with no debounced image commands
\* as an image is rendered X11 screen grab (xwd) is executed on the window
\* the image is cropped to the viewport and saved to disk
\* if a video was requested encoding will run once images are generated
\* upon completion of all images an http response is sent back with the .png or .mp4
\* upon webserver receipt of the result, it will be saved in S3 and a reference saved to the database Additional Tools and Optimizations \* node-webkit requires webgl so the service will need to run on G2 instances
\* program 'xwd' in 'x11-apps' can capture window
\* ImageMagick 'convert' can convert xwd to png
\* ffmpeg can be used to generate .mp4 from a collection of .png Details Screenshots
+++++++++
Client message:
----
ws.emit ('generate-screenshot', params) ;
----
params:
----
{
  workspace_id : 'workspace-id',
  id : 'app-id',
  study_id : 'study-id',
  upload_id : 'upload-id',
  window_width : 'browser_window_width',
  window_height : 'browser_window_height',
  hostname : window.location.hostname,
  port : window.location.port,
  pathname : '/app/xxx'
}
----
Video
+++++

Client message:
----
ws.emit ('generate-screenshot', params) ;
----
params:
----
{
  // same as screenshot plus
  render_frames : [
    {
      orientation : [1,0,0,0,1,0,0,0,1],
      position : [0,0,0],
      timepoint : 1
      ...
    },
    {
      orientation : [0,1,0,1,0,0,0,0,1],
      position : [0,0,0],
      timepoint : 2
      ...
    }
    ...
  ],
  betweens : optional_number_of_frames_to_interpolate_between_frames
}
----

Web Server Handler

The message handler for 'generate-screenshot' attaches the current workspace to the args being sent to the webkit services
The webkit-client module is then used to send a request to one of the webkit services.
Once the response is received a record is inserted into the database and the image or video is stored.

Webkit-Client

The webkit-client module is responsible for routing a screenshot request to a node that can handle it.
The webkit-client subscribes to redis messages that are published by the currently running webkit nodes.
These messages include the existing instances of node-webkit that are running with the app-id they are running with.
When a request is received the webkit-client attempts to find a node that already has node-webkit running with the requested app-id.
Alternatively if a session has not been created yet it chooses the node with the least number of running sessions.
Once the node has been identified it sends the message over HTTPS to that host.
Arguments are sent in the body as JSON in a POST to the route '/webkit/execute'.
When the result returns a callback is invoked with the binary and a JSON blob containing the type (image/png or video/mp4), along with other useful information collected (e.g., timing information, size)

----
function execute (args, cb) {
    https.request ('POST','/webkit/execute',JSON.stringify(args),
    function(res)
{
    cb(null, {
      binary : res,
      json : {type : headers ['content-type'], info: { generation_start_time: <date>, generation_end_time: <date>}}
    });
  });
}
----

Webkit-Service

The webkit-service is a micro service that exposes an HTTPS interface to generate screenshots and videos.

The webkit-service listens only for POST requests at '/webkit/execute'.

Upon receiving a POST to '/webkit/execute' it creates a webkit-context and enqueues a request for a screenshot or video.

This module also takes care of authorizing the request that will be sent from node-webkit to the webserver by appending an auth_token associated with the special 'webkit-screenshot' user.

Webkit-Context

The webkit-context module is responsible for managing the node-webkit process that will run to generate a screenshot or video.

Upon creation a webkit-context creates a working directory to store intermediate results.

Next, it configures node-webkit by copying a simple 'index.html' and 'package.json' file into the working directory, and the 'args.json' containing the arguments passed into the context to render the screenshot/video.

Then node-webkit is started, and runs through the process of generating a screenshot.

When node-webkit exits, the webkit-context will look for the appropriate screenshot or video file to respond with.

Only one screenshot per app-id can run at a time.

A webkit-context registers itself in redis so that a webserver can route screenshot and video requests.

Node-Main

The node-main module is the bridge module running in node-webkit.

When node-webkit starts it waits until the 'global.window' variable is defined, and then reads in the args.json file and starts executing the steps to generate a screenshot.

These arguments denote the width x height to make the window and where to redirect window.location.href to.

It assumes the redirect points to a website that will set global.window.io, which is an Arterys defined variable denoting the websocket connection.

Once the websocket connection has been made it invokes a 'load-study' command, and waits for 'load-workspace-complete'.

Once all commands that may have been invoked by restoring a workspace are finished node-main starts capturing images.

If 'args.json' contained the field 'render_frames' it iterates through each one generating an image.

The images are generated by invoking xwd to dump the Xwindow.

ImageMagick convert is then used to convert to a png and crop to the '.ar-content-body-canvases'.

If there was more than one image generated then ffmpeg is invoked to encode the collection of images into an h.264 encoded video.

When the screenshot or video has been created, node-webkit will exit cleanly.

Any error will cause node-webkit to exit with a non zero code, which will indicate to the webkit-context that the screenshot has failed.

Anonymization Service

There are numerous regulatory requirements for a class of information typically denominated as protected health information (PHI). Many clinical facilities (e.g., hospitals) or entities that operate clinical facilities do not want any PHI to leave their network or control. Likewise, to avoid onerous handling and security requirements and to eliminate or reduce potential liability, an entity that provides services to the clinical facility may desire to be isolated from PHI. Various implementations of the networked environment may implement a service that prevents PHI from ever leaving the clinical facility's own network.

A number of approaches are described herein, the preferred approach depending on a location of a database that holds the PHI.

In cases where the database containing PHI and the computer nodes which require access to the PHI are all within the clinical facility's own network there are typically two different implementations that allow a user to access the MRI imaging and analysis services provided by a remotely located MRI image processing and analysis system which is outside the clinical facility's own network.

1) A first implementation employs multiple firewalls. Clinical facility (e.g. Hospital) deployment should consist of several security layers. The secure clinical facility network should contain all PHI information (e.g., MONGO® database, data files). The MRI image processing and analysis system (e.g., server component thereof) should run in a demilitarized zone (DMZ) or perimeter network configuration, with appropriate access permissions to the secure clinical facility network for data access as required through a firewall. Another firewall should separate the DMZ from the Internet, and only ports 80 and 443 should be exposed to the public through the Internet. This way a user can login via a regular URL from a remote location or network (e.g., home), and access (e.g., see) PHI from the remote location or network.

2) A second implementation employs a virtual private network (VPN). The particular URL for accessing the services provided by the MRI image processing and analysis system is only accessible if the client device is first connected through a VPN of the clinical facility.

In cases where the clinical facility does not want the PHI in databases outside clinical facility's own network and the computer nodes which require access to the PHI are hosted outside the clinical facility's own network (e.g., AMAZON® Web Services or AWS), an anonymization service can run within the clinical facility's network. The anonymization service receives raw DICOM files, anonymizing the raw DICOM files by removing any plain text PHI, and replaces the plain text PHI with a hash of the PHI (e.g. all PHI fields in the DICOM images are identified and converted to salted hashes). A key that turns the plain text PHI into a hash is kept within the clinical facility's own network and is accessible by the anonymization service.

This anonymization service can operate in at least two ways

1) A first implementation employs a Proxy Server. As requests come from a client, either within the clinical facility's network or outside the clinical facility's network, the request passes through a proxy server, and the anonymization service replaces the hash with the plain text PHI. This allows the client to always see PHI. In this implementation, all HTTP/S requests are funneled to the proxy server.

2) A second implementation employs a one-time Lookup. When a client connects to the server(s) of the MRI image processing and analysis system, which are located outside the clinical facility's network, a flag indicates to the client whether the client is missing information required to render the PHI. If the client does not have the plain text PHI, the client connects to the anonymization service and requests the PHI by providing the hash or an identifier (ID). The correct plain text PHI is then provided to the client based on that provided hash or ID. The received PHI is then stored locally (cached) by the client, as long as the session is active. When the user logs out, the client purges the cache.

In all of the above described implementations, PHI is transmitted from the client to/from the anonymization service to/from server encrypted. In addition, any stored data may also be in encrypted form.

In the case that a customer would want their PHI hosted in the cloud, but in some circumstances wants to hide PHI in their client (e.g. for academic conferences) we have created an anonymization filter (which will be part of the anonymization service). The anonymization filter is a filter that is installed on the client data stream that inspects the traffic that passes through the filter and removes PHI before allowing data to proceed through the communication pipeline (it's a streaming data filter).

PHI Service

Figure 5:
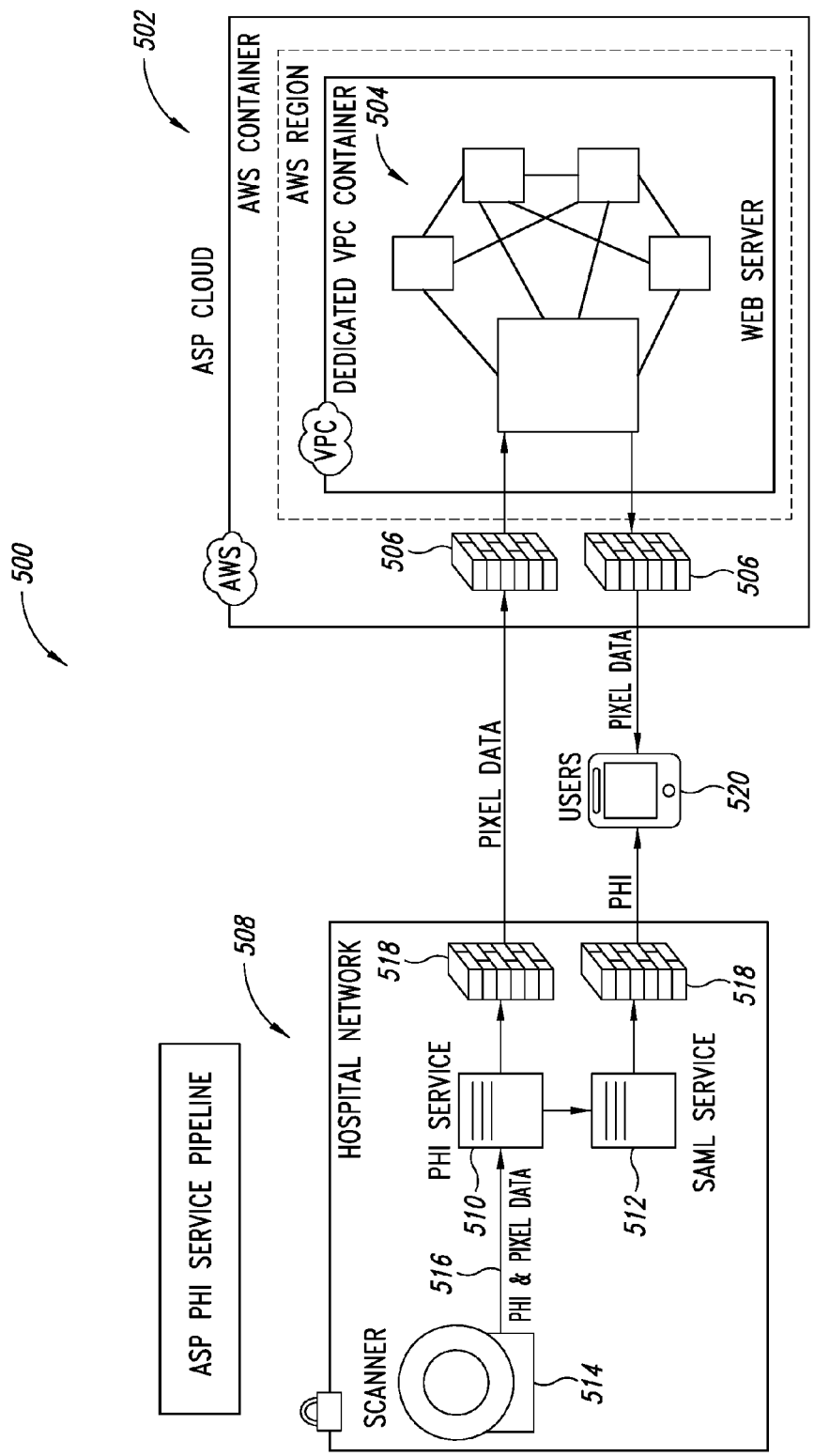
FIG. 5 is a schematic illustration of a PHI service pipeline, according to one illustrated embodiment.

FIG. 5 shows a networked environment for a medical analytics system or platform 500, according to one illustrated embodiment. The platform comprises an analytics service provider (ASP) network 502 which comprises an ASP system 504 (e.g., one or more processor-based devices) which communicates through a firewall 506 with various systems associated with medical provider (e.g., hospital) networks 508 (one shown). The ASP system 504 provides some or all of the various functionality discussed above. For example, the ASP system 504 may be similar or identical to the image processing and analysis system 104 of FIG. 1, for example. The ASP system 504 may be implemented using a cloud architecture and, as such, may comprise a number of distributed processor-based devices. The ASP system 504 may access external systems via one or more communications networks accessible via the firewall 506, for example.

The medical provider or hospital network 508 may include one or more protected health information (PHI) systems 510 (one shown) operatively coupled to one or more external networks (e.g., Internet) via a firewall 518. The medical provider network 508 may also include a Security Assertion Markup Language (SAML) service 512 operatively coupled to the PHI service 510. In at least some of the implementations discussed herein, the SAML service 512 may be considered to be part of or integrated with the PHI system or service 510.

Figure 7:
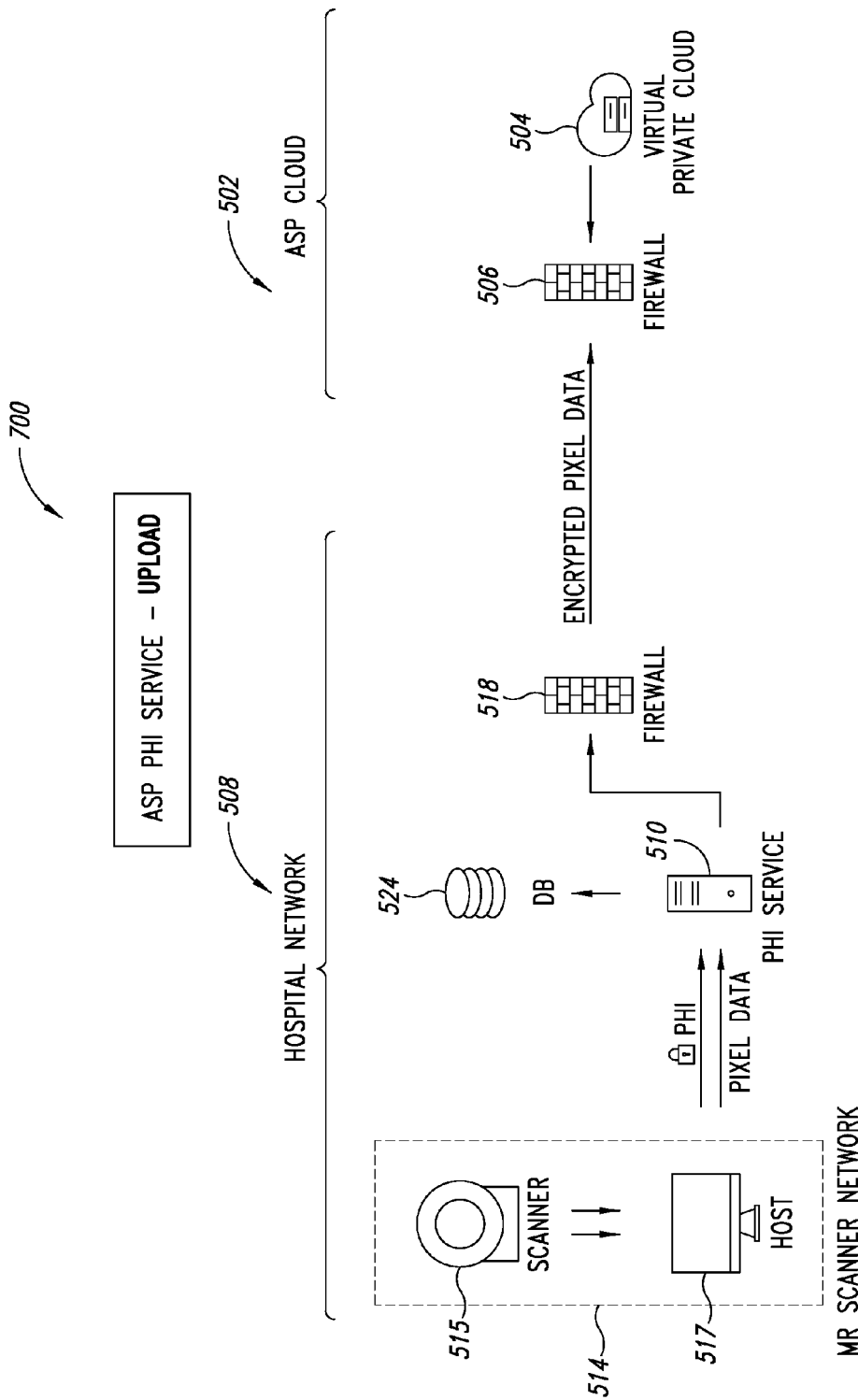
FIG. 7 is a schematic illustration of the PHI service of FIG. 5, showing DICOM files being stripped of PHI data, according to one illustrated embodiment.
Figure 8:
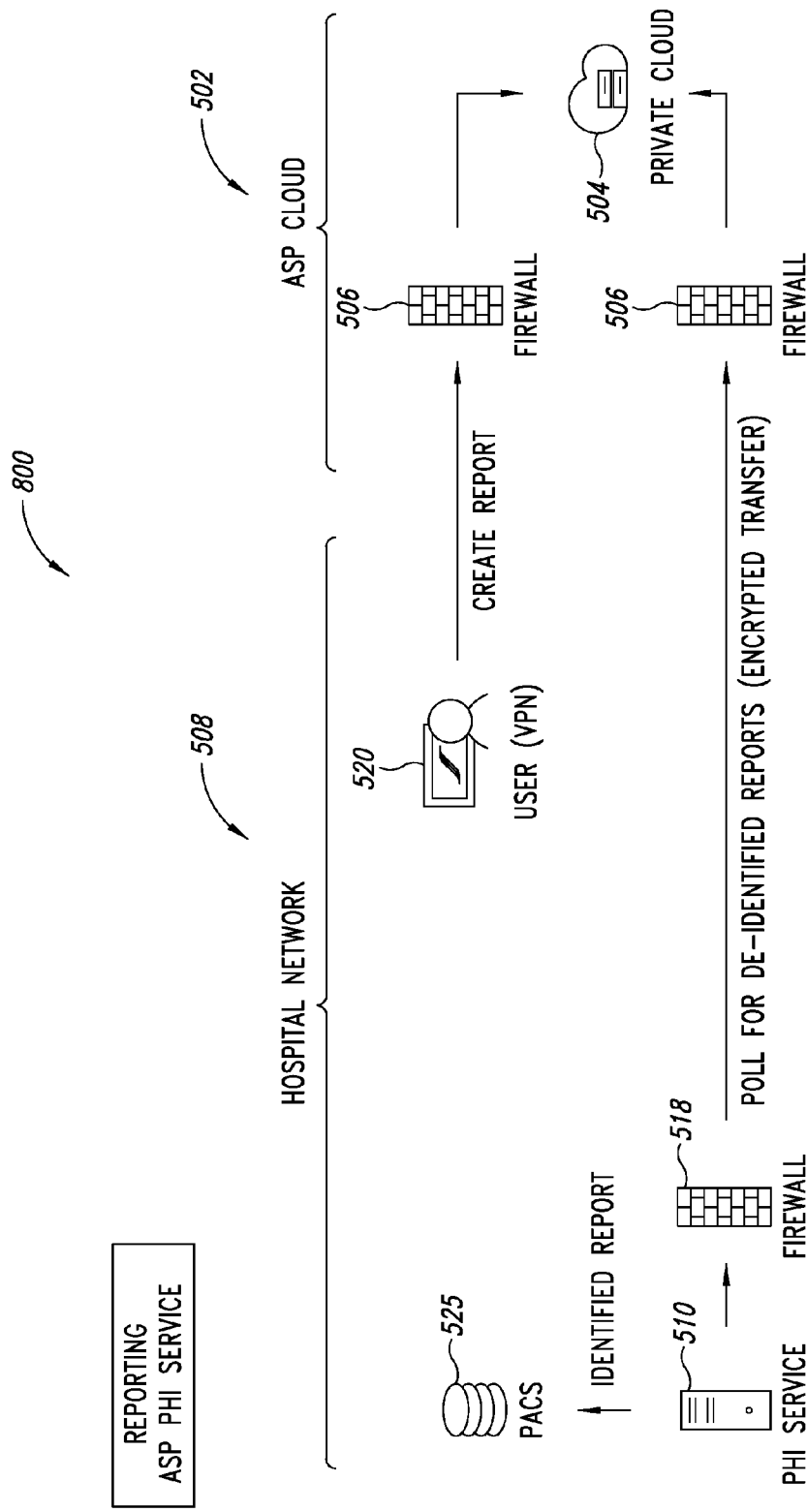
FIG. 8 is a schematic illustration of the PHI service, showing a user operating a web application to request the ASP system to store a report on a registered PACS server of the user's organization, according to one illustrated embodiment.

The PHI system 510 may be operatively coupled to an MRI acquisition system 514 which includes an MRI machine 515 (FIG. 7) and a host computer system 517 (FIG. 7). The PHI system 510 may also be communicatively coupled to a database 524 or other nontransitory processor-readable storage medium which stores medical study data received from the MRI acquisition system, among other data. The medical study data may include MRI data, 4-D flow data, or any other type of data which may have PHI or other protected or personal information. As shown in FIG. 8, the PHI system 510 may be communicatively coupled to a picture archiving and communication system (PACS) 525 or other destination storage associated with the medical provider.

The MRI acquisition system 514 is typically located at a clinical facility, for instance a hospital or dedicated medical imaging center. The MRI acquisition system 514 may be similar or identical to the MRI acquisition system 102 of FIG. 1. Various techniques and structures, as explained herein, may advantageously allow the ASP system 504 to be remotely located from the MRI acquisition system 514. The ASP system 504 may, for example, be located in another building, city, state, province or even country.

The ASP system 504 may include one or more servers to handle incoming requests and responses, and one or more rendering or image processing and analysis computers. The server(s) may, for example take the form of one or more server computers, workstation computers, supercomputers, or personal computers, executing server software or instructions. The one or more rendering or image processing and analysis computers may take the form of one or more computers, workstation computers, supercomputers, or personal computers, executing image processing and/or analysis software or instructions. The one or more rendering or image processing and analysis computers will typically employ one, and preferably multiple, graphical processing units (GPUs) or GPU cores.

While FIG. 5 illustrates a representative networked environment, typical networked environments may include many additional MRI acquisition systems, ASP systems, PHI systems, computer systems, and/or entities. The concepts taught herein may be employed in a similar fashion with more populated networked environments than that illustrated. For example, a single ASP entity may provide image processing and analysis services to multiple diagnostic entities. One or more of the diagnostic entities may operate two or more MRI acquisition systems. For example, a large hospital or dedicated medical imaging center may operate two, three or even more MRI acquisition systems at a single facility.

Generally, the PHI system 510 may create a secure endpoint for medical study data (e.g., DICOM files). The PHI system 510 may automatically or autonomously strip files of PHI, and upload the de-identified medical study data to the ASP system 504 for processing and/or analysis. Further, as discussed below, a web application may be provided for a user operating a client processor-based device 520 which has secure access to the medical provider network 508 (e.g., via VPN). The web application operates to merge local PHI data from the PHI system 510 with the de-identified data from the ASP system 504, without providing any PHI data to the ASP system.

An organization (e.g., hospital, other medical provider) may implement the PHI system 510 onsite or in the cloud. The PHI system 510 which implements the PHI service allows PHI data to stay within the medical provider's network and control, while allowing the ASP system 504 to function in the cloud while meeting regulatory laws and ensuring patient privacy.

Figure 6:
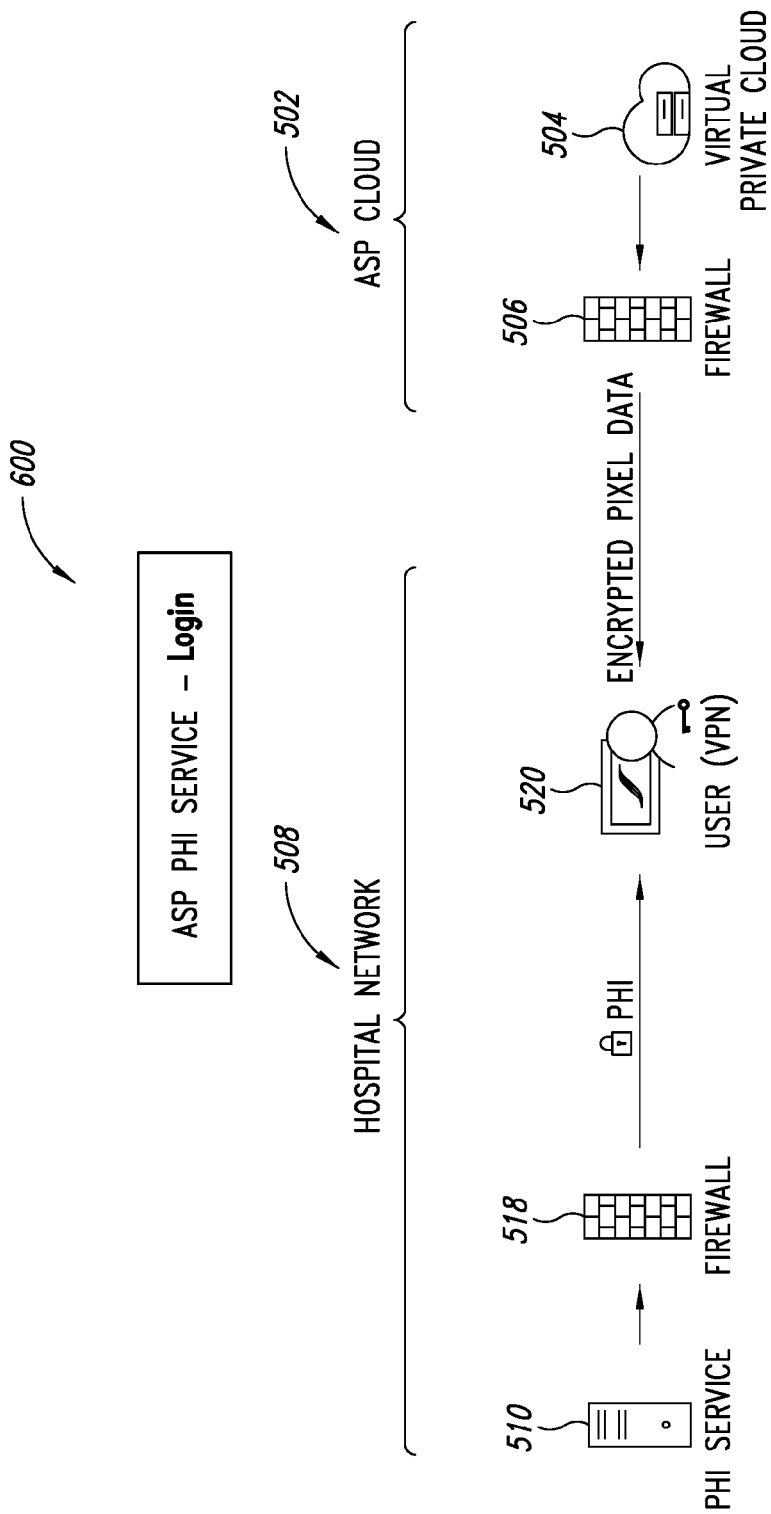
FIG. 6 is a schematic illustration of a PHI service of FIG. 5, showing PHI data kept within a medical provider's network being merged with pixel data from an analytics service provider (ASP) system via the ASP's web application, according to one illustrated embodiment.

As shown in the process 600 of FIG. 6, when a user loads a medical study (e.g., Mill) using a web browser executing on the client processor-based device 520 which has secure access to the medical provider's network 508, medical study data is re-identified on demand within the web browser. Data is requested by the web application from both the ASP system 504 (e.g., via a web application of the ASP system) and a web API of the PHI system 510 simultaneously. The PHI data and de-identified data are then merged seamlessly within the user's web browser executing on the client processor-based device 520 during an active session.

The PHI system 510 may provide an API for a medical device (e.g., MRI acquisition system 514) to transfer medical study data over an encrypted connection. The data may then be uploaded securely in an efficient method to the ASP system 504. This provides both ease of integration with current medical devices, and provides security for data transferred outside of a medical provider's network 508. The PHI system 510 may reduce complicated, per device network configuration by ensuring that all communication inside and outside the medical provider's network 508 is done securely (e.g., over an HTTPs protocol over HTTPs ports).

As discussed further below, artifacts, such as secondary capture objects and reports generated within the web application of the ASP system 504, may need to be pushed back to the medical provider's reporting system and/or PACS. The PHI system 510 acts as a secure proxy, pulling the artifacts from the ASP system 504 and pushing the re-identified data to the configured location within the medical provider's network 508. This allows the medical provider to use the services provided by the ASP system 504 without allowing any inbound network requests, which keeps the medical provider's network secure.

The PHI system 510 may also be self-updating, and may allow security updates as well as functionality updates without requiring intervention by staff of the medical provider.

FIG. 7 shows an example process 700 of operating the PHI system 510 to strip PHI data from DICOM files. The PHI system 510 receives the DICOM files, which include PHI data and pixel data, from the host computer system 517 of the MRI acquisition system 514. The PHI system 510 strips the PHI data from the DICOM files and stores the PHI data in the database 524. The PHI system 510 uploads the de-identified pixel data to the ASP system 504 via the firewall 518 for use by the ASP system 504 to perform the various functions discussed above.

FIG. 8 shows an example process 800 of storing a user generated report on the registered PACS server 525 associated with the medical provider. As shown, the user operating the client processor-based device 520 may request, via the web application, that the ASP system 504 create a report. Responsive to the request, the ASP system 504 generates the report. The PHI service 510 may from time-to-time poll the ASP system 504 for de-identified reports. When the ASP system 504 has one or more de-identified reports available, the ASP system 504 sends the one or more de-identified reports to the PHI system 510 via an encrypted transfer. The PHI system 510 then stores the received report to the PACS server 525 for later use.

Figure 9:
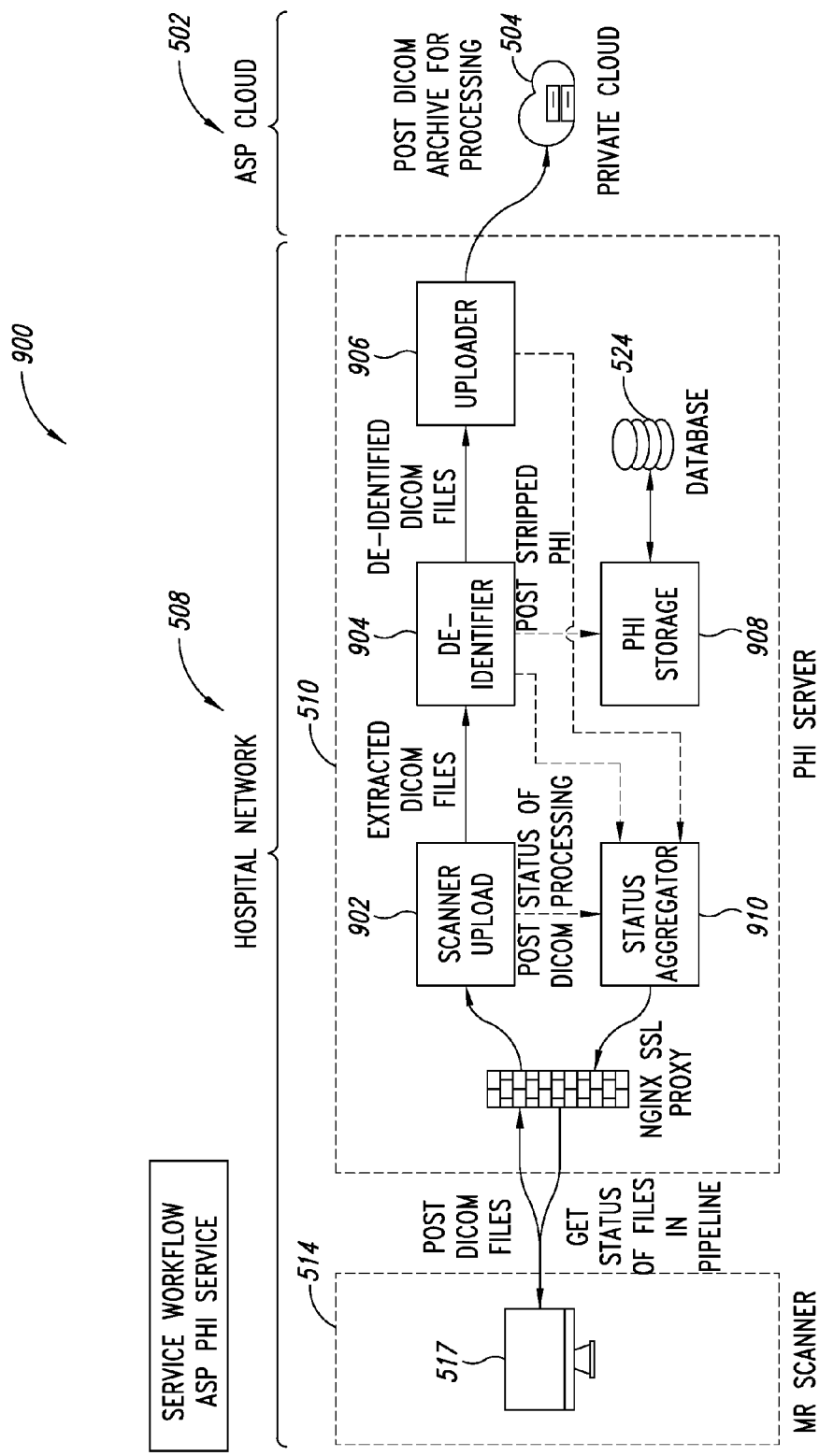
FIG. 9 is a schematic illustration of the PHI service, showing how DICOM files are handled by the PHI server of the PHI service, according to one illustrated implementation.

FIG. 9 is a schematic diagram 900 of the PHI system 510, showing how DICOM files received by the host computer system 517 of the MRI acquisition system 514 are handled by the PHI system 510. Among other services, the PHI service 510 may include a scanner upload service 902, a de-identifier service 904, an uploader service 906, a PHI storage service 908, and a status aggregator service 910. Each of these services is discussed further below.

Generally, the scanner upload service 902 is responsible for uploading DICOM files from the host computer system 517 of the MRI acquisition system 514. The scanner upload service 902 also posts status of DICOM file processing to the status aggregator service 910. The scanner upload service 902 also sends extracted DICOM files to the de-identifier service 904.

As discussed further below with reference to FIG. 12, the de-identifier service 904 functions to strip or remove any PHI data from the DICOM files. The de-identifier service 904 then sends the de-identified DICOM files to the uploader service 906 and sends the stripped PHI data to the PHI storage service 908, which stores the PHI data in the database 524. The de-identifier service 904 also posts de-identification status information to the status aggregator service 910. The uploader service 906 sends the de-identified DICOM files to the ASP system 504 over an encrypted transfer protocol for processing by the ASP system.

Figure 10:
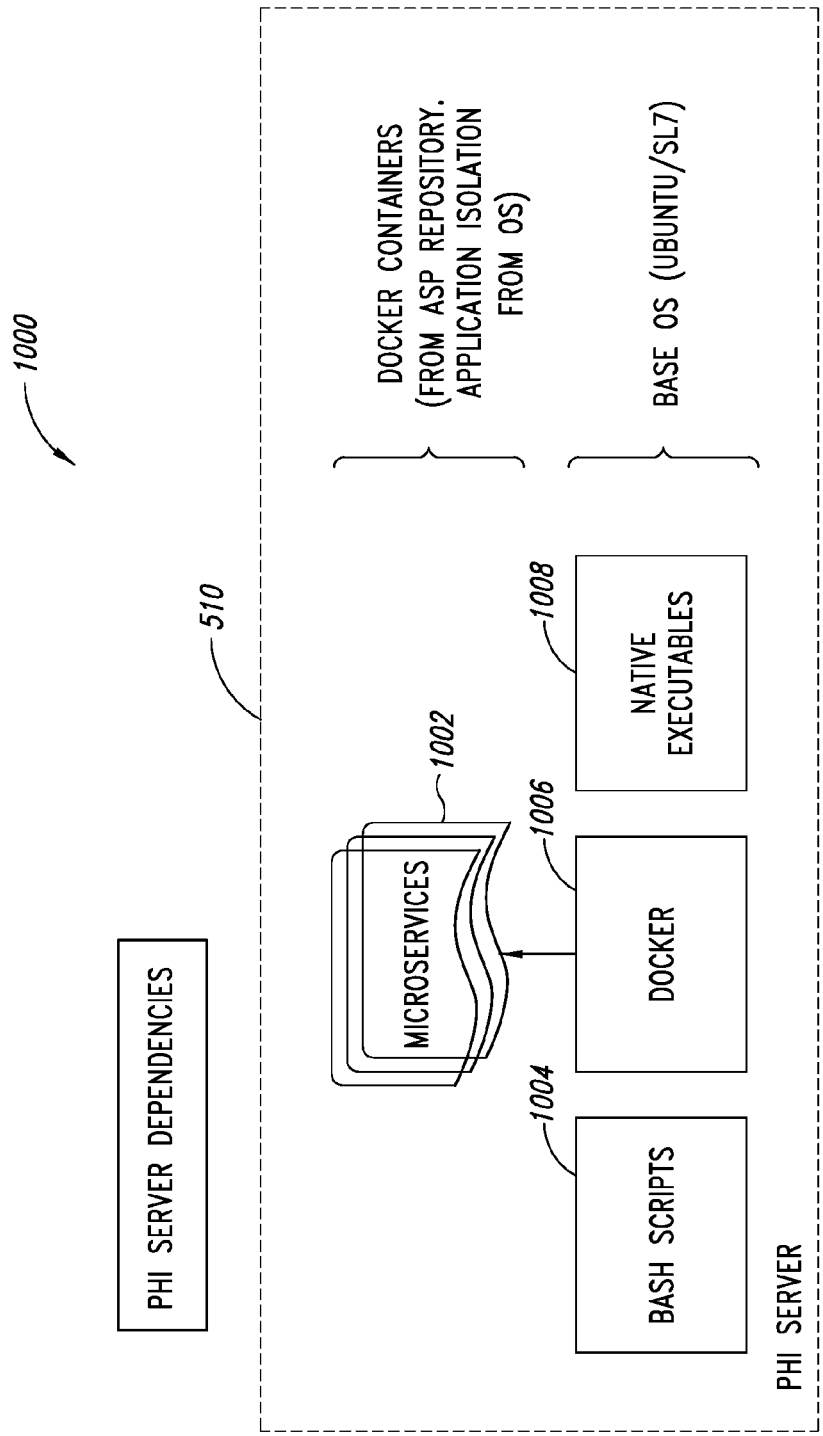
FIG. 10 is a schematic illustration of the PHI service, showing how PHI service dependencies are organized, according to one illustrated embodiment.

FIG. 10 is a schematic diagram 1000 of the PHI system 510, showing how PHI service dependencies are organized. The PHI system 510 includes a base operating system (e.g., Ubuntu/SL7) which comprises bash scripts 1004, Docker 1006, and native executables 1008. The Docker 1006 includes a number of Docker containers which are used to implement the various microservices 1002 of the PHI system 510. As shown in FIGS. 9 and 11, such microservices 1002 may include the scanner upload service 902, the de-identifier service 904, the uploader service 906, the storage service 908, the status aggregator service 910, an SSL proxy service 1106, an artifact service 1108, and a launch service 1110, for example.

Figure 11A:
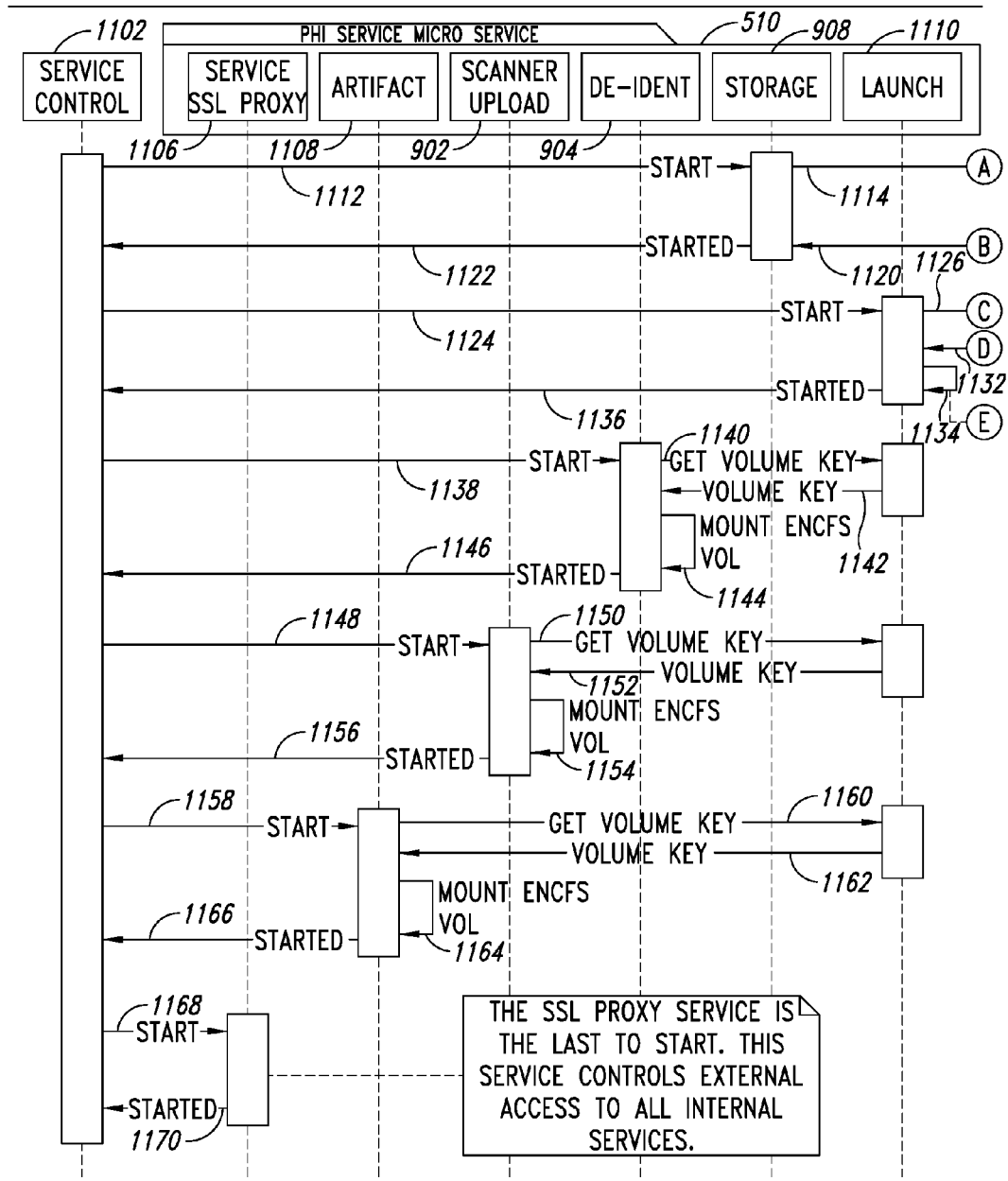
FIGS. 11A-11B are a system sequence diagram illustrating a process for a launch sequence of the PHI service, according to one illustrated embodiment.
Figure 11B:
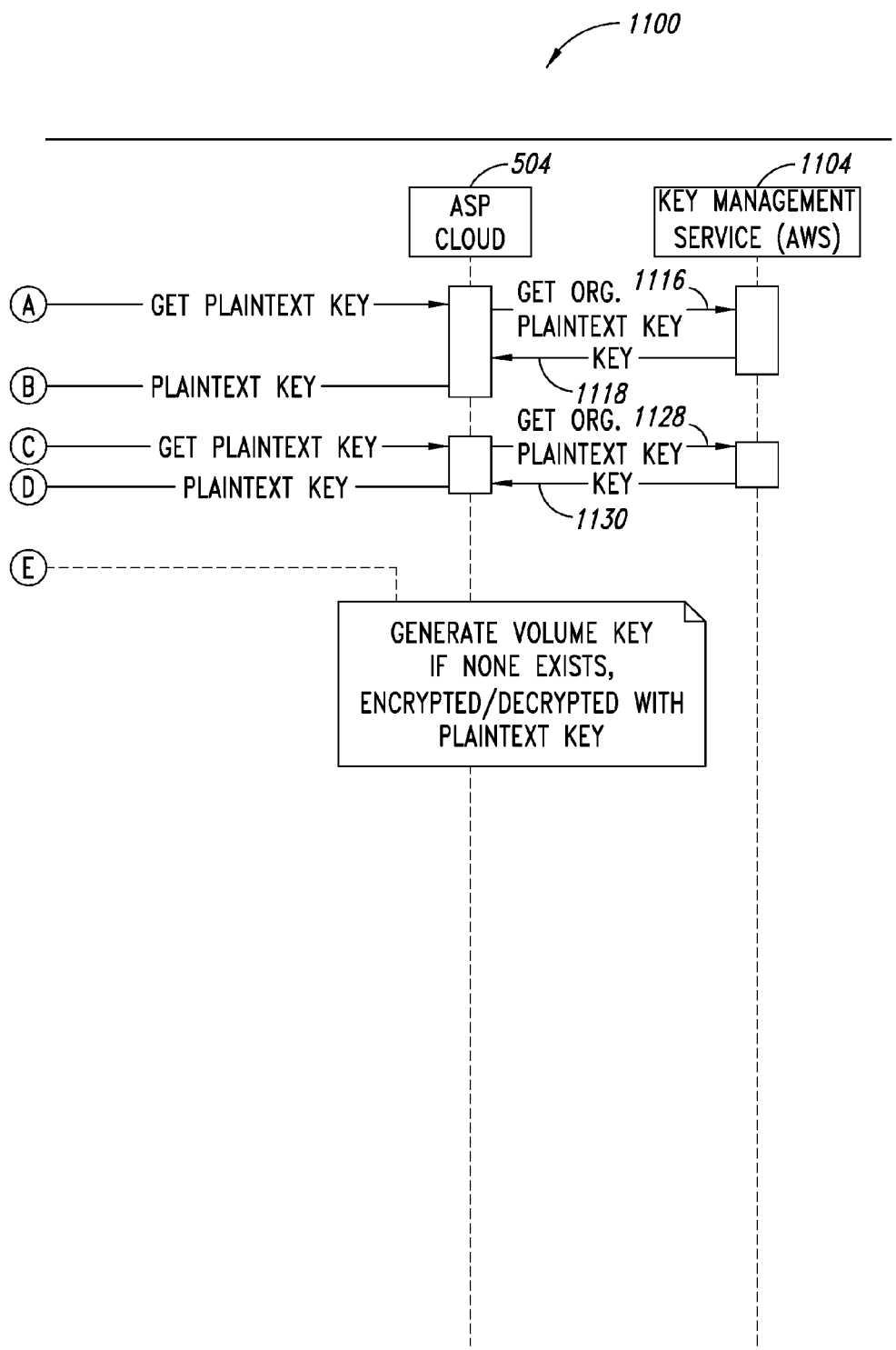

FIGS. 11A-11B (collectively, FIG. 11) are a system sequence diagram 1100 illustrating a launch sequence of the PHI service 510. The components associated with implementing the launch sequence include a service control node 1102, a key management service 1104 of the PHI service 510, the ASP system 504, the scanner upload service 902, the de-identifier service 904, the storage service 908, the SSL proxy service 1106, the artifact service 1108, and the launch service 1110.

At 1112 and 1114, the service control 1102 creates a signed request to the ASP system 504 via the storage service 908. At 1116, the ASP system 504 requests a plaintext data key from the key management service 1104. At 1118, the key management service 1104 returns the key to the ASP system 504 which, at 1120, returns the plaintext data key and an encrypted data key to the storage service 908 of the PHI system 510. At 1122 storage service 908 provides an indication to the service control 1102 that the storage service 908 has started.

At 1124, the service control 1102 sends a start command to the launch service 1110. At 1126-1130, the launch service 1110 requests a plaintext key from the key management service 1104 via the ASP system 504. At 1134, the launch service 1110 generates a volume key if none exists. The volume key is then encrypted with the plaintext data key and is now referred to as the encrypted volume key. The encrypted volume key is stored along with the encrypted data key. The encrypted data key uniquely identifies the plaintext data key, which allows the PHI system 510 to roll keys on subsequent launches. At 1136, the launch service 1110 notifies the service control 1102 that the launch service has started.

In at least some implementations, the volume key is used to initialize a mounted volume (e.g., Docker volume) as an EncFS file system in paranoia mode using aes-256-gcm. All other services which need to write data to disk need to first request the volume key from the launch service 1110. As the volume key may not be kept in memory, upon request, the launch service 1110 decrypts the encrypted volume key with the in-memory plaintext data key and returns the volume key to the requesting service. The requesting service then uses that volume key to mount the shared EncFS volume in decrypted fashion.

At 1138, the service control 1102 starts the de-identification service 904. At 1140, the de-identification service 904 gets the volume key from the launch service 1110 which, at 1142, returns the volume key to the de-identification service. At 1144, the de-identification service 904 uses the volume key to mount a shared EncFS volume. At 1146, the de-identification service 904 notifies the service control 1102 that the de-identification service has started.

At 1148, service control 1102 starts the scanner upload service 902. At 1150, the scanner upload service 902 gets the volume key from the launch service 1110 which, at 1152, returns the volume key to the scanner upload service. At 1154, the scanner upload service 902 uses the volume key to mount the EncFS volume. At 1156, the scanner upload service 902 notifies the service control 1102 that the scanner upload service has started.

At 1158, the service control 1102 starts the artifact service 1108. At 1160, the artifact service 1108 gets the volume key from the launch service 1110 which, at 1162, returns the volume key to the artifact service. At 1164, the artifact service 1108 uses the volume key to mount the EncFS volume. At 1166, the artifact service 1108 notifies the service control 1102 that the artifact service has started.

At 1168, the service control 1102 starts the SSL proxy service 1106. The SSL proxy service 1106 is the last to start. The SSL proxy service 1106 controls external access to all internal services. At 1170, the SSL proxy service 1106 notifies the service control 1102 that the SSL proxy service has started.

Figure 12:
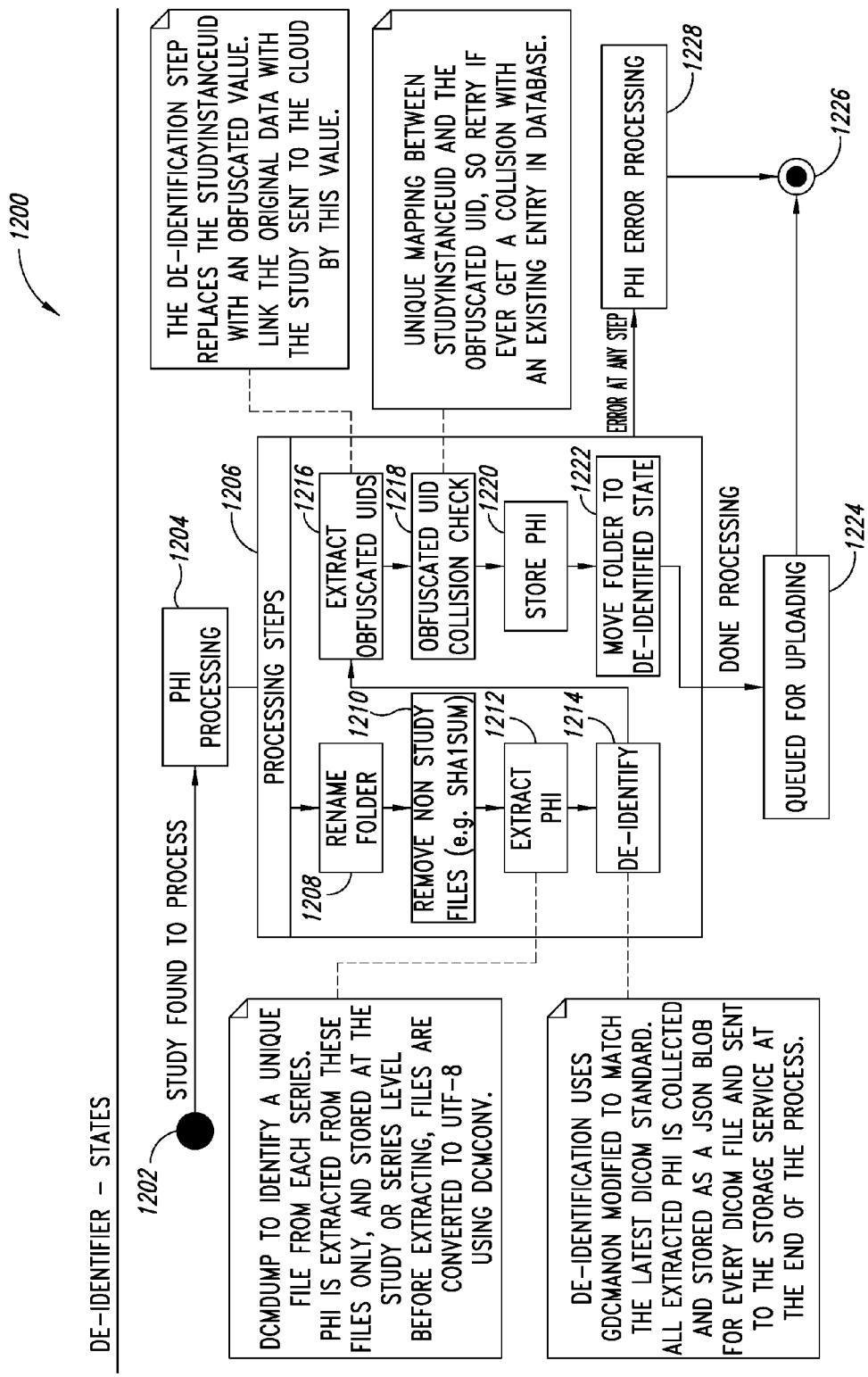
FIG. 12 is a flow diagram illustrating a process for implementing a de-identification service of the PHI service, according to one illustrated embodiment.

FIG. 12 is a flow diagram illustrating a process 1200 for the de-identification service 904 of the PHI service. The de-identification service 904 is responsible for processing a study uploaded by the scanner upload service 902, collecting all information, and ensuring that it is safe to upload to the ASP system 504. A primary component of the de-identification service 904 is the actual de-identification act performed on the DICOM data. In at least some implementations, a modified gdcmanon utility from the GDCM project may be used.

The process 1200 begins at 1202, for example, when the scanner upload service 902 sends extracted DICOM files for a study to the de-identification service 904. At 1204, a PHI processing module is initiated. At 1206, a number of processing acts 1208-1222 are performed. In particular, at 1208 a folder which contains the study to be processed is renamed. At 1210, all non-study files (e.g., sha1sum) are removed. At 1212, the de-identification service 904 extracts PHI from the DICOM files. At 1214, the de-identification service de-identifies the DICOM files. All extracted PHI data may be collected and stored for every DICOM file and may be sent to the storage service 908 at the end of the process, for example.

At 1216, the de-identification service 904 extracts obfuscated UIDs. The de-identification act 1214 replaces a StudyInstanceUID with an obfuscated value. The original data is linked with the study sent to the ASP system 504 by this value.

At 1218, the de-identification service 904 performs a collision check for the obfuscated UID to ensure there is a unique mapping between the StudyInstanceUID and the obfuscated UID. If there is a collision, a different obfuscated UID may be generated to ensure a unique mapping between the StudyInstanceUID and the obfuscated UID.

At 1220, the de-identification service 904 sends the PHI data to the storage service 909, which stores the PHI data 1220 in the database 524, for example. At 1222, the de-identification service 904 moves the folder to the de-identified state. At 1224, once the processing act 1206 is completed, the de-identified data is queued for uploading to the ASP system 504 by the uploader service 906. At 1226, the process 1200 ends until, for example, another study is found which needs to be processed. At 1228, a PHI error processing module may be executed if an error is detected at any of the processing acts 1208-1222.

The PHI data collected may be organized in a document with two levels information, a study level and a series level. The data may be indexed by an obfuscated StudyInstanceUID which provides the link with the data stored by the ASP system 504. The PHI data may be sent to the storage service 908, which encrypts and stores the data in the database 524.

To handle ISO2022 data, the dcmconv utility (from the dcmtk project) may be used. Before reading PHI data from the reduced set of DICOM files, the DICOM files may be converted to UTF-8. This speeds up the process by limiting the number of files that need to be converted, while ensuring all PHI data collected is in a consistent format.

The utility gdcmanon handles de-identification in a folder of DICOM data. However the project only de-identifies to the 2008 NEMA standard. As such, in at least some implementations a modified version of the gdcmanon utility is used which adds the required DICOM tags to be compliant with the latest DICOM standard.

The utility also encrypts the PHI and stores the PHI within each DICOM file as a new tag. The PHI system 510 does not send any de-identified data, even when encrypted, so the utility is further modified to skip the step of inserting a new tag of encrypted data. This further speeds up the process by removing the need to add an additional step of removing that tag later.

For the PHI system 510 to function, only a small subset of PHI at the study and series level as needed. However, the DICOM standard removes many more fields. To keep the database 524 of the PHI system 510 smaller, which enhances performance for the user, the PHI system may only store the required data in the database 524. In cases where additional fields are needed, or if there is a need to reprocess the PHI data, the de-identified data removed from each DICOM file may be stored (e.g., as a JSON file which is compressed and archived).

Figure 13A:
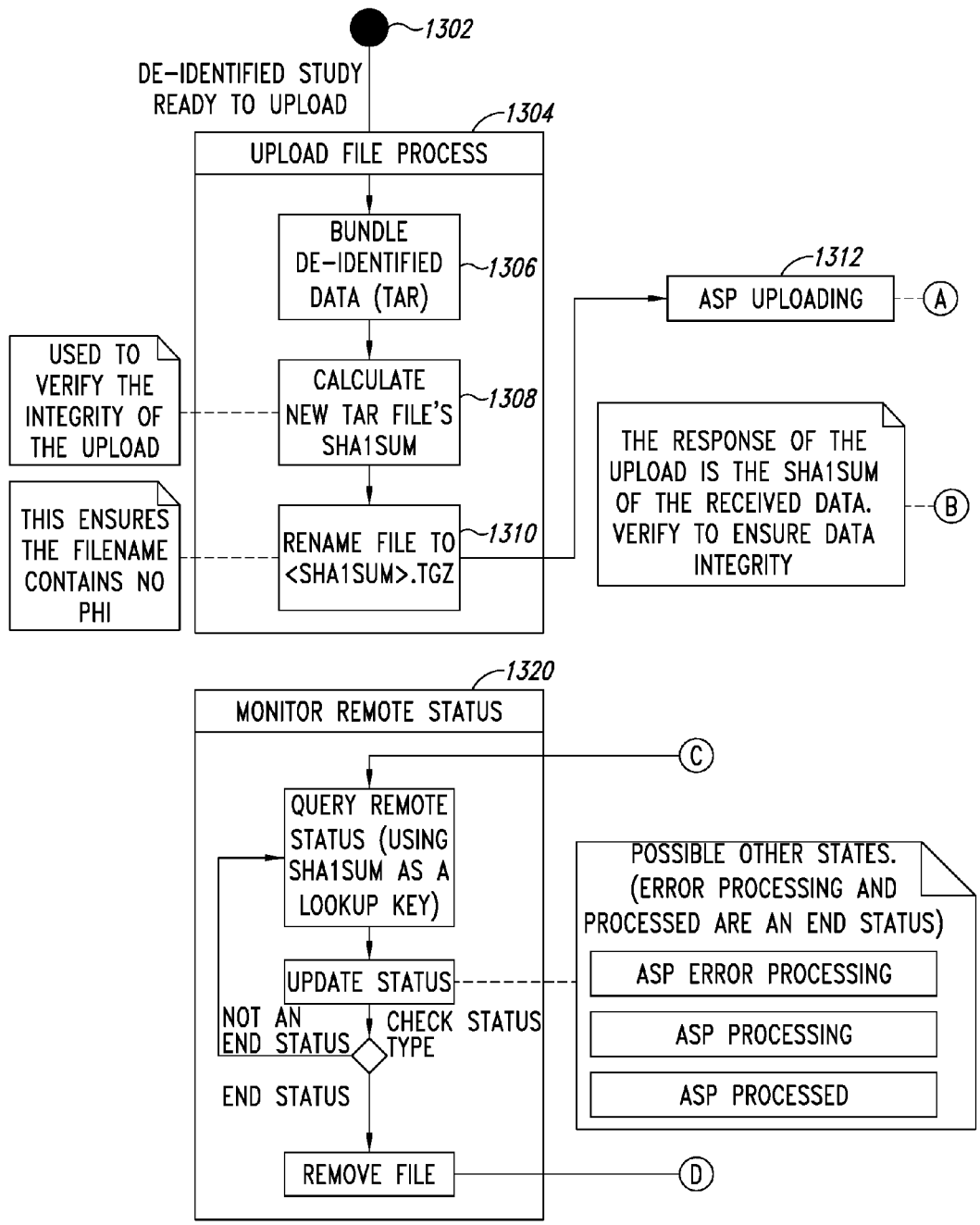
FIGS. 13A-13B are a flow diagram illustrating a process for a pusher or uploader service of the PHI service, according to one illustrated embodiment.
Figure 13B:
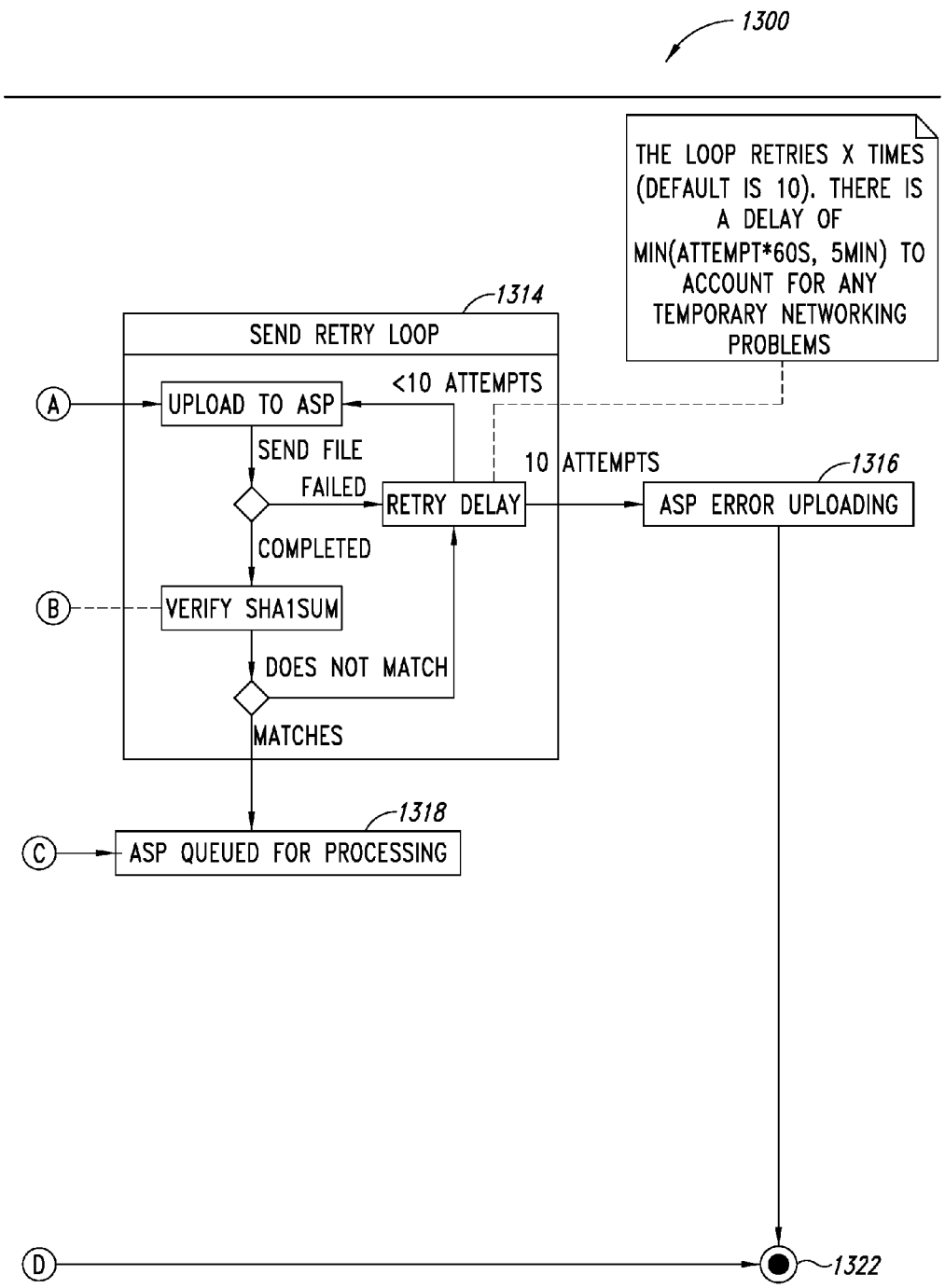

FIGS. 13A-13B (collectively, FIG. 13) are a flow diagram illustrating a process 1300 for the uploader or pusher service 906 of the PHI system 510. The pusher service 906 has two main tasks. The first task is to transfer the identified studies to the ASP system 504. The second task is to monitor the status of an uploaded study, and update the internal status of the PHI system 510 until an end state is reached. This allows the host computer system 517 to request the status for a study from the PHI system 510, and to receive information from the ASP system 504.

At 1302, the pusher service 906 monitors a folder for de-identified studies provided by the de-identification service 904. The pusher service 906 then begins an upload file process 1304. At 1306, the pusher service 906 bundles the de-identified data (e.g., tar and gzip the study). At 1308 the pusher service 906 calculates the shalsum of the new bundled file (e.g., tar file), which shalsum is used to verify the integrity of upload and also provides a key with which to request status updates. At 1310, the pusher service 906 may rename the file (e.g., "<shalsum>.tgz") to ensure the file name contains no PHI.

At 1312, the renamed file may then be uploaded to the ASP system 504 using a send retry loop 1314. The sender retry loop continues to attempt to upload the file with an increasing delay between attempts. If the file fails to upload after a number of attempts, an error uploading module 1316 may be executed. If the upload is successful, the shalsum is verified to ensure data integrity. At 1318, the uploaded file is then queued for processing by the ASP system 504.

At 1320, the uploader service 906 may remotely monitor the status of the uploaded file. As an example, the upload or service 906 may use the sha1sum as a lookup key. Possible states for the uploaded file may include "error processing," which signifies an error occurred, "processing," which signifies that the file is being processed, or "processed," which signifies that the file has been processed.

The storage service 908 is responsible for storing extracted PHI data so it can later be retrieved for re-identification. When the storage service is run the storage service communicates with the ASP system 504 and retrieves the plaintext data key and encrypted data key, as discussed above. These keys are then stored in memory. Any data the storage service 908 writes to disk is encrypted with the plaintext data key and is stored alongside the encrypted data key which identifies the plaintext data key that was used to encrypt the data.

Figure 14A:
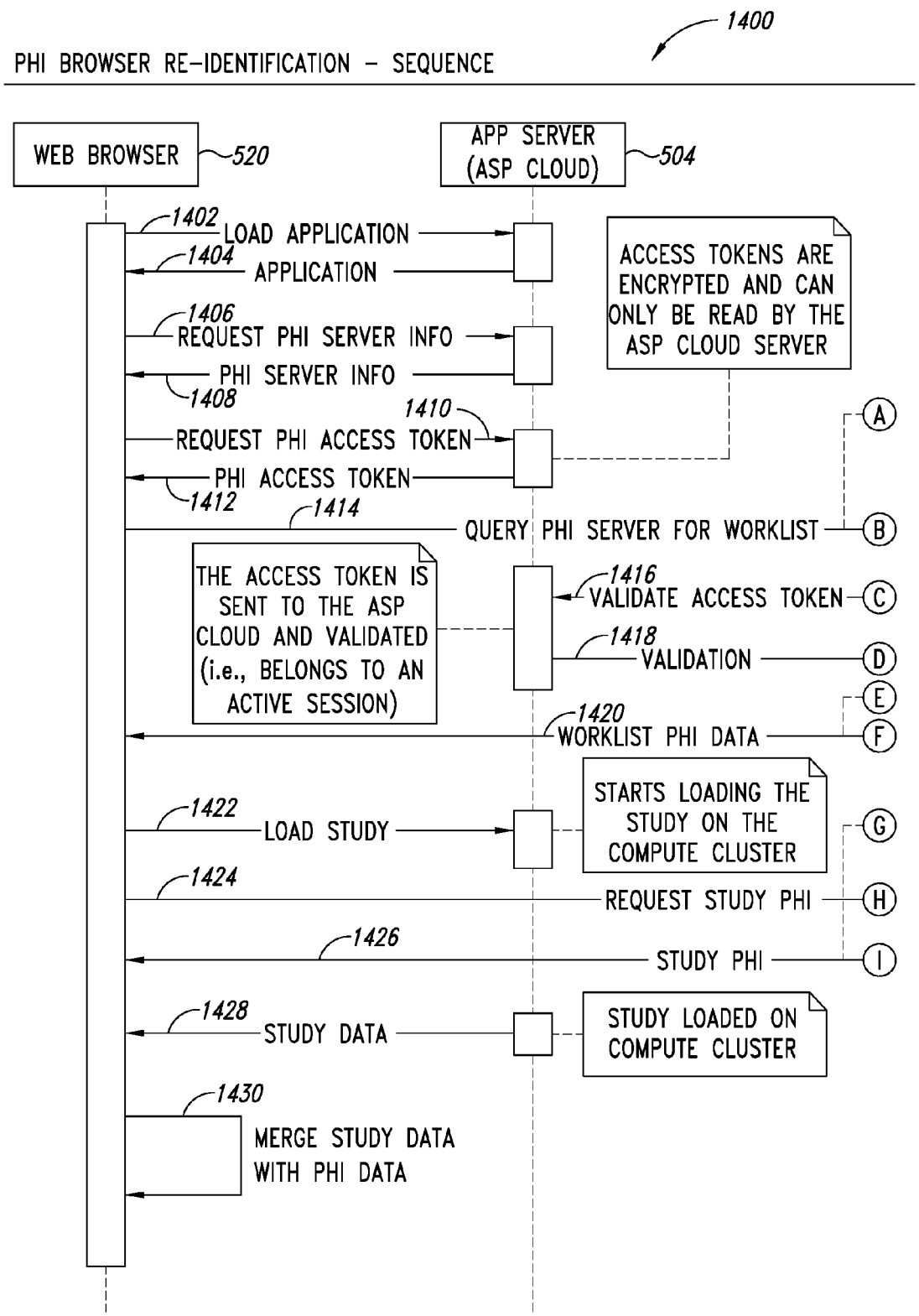
FIGS. 14A-14B are a system sequence diagram illustrating a process for web browser re-identification, according to one illustrated embodiment.
Figure 14B:
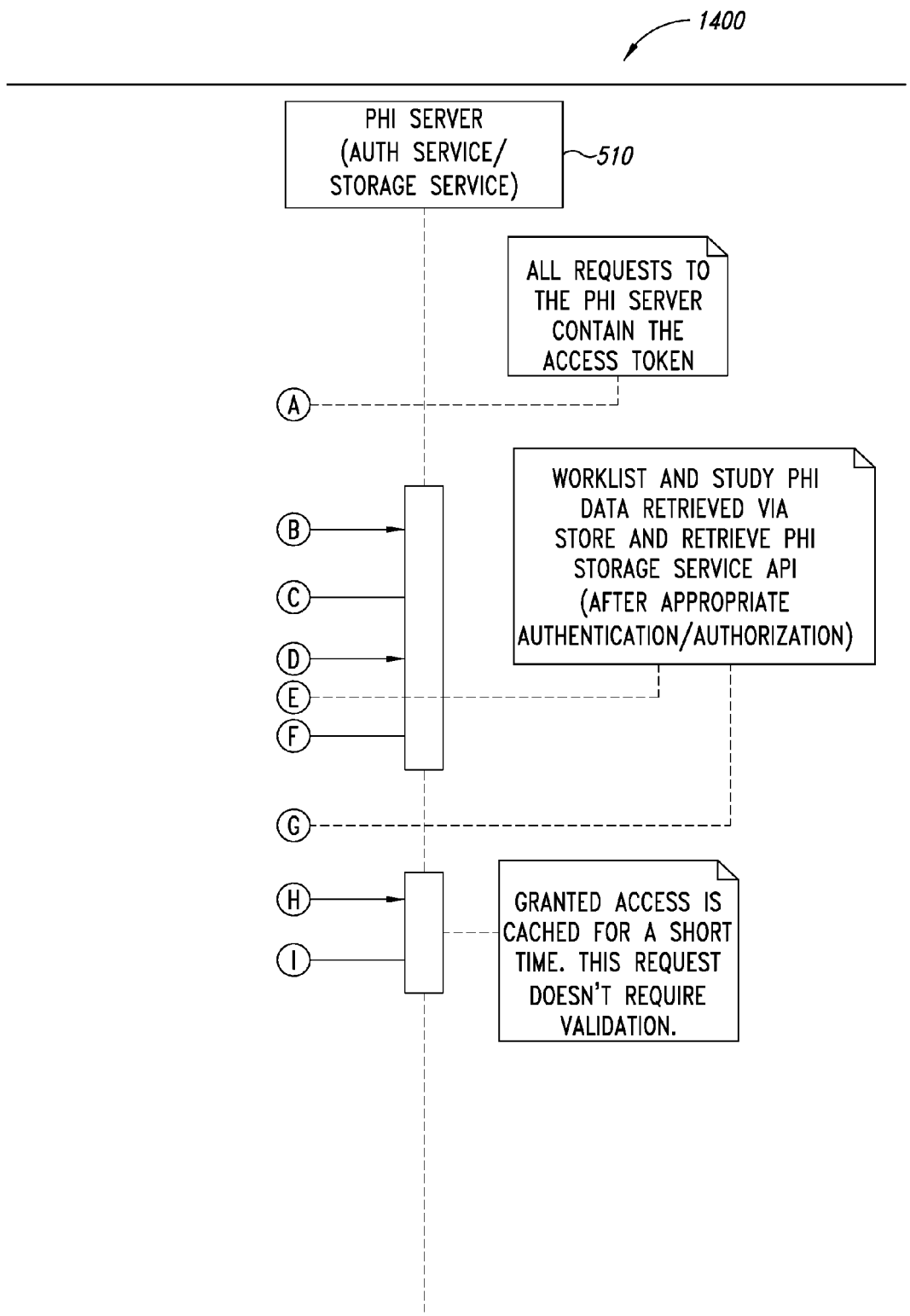

FIGS. 14A-14B (collectively, FIG. 14) are a system sequence diagram 1400 illustrating a process 1400 for re-identification of the data in a web browser executing a web application on the client processor-based device 520 (FIG. 5). At 1402, the web browser sends a request to the ASP system 504 to load an application. At 1404 the ASP system 504 loads the application on the web browser. A user who has successfully been authenticated on the web application of the ASP system 504 may be given a web token (e.g., JSON Web Token). As discussed above, this web token is sent to the PHI system 510, by the web browser, when requesting data. The SSL proxy service 1106 (FIG. 11) forwards all data requests to an authorization service of the PHI system 510 to ensure that the user still has valid, authenticated access to the web application. This is a transparent process as far as the user is concerned.

At 1406, the web browser requests information about the PHI system 510 from the ASP system 504. At 1408, the ASP system 504 sends the PHI system information to the web browser. At 1410, the web browser requests a PHI access token from the ASP system 504. PHI access tokens are encrypted and can only be read by the ASP system 504. At 1412, the ASP system 504 sends the encrypted PHI access token to the web browser.

At 1414, the web browser queries the PHI system 510 for a worklist of available studies. All requests to the PHI system 510 contain the encrypted PHI access token. At 1416, the PHI system 510 sends encrypted access token to the ASP system 504 for validation. The ASP system 504 confirms that the access token is valid (i.e., the access token belongs to an active session). At 1418, the ASP system 504 sends a notification to the PHI system 510 indicating that the access token is valid.

After appropriate authentication/authorization, the PHI system 510 retrieves the worklist and study PHI data via an API of the storage service 908. At 1420, the PHI system 510 sends the worklist PHI data to the web browser.

At 1422, upon selection of a study from the worklist, the web browser sends a request to the ASP system 504 to load a study. Responsive to such a request, the ASP system starts loading the study onto a computing system (e.g., a compute cluster). At 1424, the web browser sends a request to the PHI system 510 for PHI data associated with the selected study. The granted access may be cached for a short time and, as such, this request may not require validation. At 1426, the PHI system 510 sends the PHI data for the selected study to the web browser. At 1428, once the study is loaded on the compute cluster, the ASP system 504 sends the study data to the web browser 520.

At 1430, the web browser merges the study data received from the ASP system 504 with the PHI data received from the PHI system 510 and presents the same to the user for use of the services provided by the ASP. Thus, using the process 1400, the user has access to the full study data and analytics provided by the ASP system 504 without providing the ASP system with any access to PHI data.

Figure 15A:
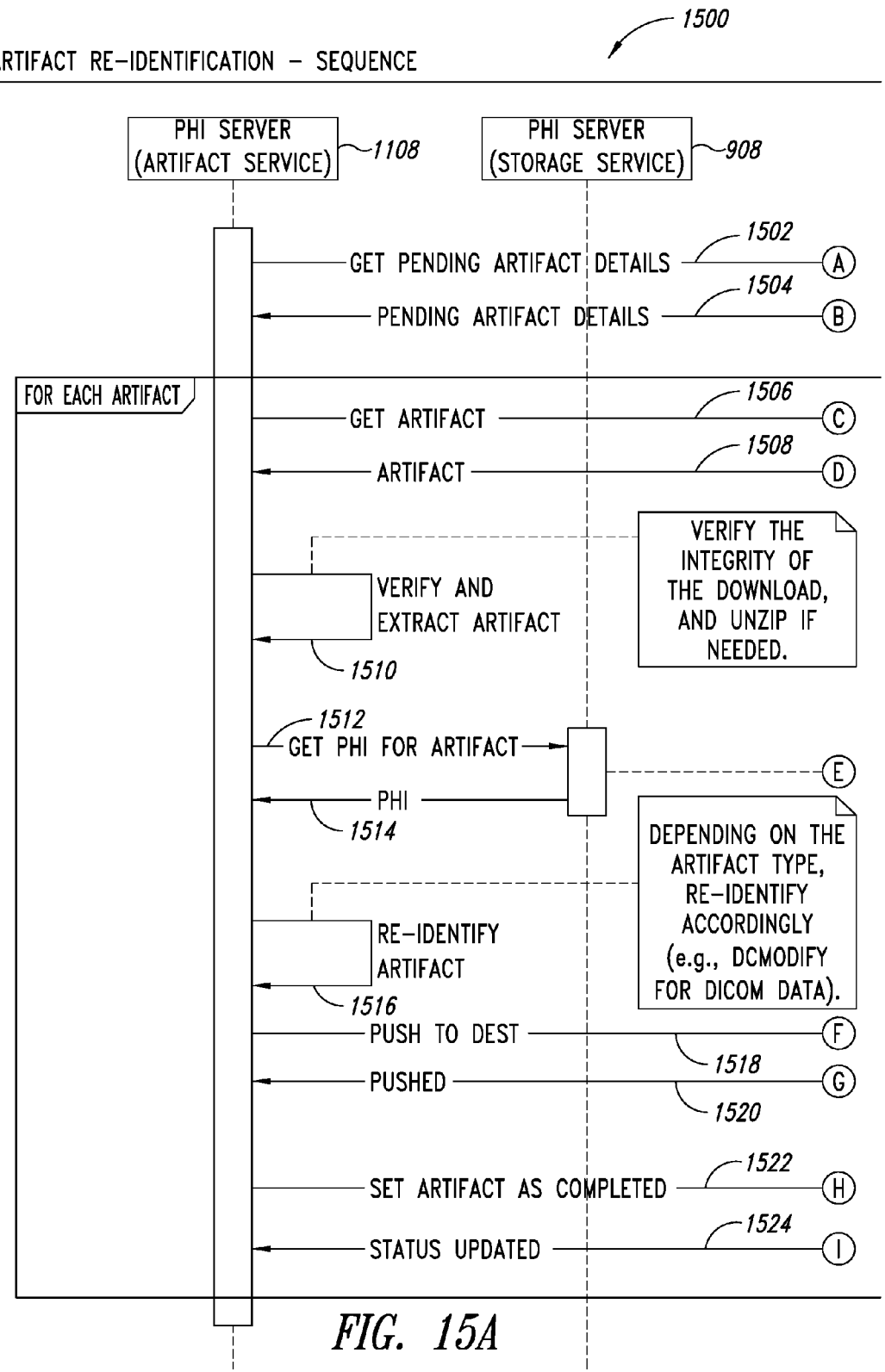
FIGS. 15A-15B are a system sequence diagram illustrating a process for implementing an artifact re-identification service, according to one illustrated embodiment.
Figure 15B:
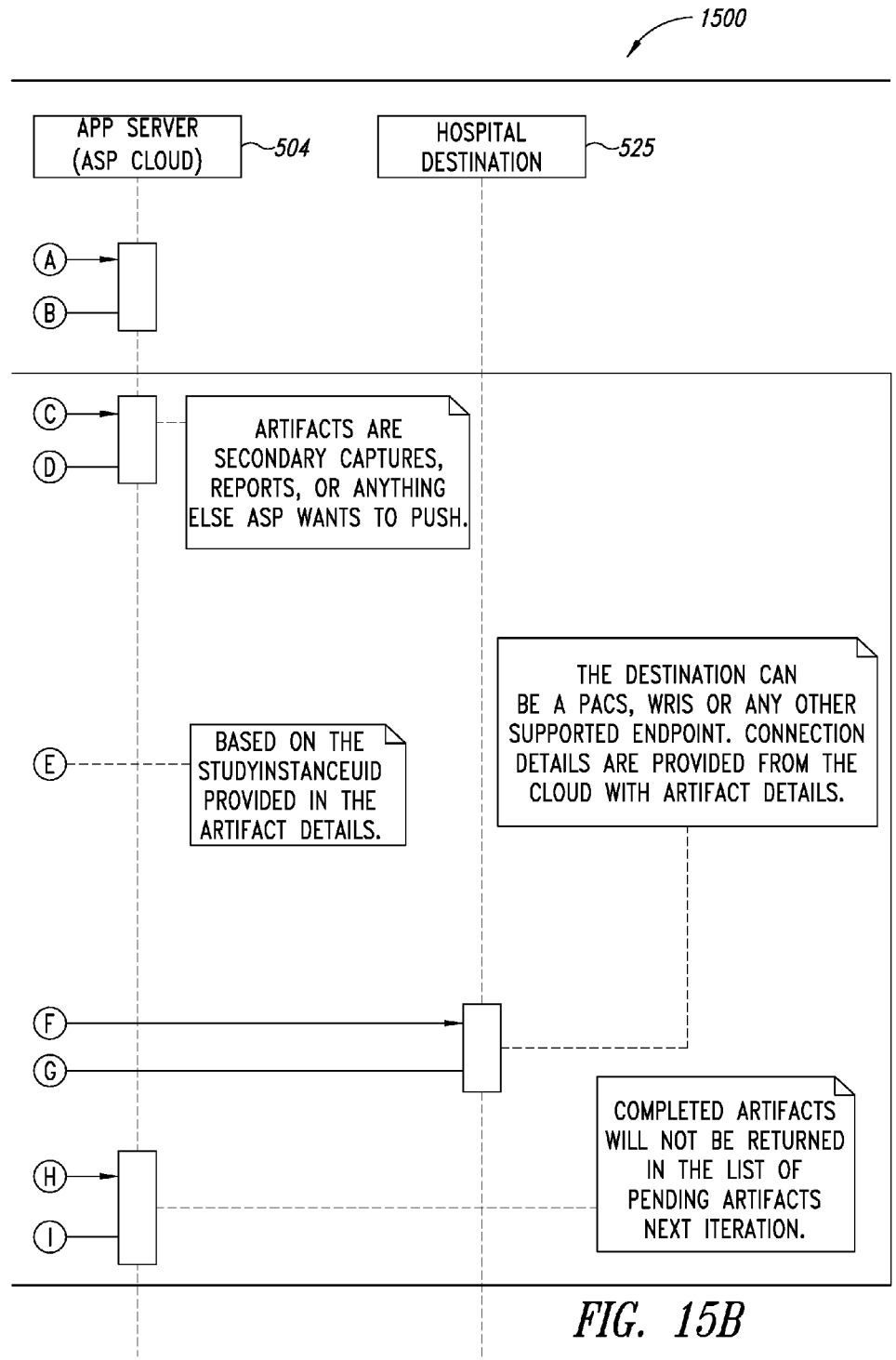

FIGS. 15A-15B (collectively, FIG. 15) are a system sequence diagram illustrating a process 1500 for implementing the artifact re-identification service 1108. The artifact re-identification service 1108 is responsible for contacting the ASP system 504, downloading any pending artifacts, re-identifying the downloaded artifacts, and storing them to a medical provider destination system, such as the PACS 525, a web-based radiology information system (WRIS), etc.

At 1502, the artifact re-identification service 1108 sends a request to the ASP system 504 requesting a list of pending artifacts. At 1504, the ASP system 504 provides the artifact rei-identification service 1108 with a list of pending artifacts.

At 1506, the artifact re-identification service 1108 sends a request to the ASP system 504 to get one of the pending artifacts in the received list of pending artifacts. Artifacts may be secondary capture objects, reports, or anything else that the ASP system 508 may want to push to the medical provider destination storage 525. At 1508, the ASP system 504 sends the requested artifact to the artifact re-identification service 1108.

At 1512, the artifact service 1108 requests PHI data for the artifact from the storage service 908. This request may utilize the obfuscated StudyInstanceUID tag, as supplied in the response, to query the storage service 908 for the original, associated tag information for that StudyInstanceUID. At 1514, the storage service 908 of the PHI system 510 sends the PHI data to the artifact service 1108.

At 1516, the artifact service 1108 re-identifies the artifact. For example, for DICOM data, the dcmodify utility may be used to rewrite the DICOM tags for the artifact to match those that were originally stored.

Upon successful re-identification, the artifact pushed to the medical provider destination storage 525. The destination may be a PACS, WRIS, or any other supported endpoint. Connection details may be provided from the ASP system 504 with the artifact details.

At 1522, the artifact service 1108 sends a notification to the ASP system 504 indicating that the artifact re-identification process for that artifact is completed. At 1524, the ASP system 504 notifies the artifact service 1104 that the status for that artifact has been updated, indicating that such artifact will no longer be returned in the list of pending artifacts during the next iteration.

The above described automated approaches remove the subjectivity in identifying anatomical structure and flow, which is endemic in conventional approaches, providing a high level or repeatability. This repeatability allows new uses for the MRI data. For example, Mill data for single patient may be reliably reviewed across different sessions for trends. Even more surprisingly, MRI data for a plurality of patients may be reliably reviewed for trends across a population or demographic.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/571,908, filed Jul. 7, 2011; International Patent Application No. PCT/US2012/045575, filed Jul. 5, 2012; U.S. Provisional Patent Application No.

61/928,702, filed Jan. 17, 2014; International Patent Application No. PCT/US2015/011851, filed Jan. 16, 2015; U.S. patent application Ser. No. 15/112,130 filed Jul. 15, 2016; and U.S. Provisional Patent Application No. 62/260,565, filed Nov. 29, 2015; U.S. Provisional Patent Application No. 62/415,203 filed Oct. 31, 2016; and U.S. Provisional Patent Application No. 62/415,666 filed Nov. 1, 2016, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operating a medical analytics platform, the medical analytics platform comprising an analytics service provider (ASP) system and a protected health information (PHI) system, the method comprising:
storing, by at least one processor of the ASP system, de-identified medical study data on at least one nontransitory processor-readable storage medium of the ASP system;
storing, by at least one processor of the PHI system, PHI data associated with the de-identified medical study data on at least one nontransitory processor-readable storage medium of the PHI system;
receiving, by the at least one processor of the ASP system, a request for a PHI access token from a client processor-based device over at least one communications network;
sending, by the at least one processor of the ASP system, an encrypted PHI access token to the client processor-based device over the at least one communications network;
receiving, by the at least one processor of the PHI system, a request for PHI data for the medical study from the client processor-based device, the request including the encrypted PHI access token;
sending, by the at least one processor of the PHI system, the encrypted PHI access token to the ASP system over the at least one communications network;
validating, by the at least one processor of the ASP system, the received encrypted PHI access token;
notifying, by the at least one processor of the ASP system, the PHI system that the PHI access token is valid;
sending, by the at least one processor of the PHI system, PHI data for a requested medical study to the client processor-based device over the at least one communications network responsive to the at least one processor of the PHI system receiving the validation notification from the ASP system; and
sending, by the at least one processor of the ASP system, de-identified medical study data for the requested medical study to the client processor-based device over the at least one communications network.

2. The method of claim 1 wherein the PHI system is communicatively coupled to a private network, the method further comprising:
verifying, by the at least one processor of the ASP system or the at least one processor of the PHI system, that the client processor-based device has access to the private network.

3. The method of claim 1, further comprising:
receiving, by the at least one processor of the PHI system, medical study data which includes PHI data;
removing, by the at least one processor of the PHI system, the PHI data from the medical study data to generate de-identified medical study data;
storing, by the at least one processor of the PHI system, the PHI data in the at least one nontransitory processor-readable storage medium of the PHI system; and
sending, by the at least one processor of the PHI system, the de-identified medical study data to the ASP system over the at least one communications network.

4. The method of claim 3 wherein receiving medical study data which includes PHI data comprises receiving medical imaging data from a scanner.

5. The method of claim 3 wherein sending the de-identified medical study data to the ASP system comprises sending the de-identified medical study data to the ASP system using a representational state transfer (REST) application programming interface.

6. The method of claim 3 wherein removing the PHI data from the medical study data comprises:
removing, by the at least one processor of the PHI system, fields which are allowed to be deleted; and
replacing, by the at least one processor of the PHI system, data in fields which are not allowed to be deleted with obfuscated replacement data.

7. The method of claim 3, further comprising:
associating, by the at least one processor of the PHI system, a unique identifier with the medical study data for a medical study;
storing, by the at least one processor of the PHI system, the unique identifier in the at least one nontransitory processor-readable storage medium of the PHI system; and
sending, by the at least one processor of the PHI system, the unique identifier with the de-identified medical data for the medical study to the ASP system over the at least one communications network.

8. The method of claim 1, further comprising:
receiving, by at least one processor of the client processor-based device, the PHI data from the PHI system over the at least one communications network;
receiving, by the at least one processor of the client processor-based device, the de-identified medical study data from the ASP system over the at least one communications network;
merging, by the at least one processor of the client processor-based device, the PHI data and the de-identified medical study data to generate re-identified medical study data; and
presenting, by the at least one processor of the client processor-based device, the re-identified medical study data to a user of the client processor-based device.

9. The method of claim 1, further comprising:
generating, by the at least one processor of the ASP system, analytics data relating to the de-identified medical study data; and
sending, by the at least one processor of the ASP system, the generated analytics data to the PHI system over the at least one communications network.

10. The method of claim 9, further comprising:
receiving, by the at least one processor of the ASP system, a request to generate analytics data from the client processor-based device over the at least one communications network,
wherein generating the analytics data is responsive to receiving the request to generate analytics data from the client processor-based device.

11. The method of claim 9 wherein generating analytics data comprises generating at least one of a report or a secondary capture object, and sending the generated analytics data to the PHI system comprises sending the at least one of the report or the secondary capture object to the PHI system over the at least one communications network for storage on the at least one nontransitory processor-readable storage medium communicatively coupled with the PHI system.

12. The method of claim 1, further comprising:
providing, by the at least one processor of the PHI system, a list of available studies to the client processor-based device over the at least one communications network; and
receiving, by the at least one processor of the PHI system, a selection of at least one of the available studies in the list from the client processor-based device over the at least one communications network.

13. The method of claim 1, further comprising:
periodically sending, by the at least one processor of the PHI system, a check for updates to the ASP system over the at least one communications network;
determining, by the at least one processor of the ASP system, whether any updates to the PHI system are needed; and
responsive to determining that at least one update of the PHI system is needed, sending, by the at least one processor of the ASP, update data to the PHI system over the at least one communications network.

14. A method of operating an analytics service provider (ASP) system of a medical analytics platform, the medical analytics platform comprising the ASP system and a protected health information (PHI) system, the PHI system storing PHI data associated with de-identified medical study data on at least one nontransitory processor-readable storage medium of the PHI system, the method comprising:
storing, by at least one processor of the ASP system, the de-identified medical study data on at least one nontransitory processor-readable storage medium of the ASP system;
sending, by the at least one processor of the ASP system, de-identified medical study data for a requested medical study to a client processor-based device over at least one communications network to be merged by the client processor-based device with PHI data received by the client processor-based device from the PHI system over the at least one communications network;
receiving, by the at least one processor of the ASP system, a request for a PHI access token from the client processor-based device over the at least one communications network;
sending, by the at least one processor of the ASP system, an encrypted PHI access token to the client processor-based device over the at least one communications network;
receiving, by the at least one processor of the ASP system, the encrypted PHI access token from the PHI system over the at least one communications network;
validating, by the at least one processor of the ASP system, the received encrypted PHI access token; and
notifying, by the at least one processor of the ASP system, the PHI system that the PHI access token is valid.

15. The method of claim 14, further comprising:
receiving, by the at least one processor of the ASP system, the de-identified medical study data from the PHI system over the at least one communications network.

16. The method of claim 14, further comprising:
generating, by the at least one processor of the ASP system, analytics data relating to the de-identified medical study data; and
sending, by the at least one processor of the ASP system, the generated analytics data to the PHI system over the at least one communications network.

17. The method of claim 16, further comprising:
receiving, by the at least one processor of the ASP system, a request to generate analytics data from the client processor-based device over the at least one communications network,
wherein generating the analytics data is responsive to receiving the request to generate analytics data from the client processor-based device.

18. The method of claim 16 wherein generating analytics data comprises generating at least one of a report or a secondary capture object, and sending the generated analytics data to the PHI system comprises sending the at least one of the report or the secondary capture object to the PHI system over the at least one communications network for storage on the at least one nontransitory processor-readable storage medium communicatively coupled with the PHI system.

19. The method of claim 14, further comprising:
periodically receiving, by the at least one processor of the ASP system, a check for updates from the PHI system over the at least one communications network;
determining, by the at least one processor of the ASP system, whether any updates to the PHI system are needed; and
responsive to determining that at least one update of the PHI system is needed, sending, by the at least one processor of the ASP, update data to the PHI system over the at least one communications network.

20. The method of claim 14, further comprising:
receiving, by at least one processor of the client processor-based device, the PHI data from the PHI system over the at least one communications network;
receiving, by the at least one processor of the client processor-based device, the de-identified medical study data from the ASP system over the at least one communications network;
merging, by the at least one processor of the client processor-based device, the PHI data and the de-identified medical study data to generate re-identified medical study data; and
presenting, by the at least one processor of the client processor-based device, the re-identified medical study data to a user of the client processor-based device.

21. A method of operating a protected health information (PHI) system of a medical analytics platform, the medical analytics platform comprising the PHI system and an analytics service provider (ASP) system, the ASP system storing de-identified medical study data on at least one nontransitory processor-readable storage medium of the ASP system, the method comprising:
storing, by at least one processor of the PHI system, PHI data associated with the de-identified medical study data on at least one nontransitory processor-readable storage medium of the PHI system;

receiving, by the at least one processor of the PHI system, a request for PHI data for the medical study from a client processor-based device, the request including an encrypted PHI access token;

sending, by the at least one processor of the PHI system, the encrypted PHI access token to the ASP system over the at least one communications network for validation; and receiving, by the at least one processor of the PHI system, a notification from the ASP system that the PHI access token is valid; and sending, by the at least one processor of the PHI system, PHI data for a requested medical study to a client processor-based device over at least one communications network to be merged by the client processor-based device with de-identified medical study data received by the client processor-based device from the ASP system over the at least one communications network.

22. The method of claim 21, further comprising:

receiving, by the at least one processor of the PHI system, medical study data which includes PHI data;

removing, by the at least one processor of the PHI system, the PHI data from the medical study data to generate de-identified medical study data;

storing, by the at least one processor of the PHI system, the PHI data in the at least one nontransitory processor-readable storage medium of the PHI system; and sending, by the at least one processor of the PHI system, the de-identified medical study data to the ASP system over the at least one communications network.

23. The method of claim 22 wherein receiving medical study data which includes PHI data comprises receiving medical imaging data from a scanner.

24. The method of claim 22 wherein sending the de-identified medical study data to the ASP system comprises sending the de-identified medical study data to the ASP system using a representational state transfer (REST) application programming interface.

25. The method of claim 22 wherein removing the PHI data from the medical study data comprises:

removing, by the at least one processor of the PHI system, fields which are allowed to be deleted; and replacing, by the at least one processor of the PHI system, data in fields which are not allowed to be deleted with obfuscated replacement data.

26. The method of claim 22, further comprising:

associating, by the at least one processor of the PHI system, a unique identifier with the medical study data for a medical study;

storing, by the at least one processor of the PHI system, the unique identifier in the at least one nontransitory processor-readable storage medium of the PHI system; and sending, by the at least one processor of the PHI system, the unique identifier with the de-identified medical data for the medical study to the ASP system over the at least one communications network.

27. The method of claim 21, further comprising:

receiving, by the at least one processor of the PHI system, analytics data relating to the de-identified medical study data from the ASP system over the at least one communications network; and storing, by the at least one processor of the PHI system, the received analytics data on at least one nontransitory processor-readable storage medium communicatively coupled with the PHI system.

28. The method of claim 21, further comprising:

providing, by the at least one processor of the PHI system, a list of available studies to the client processor-based device over the at least one communications network; and receiving, by the at least one processor of the PHI system, a selection of at least one of the available studies in the list from the client processor-based device over the at least one communications network.

29. The method of claim 21, further comprising:

periodically sending, by the at least one processor of the PHI system, a check for updates to the ASP system over the at least one communications network; and receiving, by the at least one processor of the PHI system, update data from the ASP system over the at least one communications network.

30. The method of claim 21, further comprising:

receiving, by at least one processor of the client processor-based device, the PHI data from the PHI system over the at least one communications network;

receiving, by the at least one processor of the client processor-based device, the de-identified medical study data from the ASP system over the at least one communications network;

merging, by the at least one processor of the client processor-based device, the PHI data and the de-identified medical study data to generate re-identified medical study data; and presenting, by the at least one processor of the client processor-based device, the re-identified medical study data to a user of the client processor-based device.

* * * * *